United States Patent
Wheeler et al.

(10) Patent No.: US 6,586,410 B1
(45) Date of Patent: *Jul. 1, 2003

(54) LIPID-NUCLEIC ACID PARTICLES PREPARED VIA A HYDROPHOBIC LIPID-NUCLEIC ACID COMPLEX INTERMEDIATE AND USE FOR GENE TRANSFER

(75) Inventors: Jeffery J. Wheeler, Richmond (CA); Marcel B. Bally, Bowen Island (CA); Yuan-Peng Zhang, Vancouver (CA); Dorothy L. Reimer, Vancouver (CA); Michael Hope, Vancouver (CA); Pieter R. Cullis, Vancouver (CA); Peter Scherrer, Vancouver (CA)

(73) Assignee: Inex Pharmaceuticals Corporation, Burnaby (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/566,700

(22) Filed: May 8, 2000

Related U.S. Application Data

(63) Continuation of application No. 09/431,594, filed on Nov. 1, 1999, which is a continuation of application No. 08/660,025, filed on Jun. 6, 1996, now Pat. No. 5,976,567, which is a continuation-in-part of application No. 08/484,282, filed on Jun. 7, 1995, now Pat. No. 5,981,501, which is a continuation-in-part of application No. 08/485,458, filed on Jun. 7, 1995, now Pat. No. 5,705,385.

(51) Int. Cl.[7] ........................ A61K 48/00; A61K 9/127

(52) U.S. Cl. .......................... 514/44; 435/6; 424/450

(58) Field of Search ................... 424/450; 435/320.1, 435/375, 458; 514/44; 536/23.1, 24.5

(56) References Cited

U.S. PATENT DOCUMENTS

| | | |
|---|---|---|
| 4,394,448 A | 7/1983 | Szoka, Jr. et al. |
| 4,438,052 A | 3/1984 | Weder et al. |
| 4,515,736 A | 5/1985 | Deamer |
| 4,598,051 A | 7/1986 | Papahadjopoulos et al. |
| 4,897,355 A | 1/1990 | Eppstein et al. |
| 5,013,556 A | 5/1991 | Woodle et al. |
| 5,171,678 A | 12/1992 | Behr et al. |
| 5,208,036 A | 5/1993 | Eppstein et al. |
| 5,225,212 A | 7/1993 | Martin et al. |
| 5,264,618 A | 11/1993 | Felgner et al. |
| 5,279,833 A | 1/1994 | Rose |
| 5,283,185 A | 2/1994 | Epand et al. |
| 5,320,906 A | 6/1994 | Eley et al. |
| 5,545,412 A | 8/1996 | Eppstein et al. |
| 5,578,475 A | 11/1996 | Jessee et al. |
| 5,641,662 A | 6/1997 | Debs et al. |
| 5,656,743 A | 8/1997 | Busch et al. |
| 5,703,055 A | 12/1997 | Felgner et al. |
| 5,705,385 A | 1/1998 | Bally et al. |
| 5,820,873 A | * 10/1998 | Choi et al. |
| 5,981,501 A | * 11/1999 | Wheeler et al. |

FOREIGN PATENT DOCUMENTS

| | | |
|---|---|---|
| WO | WO 91/10624 | 10/1991 |
| WO | WO 91/16024 | 10/1991 |
| WO | WO 93/05162 | 3/1993 |
| WO | WO 93/12240 | 6/1993 |
| WO | WO 93/12756 | 7/1993 |
| WO | WO 93/24640 | 12/1993 |
| WO | WO 93/25673 | 12/1993 |
| WO | WO 95/02698 | 1/1995 |
| WO | WO 95/18863 | 7/1995 |
| WO | WO 95/35301 | 12/1995 |
| WO | WO 9602655 A1 | 2/1996 |
| WO | WO 96/10390 | 4/1996 |
| WO | WO 96/41873 | 12/1996 |

OTHER PUBLICATIONS

Ballas, et al., *Biochim. Biophys. Acta* 939:8–18 (1988).
Behr, *Acc. Chem. Res.* 26:274–78 (1993).
Brigham, et al., "Rapid Communication: In Vivo Transfection of Murine Lungs with a Functioning Prokaryotic Gene Using a Liposome Vehicle," *Am. J. Med. Sci.* 298:278–281 (1989).
Culver, *Gene Theraphy: A Handbook for Physicians*, Mary Ann Liebert, Inc. publishers, 33–40 (1994).
Duzgunes, *Subcellular Biochemistry* 11: 195–286 (1985).
Enoch, et al., *Proc. Nat'l Acad. Sci USA*, 76(1):145–149 (1979).
Felgner, et al., *Proc. Nat'l Acad. Sci, USA* 84:7413–7417 (1987).
Gao, et al., *Biochem. Biophys. Res. Comm.* 179:280–285 (1991).
Gershon, et al., *Biochemistry* 32:7413–7151 (1993).
Hawley–Nelson, et al., "Lipofectamine™Reagent: A New, Higher Efficiency Polycationic Liposome Transfection Reagent," *Focus* 15(3):73 (1993).
Hyde, et al., "Correction of the Ion Transport Defect in Systic Fibrosis Transgenic Mice by Gene Therapy," *Nature* 362:250–256 (1993).
Juliano, *Biochem. Biophys. Res. Commun.* 63:651–658 (1975).
Legendre, *Pharm. Res.* 9:1235–1242 (1992).
Leventis, et al., "Interactions of Mammalian Cells With Lipid Dispersions Containing Novel Metabolizable Cationic Amphiphiles," *Biochem. Biophys. Acta* 1023:124 (1990).
Puyal et al., *Eur. Biochem.*, 228:697–703 (1995).

(List continued on next page.)

Primary Examiner—Sean McGarry
Assistant Examiner—Janet L. Epps-Ford
(74) Attorney, Agent, or Firm—Townsend & Townsend & Crew LLP

(57) ABSTRACT

Novel lipid-nucleic acid particulate complexes which are useful for in vitro or in vivo gene transfer are described. The particles can be formed using either detergent dialysis methods or methods which utilize organic solvents. Upon removal of a solubilizing component (i.e., detergent or an organic solvent) the lipid-nucleic acid complexes form particles wherein the nucleic acid is serum-stable and is protected from degradation. The particles thus formed have access to extravascular sites and target cell populations and are suitable for the therapeutic delivery of nucleic acids.

29 Claims, 35 Drawing Sheets

OTHER PUBLICATIONS

Stamatatos, et al., "Interactions of Cationic Lipid Vesicles With Negatively Charged Phospholipid Vesicles and Biological Membranes," *Biochemistry* 27:3917–3925 (1988).

Szoka, et al., *Ann. Rev. Biophys. Bioeng.* 9:467–508 (1980).

Wilson, et al., *Biochemistry* 18:2192–2196 (1979).

Woodle, et al., "Versatility in Lipid Compositions Showning Prolonged Circulation with Sterically Stabilized Liposomes," *Biochim. Biophys. Acta* 1105:193–200 (1992).

Zhu, et al., "Systemic Gene Expression After Intravenous DNA Delivery into Adult Mice," *Science* 261:209–211 (1993).

Cortesi, Rita, et al., "Effect of cationic liposome composition on in vitro cytotoxicity and protective effect on carried DNA," *International Journal of Pharmaceutics* 139:69–78 (1996).

Dwarki, V.J., et al., "Cationic Liposome–Mediated RNA Transfection," *Methods in Enzymology* 217:644–54 (1993).

Felgner, Jiin H., et al., "Enhanced Gene Delivery and Mechanism Studies with a Novel Series of Cationic Lipid Formulations," *The Journal of Biological Chemistry* 269(4):2550–2561 (Jan. 1994).

Felgner, Jiin, et al., "Cationic Lipid–Mediated Transfection In Mammalian Cells: "Lipofection"", *J.l Tiss. Cult. Meth.* 15:63–68 (1993).

Felgner, P.L., et al., "Cationic Liposome Mediated Transfection," *Proc. West. Pharmacol. Soc.* 32:115–121 (1989).

Guy–Caffey, Judith K., et al., "Novel Polyaminolipids Enhance the Cellular Uptake of Oligonucleotides," *The Journal of Biological Chemistry* 270(52):31391–31396 (Dec. 1995).

van der Woude, I., et al., "Parameters influencing the introduction of plasmid DNA into cells by the use of synthetic amphiphiles as a carrier system," *Biochimica et Biophysica Acta* 1240:34–40 (1995).

* cited by examiner

LIPID-NUCLEIC ACID PARTICLES PREPARED VIA A HYDROPHOBIC LIPID-NUCLEIC ACID COMPLEX INTERMEDIATE AND USE FOR GENE TRANSFER

This application is a continuation of and claims the benefit of U.S. Continuation application Ser. No. 09/431, 594, filed Nov. 1, 1999, the disclosure of which is incorporated by reference. Application Ser. No. 09/431,594 is a continuation of Ser. No. 08/660,025, filed Jun. 6, 1996, U.S. Pat. No. 5,976,567, which is a continuation-in-part of U.S. application Ser. No. 08/485,458 now U.S. Pat. No. 5,705, 385 and of U.S. application Ser. No. 08/484,282, now U.S. Pat. No. 5,981,501 both filed on Jun. 7, 1995.

FIELD OF THE INVENTION

This invention relates to lipid-nucleic acid particles which are useful for the introduction of nucleic acids into cells, and methods of making and using them. The invention provides a circulation-stable, characterizable delivery vehicle for the introduction of plasmids or antisense compounds into cells. These vehicles are safe, stable, and practical for clinical use.

BACKGROUND OF THE INVENTION

Gene transfer into genetically impaired host cells in order to correct the genetic defects has vast potential for successfully treating a variety of thus far hitherto untreatable medical conditions. There are currently six major non-viral methods by which genes are introduced into host cells: (i) direct microinjection, (ii) calcium phosphate precipitation, (ii) DEAE-dextran complexes, (iv) electroporation, (v) cationic lipid complexes and (vi) reconstituted viruses and virosomes (see Chang, et al., *Focus* 10:88 (1988)).

Most reported examples of gene transfer have been performed in vitro. In vivo gene transfer is complicated by serum interactions, immune clearance, enzymatic degradation of the genes, toxicity and biodistribution. In in vivo administration, selection is not possible, and a reasonably high frequency of transformation is necessary to achieve sufficient expression to compensate for a defective endogenous gene.

The in vivo gene transfer methods under study in the clinic consist almost entirely of viral vectors. Although viral vectors have the inherent ability to transport nucleic acids across cell membranes and some can integrate exogenous DNA into the chromosomes, they can carry only limited amounts of DNA. In addition, their use poses significant risks. One such risk is that the viral vector may revert to a pathogenic genotype either through mutation or genetic exchange with a wild type virus.

In view of these limitations and risks, alternative non-viral-based gene transfer methods have been developed. These methods use often plasmid vectors, which are small circular sequences of DNA, as vectors for DNA delivery. However, most plasmids do not possess the attributes required for intracellular delivery and therefore sophisticated delivery systems are required.

Cationic lipid complexes are presently the most effective generally used means of introducing non-viral nucleic acids into cells. A number of different formulations incorporating cationic lipids are commercially available. These include:(i) LIPOFECTION® (which uses 1,2-dioleyloxy-3-(N,N,N-trimethylamino)propane chloride, or DOTMA, see Eppstein, et al., U.S. Pat. No. 4,897,355); LIPO-FECTAMINE® (which uses DOSPA, see Hawley-Nelson, et al., Focus 15(3):73 (1993)); and LIPOFECTACE® (which uses N,N-distearyl-N,N-dimethyl-ammonium bromide, or DDAB, see Rose, U.S. Pat. No. 5,279,833). Others have reported alternative cationic lipids that work in essentially the same manner but with different efficiencies, for example 1,2-dioleoyloxy-3-(N,N,N-trimethylamino) propane chloride, or DOTAP (see Stomatatos, et al., Biochemistry 27: 3917–3925 (1988)); glycerol based lipids (see Leventis, et al., Biochem. Biophys. Acta 1023:124 (1990); lipopolyamines (see, Behr, et al., U.S. Pat. No. 5,171,678) and cholesterol based lipids (see Epand, et al., WO 93/05162, and U.S. Pat. No. 5,283,185). It has been reported that DOTMA and related compounds are significantly more active in gene transfer assays than their saturated analogues (see, Feigner, et al., WO91/16024). However, both DOTMA and DOSPA based formulations, despite their efficiency in effecting gene transfer, are prohibitively expensive. DDAB on the other hand is inexpensive and readily available from chemical suppliers but is less effective than DOTMA in most cell lines. Another disadvantage of the current lipid systems is that they are not appropriate for intravenous injection.

Lipid-based vectors used in gene transfer have generally been formulated in one of two ways. In one method, the nucleic acid is introduced into preformed liposomes made of mixture of cationic lipids and neutral lipids. The complexes thus formed have undefined and complicated structures and the lipofection efficiency is severely reduced by the presence of serum. A second method involves the formation of DNA complexes with mono- or poly-cationic lipids without the presence of a neutral lipid. These complexes are often prepared in the presence of ethanol and are not stable in water. Additionally, these complexes are adversely affected by serum (see, Behr, *Acc. Chem. Res.* 26:274–78 (1993)).

An examination of the relationship between the chemical structure of the carrier vehicle and its efficiency of gene transfer has indicated that the characteristics which provide for effective gene transfer would make a carrier unstable in circulation (see, Ballas, et al., *Biochim. Biophys. Acta* 939:8–18 (1988)). Additionally, degradation either outside or inside the target cell remains a problem (see, Duzghines, *Subcellular Biochemistry* 11:195–286 (1985)). Others who have attempted to encapsulate DNA in lipid-based formulations have not overcome these problems (see, Szoka et al., Ann. Rev. Biophys. Bioeng. 9:467 (1980); Deamer, U.S. Pat. No. 4,515,736, and Legendre, *Pharm. Res.* 9:1235–1242 (1992)).

Ideally, a delivery vehicle for a nucleic acid or plasmid will have the following characteristics: a) ease of preparation, b) capable of carrying a large amount of DNA per particle to enable gene transfer of all sizes of genes and reduce the volume of injection, c) homogenous, d) reproducible, e) is serum stable with minimal serum interactions and shields DNA from extracellular degradation, and f) is capable of transfecting target cells in such a way that the DNA is not digested intracellularly.

The present invention provides such compositions and methods for their preparation and use.

SUMMARY OF THE INVENTION

The present invention comprises novel, lipid-nucleic acid particles. The invention also comprises methods of making and using these particles.

In some embodiments, the particles are made by formation of hydrophobic intermediate complexes in either detergent-based or organic solvent-based systems, followed by removal of the detergent or organic solvent. Preferred embodiments are charge-neutralized.

In one embodiment, a plasmid is combined with cationic lipids in a detergent solution to provide a coated plasmid-lipid complex. The complex is then contacted with non-cationic lipids to provide a solution of detergent, a plasmid-lipid complex and non-cationic lipids, and the detergent is then removed to provide a solution of serum-stable plasmid-lipid particles, in which the plasmid is encapsulated in a lipid bilayer. The particles thus formed have a size of about 50–150 nm.

In another embodiment, serum-stable plasmid-lipid particles are formed by preparing a mixture of cationic lipids and non-cationic lipids in an organic solvent; contacting an aqueous solution of plasmid with the mixture of cationic and non-cationic lipids to provide a clear single phase; and removing the organic solvent to provide a suspension of plasmid-lipid particles, in which the plasmid is encapsulated in a lipid bilayer, and the particles are stable in serum and have a size of about 50–150 nm.

Another method of forming lipid-nucleic acid particles involves:
(a) contacting nucleic acids with a solution of non-cationic lipids and a detergent to form a nucleic acid-lipid mixture;
(b) contacting cationic lipids with the nucleic acid-lipid mixture to neutralize the negative charge of said nucleic acids and form a charge-neutralized mixture of nucleic acids and lipids: and
(c) removing the detergent from the charge-neutralized mixture to provide the lipid-nucleic acid particles in which the nucleic acids are protected from degradation.

Another method of forming lipid-nucleic acid particles involves:
(a) contacting an amount of cationic lipids with nucleic acids in a solution; the solution comprising of from about 15–35% water and about 65–85% organic solvent and the amount of cationic lipids being sufficient to produce a +/− charge ratio of from about 0.85 to about 2.0, to provide a hydrophobic, charge-neutralized lipid-nucleic acid complex;
(b) contacting the hydrophobic, charge-neutralized lipid-nucleic acid complex in solution with non-cationic lipids, to provide a lipid-nucleic acid mixture; and
(c) removing the organic solvents from the lipid-nucleic acid mixture to provide lipid-nucleic acid particles in which the nucleic acids are protected from degradation.

The lipid-nucleic acid particles of the present invention are useful for the therapeutic delivery of nucleic acids. In one embodiment, the particles are constructed via a hydrophobic lipid-nucleic acid intermediate (or complex). Upon removal of a solubilizing component (i.e., detergent or an organic solvent) the nucleic acid becomes protected from degradation. The particles thus formed are suitable for use in intravenous nucleic acid transfer as they are stable in circulation, of a size required for pharmacodynamic behavior resulting in access to extravascular sites and target cell populations.

In particular, it is an object of this invention to provide in vitro and in vivo methods for treatment of diseases which involve the overproduction or underproduction of particular proteins. In these methods, a nucleic acid encoding a desired protein or blocking the production of an undesired protein, is formulated into a lipid-nucleic acid particle, and the particles are administered to patients requiring such treatment. Alternatively, cells are removed from a patient, transfected with the lipid-nucleic acid particles described herein, and reinjected into the patient.

BRIEF DESCRIPTION OF THE DRAWINGS

FIGS. 38A and 37B depict the agarose gel electrophoresis of DNA isolated from formulations prepared in 100 mM and 20 mM OGP (charge ratio of 2.1 and SM/DODAC ratio of 1:1) and tested for DNase I sensitivity in the absence (A) and presence (B) of OGP. Panel A: molecular weight standards (lane 1), pCMVβ in the absence of added lipid or DNase I (lane 2), pCMVβ following incubation with DNase I (lane 3), DNA isolated from a dialyzed nucleic acid-lipid particle formulation prepared using 100 mM OGP following incubations in the absence (lane 4) and presence (lane 5) of DNase I, and DNA isolated from particles prepared using 20 mM OGP and dialyzed following incubations in the absence (lane 6) and presence (lane 7) of DNase 1. The first 3 lanes in panel B are identical to those in panel A except that pCMVβ was incubated in 20 mM OGP in the absence (lane 2) and presence (lane 3) of DNase 1. DNA isolated from a formulation prepared in 20 mM OGP (prior to detergent removal) was incubated in the absence (lane 4) and presence (lane 5) of DNase I in 20 mM OGP. Arrow indicates degraded DNA.

DETAILED DESCRIPTION OF THE INVENTION

CONTENTS

Figure 1:
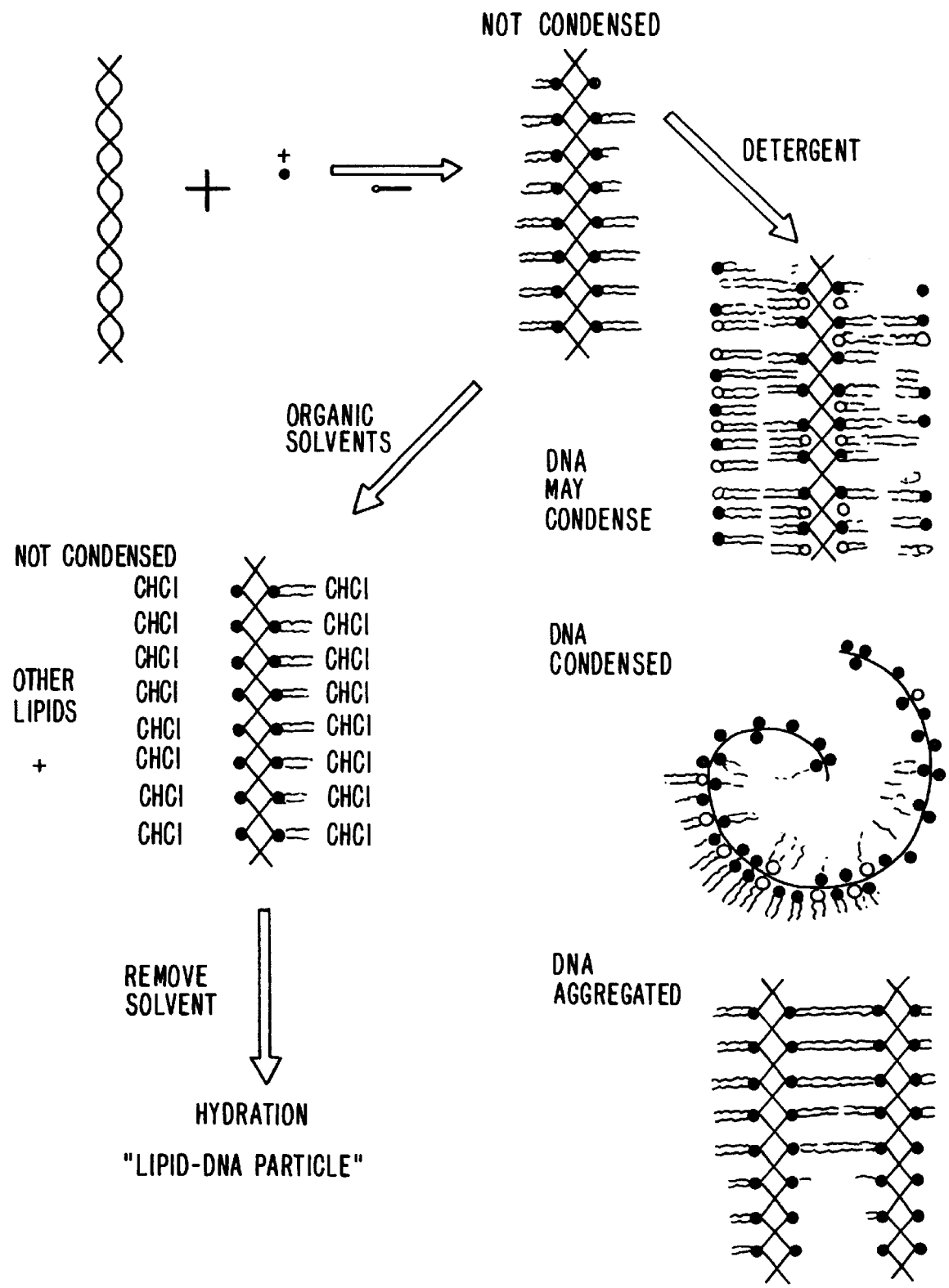
FIG. 1 illustrates a nucleic acid-lipid particle-mediated gene transfer using "sandwich-type" complexes of DNA.

I. Glossary
II. General
III. Embodiments of the invention
   A. Lipid-Nucleic Acid Particles, and Properties Thereof
   B. Methods of Formulating Lipid-Nucleic Acid Particles
   C. Pharmaceutical Preparations
   D. Administration of Lipid-Nucleic Acid Particle Formulations for Gene Transfer
IV. Examples
V. Conclusion

I. Glossary

The following abbreviations are used herein: CHO, Chinese hamster ovary cell line; B16, murine melanoma cell line; DC-Chol, 3β-(N-(N',N'-dimethylaminoethane) carbamoyl) cholesterol (see, Gao, et al., Biochem. Biophys. Res. Comm. 179:280–285 (1991)); DDAB, N,N-distearyl-N,N-dimethylammonium bromide; DMRIE, N-(1,2-dimyristyloxyprop-3-yl)-N,N-dimethyl-N-hydroxyethyl ammonium bromide; DODAC, N,N-dioleyl-N,N-dimethylammonium chloride; DOGS, diheptadecylamidoglycyl spermidine; DOPE, 1,2-sn-dioleoylphoshatidylethanolamine; DOSPA, N-(-(2, 3-dioleyloxy)propyl)-N-(2-(sperminecarboxamido)ethyl)-N,N-dimethylammonium trifluoroacetate; DOTAP, N-(1-(2, 3-dioleoyloxy)propyl)-N,N,N-trimethylammonium chloride; DOTMA, N-(1-(2, 3-dioleyloxy)propyl)-N,N,N-trimethylammonium chloride; EPC, egg phosphatidylcholine; ESM, egg sphingomyelin; RT, room temperature; TBE, Tris-Borate-EDTA (89 mM in Tris-borate and 2 mM in EDTA); HEPES, 4-(2-hydroxyethyl)-1-piperazineethanesulfonic acid; HBS, HEPES buffered saline (150 mM NaCl and 20 mM HEPES); PEG-Cer-$C_{20}$, 1-O-(2'-(ω-methoxypolyethyleneglycol)succinoyl)-2-N-arachidoyl-sphingosine; PEG-Cer-$C_{14}$, 1-O-(2'-(ω-methoxypolyethyleneglycol)succinoyl)-2-N-myristoyl-sphingosine; PBS, phosphate-buffered saline; EGTA, ethylenebis(oxyethylenenitrilo)-tetraacetic acid; OGP, n-octyl β-D-glycopyranoside (Sigma Chemical Co., St. Louis, Mo.); POPC, palmitoyl oleoyl phosphatidylcholine (Northern Lipids, Vancouver, BC); QELS, quasielastic light scattering; TBE, 89 mM Tris-borate with 2 mM EDTA; and EDTA, Ethylenediaminetetraacetic acid (Fisher Scientific, Fair Lawn, N.J.).

The term "acyl" refers to a radical produced from an organic acid by removal of the hydroxyl group. Examples of acyl radicals include acetyl, pentanoyl, palmitoyl, stearoyl, myristoyl, caproyl and oleoyl.

As used herein, the term "pharmaceutically acceptable anion" refers to anions of organic and inorganic acids which provide non-toxic salts in pharmaceutical preparations. Examples of such anions include chloride, bromide, sulfate, phosphate, acetate, benzoate, citrate, glutamate, and lactate. The preparation of pharmaceutically acceptable salts is described in Berge, et al., J. Pharm. Sci. 66:1–19 (1977), incorporated herein by reference.

The term "lipid" refers to any fatty acid derivative which is capable of forming a bilayer such that a hydrophobic portion of the lipid material orients toward the bilayer while a hydrophilic portion orients toward the aqueous phase. Amphipathic lipids are necessary as the primary lipid vesicle structural element. Hydrophilic characteristics derive from the presence of phosphato, carboxylic, sulfato, amino, sulfhydryl, nitro, and other like groups. Hydrophobicity could be conferred by the inclusion of groups that include, but are not limited to, long chain saturated and unsaturated aliphatic hydrocarbon groups and such groups substituted by one or more aromatic, cycloaliphatic or heterocyclic group (s). Preferred lipids are phosphoglycerides and sphingolipids, representative examples of which include phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine or dilinoleoylphosphatidylcholine could be used. Other compounds lacking in phosphorus, such as sphingolipid and glycosphingolipid families are also within the group designated as lipid. Additionally, the amphipathic lipids described above may be mixed with other lipids including triglycerides and sterols.

The term "neutral" refers to any of a number of lipid species which exist either in an uncharged form, a neutral zwitterionic form. Such lipids include, for example diacylphosphatidylcholine, diacylphosphatidylethanolamine, ceramide, sphingomyelin, cephalin, and cerebrosides.

The term "non-cationic lipid" refers to any neutral lipid as described above as well as anionic lipids. Examples of anionic lipids include cardiolipin, diacylphosphatidylserine and diacylphosphatidic acid.

The term "cationic lipid" refers to any of a number of lipid species which carry a net positive charge at physiological pH. Such lipids include, but are not limited to, DODAC, DOTMA, DDAB, DOTAP, DC-Chol and DMRIE. Additionally, a number of commercial preparations of cationic lipids are available which can be used in the present invention. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic lipids comprising DOGS from Promega Corp., Madison, Wis., USA).

The term "nucleic acid" refers to a deoxyribonucleotide or ribonucleotide polymer in either single- or double-stranded form. Unless otherwise specified, the term nucleic acid is used interchangeably with gene, DNA, cDNA, RNA, and mRNA. The term specifically encompasses ribozymes; nucleic acid cloning and/ or expression vectors such as plasmids; genetically engineered viral genomes, expression cassettes, and chromosomes from mammalian (especially human) sources.

The terms "gene transfer", "transfection", and "transformation" are used herein interchangeably, and refer to the introduction of polyanionic materials, particularly nucleic acids, into cells. The term "lipofection" refers to the introduction of such materials using lipid-based complexes. The polyanionic materials can be in the form of DNA or RNA which is linked to expression vectors to facilitate gene expression after entry into the cell. Thus the polyanionic material used in the present invention is meant to include DNA having coding sequences for structural proteins, receptors and hormones, as well as transcriptional and translational regulatory elements (i.e., promoters, enhancers, terminators and signal sequences) and vectors. Methods of incorporating particular nucleic acids into expression vectors are well known to those of skill in the art, but are described in detail in, for example, Sambrook et al., *Molecular Cloning. A Laboratory Manual* (2nd ed.), Vols. 1–3, Cold Spring Harbor Laboratory, (1989) or *Current Protocols in Molecular Biology*, F. Ausubel et al., ed. Greene Publishing and Wiley-Interscience, New York (1987), both of which are incorporated herein by reference.

"Expression vectors", "cloning vectors", or "vectors" are nucleic acid molecules (such as plasmids) that are able to replicate in a chosen host cell. Expression vectors may replicate autonomously, or they may replicate by being inserted into the genome of the host cell, by methods well known in the art. Vectors that replicate autonomously will have an origin of replication or autonomous replicating sequence (ARS) that is functional in the chosen host cell(s). Often, it is desirable for a vector to be usable in more than one host cell, e.g., in *E. coli* for cloning and construction, and in a mammalian cell for expression.

The term "hydrophobic" as applied to DNA and DNA complexes, refers to complexes which are substantially more soluble in organic solvents than in aqueous solutions. More particularly, hydrophobic DNA and DNA complexes are those which are at least 50% soluble in organic solvents such as chloroform/methanol mixtures, and preferably more than 70% soluble, more preferably more than 90% soluble in such organic solvents.

II. General

Gene transfer techniques that involve the use of liposomes have been described previously in the art (U.S. Pat. Nos. 5,049,386; 4,946,787; and 4,897,355). General lipofection protocols are also described in the following references: Behr et al. (1989) *Proc. Natl. Acad. Sci. (U.S.A.)* 86: 6982; Demeneix et al. (1991) *Int. J. Dev. Biol.* 35: 481; Loeffler et al. (1990) *J. Neurochem.* 54; 1812; Bennett et al. (1992) *Mol. Pharmacol.* 41: 1023; Bertling et al. (1991) *Biotechnol. Appl. Biochem.* 13: 390; Felgner et al. (1987) *Proc. Natl. Acad. Sci. (U.S.A.)* 84: 7413; Felgner and Ringold (1989) *Nature* 337: 387; Gareis et al. (1991) *Cell. Mol. Biol.* 37: 191; Jarnagin et al. (1992) *Nucleic Acids Res.* 20: 4205; Jiao et al. (1992) *Exp. Neurol.* 115: 400; Lim et al. (1991) *Circulation* 83: 2007; Malone et al. (1989) *Proc. Natl. Acad. Sci. (U.S.A.)* 86: 6077; Powell et al. (1992) *Eur. J. Vasc. Surg.* 6: 130; Strauss and Jaenisch (1992) *EMBO J.* 11: 417; and Leventis and Silvius (1990) *Biochim. Biophys. Acta* 1023: 124. Lipofection reagents are sold commercially (e.g., "Transfectam" and "Lipofectin"). Cationic and neutral lipids that are reportedly suitable for efficient lipofection of nucleic acids include those of Felgner (WO91/17424; WO91/16024). In addition, a combination of neutral and cationic lipid has been shown to be highly efficient at lipofection of animal cells and showed a broad spectrum of effectiveness in a variety of cell lines (Rose et al. (1991) *BioTechniques* 10: 520. The above lipofection protocols may be adapted for use in the present invention, and the preceding references are therefore incorporated in their entirety.

III. Embodiments of the Invention

A. Lipid-Nucleic Acid Particles, and Properties Thereof

In one aspect, the present invention provides novel, lipid-nucleic acid complexes consisting essentially of cationic lipids and nucleic acids.

1. Lipid Components

Various suitable cationic lipids may be used in the present invention, either alone or in combination with one or more other cationic lipid species or neutral lipid species.

Cationic lipids which are useful in the present invention can be any of a number of lipid species which carry a net positive charge at physiological pH, for example: DODAC, DOTMA, DDAB, DOTAP, DOSPA, DOGS, DC-Chol and DMRIE, or combinations thereof. A number of these lipids and related analogs, which are also useful in the present invention, have been described in co-pending U.S. Ser. No. 08/316,399; U.S. Pat. Nos. 5,208,036, 5,264,618, 5,279,833 and 5,283,185, the disclosures of which are incorporated herein by reference. Additionally, a number of commercial preparations of cationic lipids are available and can be used in the present invention. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic liposomes comprising DOGS from Promega Corp., Madison, Wis., USA).

The non-cationic lipids used in the present invention can be any of a variety of neutral uncharged, zwitterionic or anionic lipids capable of producing a stable complex. They are preferably neutral, although they can alternatively be positively or negatively charged. Examples of non-cationic lipids useful in the present invention include: phospholipid-related materials, such as lecithin, phosphatidylethanolamine, lysolecithin, lysophosphatidylethanolamine, phosphatidylserine, phosphatidylinositol, sphingomyelin, cephalin, cardiolipin, phosphatidic acid, cerebrosides, dicetylphosphate, dioleoylphosphatidylcholine (DOPC), dipalmitoyl-phosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoy-lphosphatidylcholine (POPC), palmitoyloleoyl- phosphatidylethanolamine (POPE) and dioleoyl-phosphatidylethanolamine 4-(N-maleimidomethyl)-cyclohexane-1-carboxylate (DOPE-mal). Additional non-phosphorous containing lipids are, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide and the like, diacylphosphatidylcholine, diacylphosphatidylethanolamine, ceramide, sphingomyelin, cephalin, and cerebrosides. Other lipids such as lysophosphatidylcholine and lysophosphatidylethanolamine may be present. Non-cationic lipids also include polyethylene glycol-based polymers such as PEG 2000, PEG 5000 and polyethylene glycol conjugated to phospholipids or to ceramides (referred to as PEG-Cer), as described in co-pending U.S. Ser. No. 08/316,429, incorporated herein by reference.

In preferred embodiments, the non-cationic lipids are diacylphosphatidylcholine (e.g., dioleoylphosphatidylcholine, dipalmitoylphosphatidylcholine and dilinoleoylphosphatidylcholine), diacylphosphatidylethanolamine (e.g., dioleoylphosphatidylethanolamine and palmitoyloleoylphosphatidylethanolamine), ceramide or sphingomyelin. The acyl groups in these lipids are preferably acyl groups derived from fatty acids having $C_{10}$–$C_{24}$ carbon chains. More preferably the acyl groups are lauroyl, myristoyl, palmitoyl, stearoyl or oleoyl. In particularly preferred embodiments, the non-cationic lipid will be 1,2-sn-dioleoylphosphatidylethanolamine, or egg sphingomyelin (ESM).

2. Nucleic Acid Components

While the invention is described in the examples with reference to the use of plasmids, one of skill in the art will understand that the methods described herein are equally applicable to other larger nucleic acids or oligonucleotides.

The nucleic acids which are useful in the present invention (including both the complexes and particles) are typically nucleotide polymers having from 10 to 100,000 nucleotide residues. Typically, the nucleic acids are to be administered to a subject for the purpose of repairing or enhancing the expression of a cellular protein. Additionally, the nucleic acid can carry a label (e.g., radioactive label, fluorescent label or colorimetric label) for the purpose of providing clinical diagnosis relating to the presence or absence of complementary nucleic acids. Accordingly, the nucleic acids, or nucleotide polymers, can be polymers of nucleic acids including genomic DNA, cDNA, mRNA or oligonucleotides containing nucleic acid analogs, for example, the antisense derivatives described in a review by Stein, et al. Science 261:1004–1011 (1993) and in U.S. Pat. Nos. 5,264,423 and 5,276,019, the disclosures of which are incorporated herein by reference. Still further, the nucleic acids may encode transcriptional and translational regulatory sequences including promoter sequences and enhancer sequences.

The nucleotide polymers can be single-stranded DNA or RNA, or double-stranded DNA or DNA-RNA hybrids. Examples of double-stranded DNA include structural genes, genes including control and termination regions, and self-replicating systems such as plasmid DNA.

Single-stranded nucleic acids include antisense oligonucleotides (complementary to DNA and RNA), ribozymes and triplex-forming oligonucleotides. In order to increase stability, some single-stranded nucleic acids will preferably have some or all of the nucleotide linkages substituted with stable, non-phosphodiester linkages, including, for example, phosphorothioate, phosphorodithioate, phosphoroselenate, or O-alkyl phosphotriester linkages.

The nucleic acids used in the present invention will also include those nucleic acids in which modifications have been made in one or more sugar moieties and/or in one or more of the pyrimidine or purine bases. Examples of sugar modifications include replacement of one or more hydroxyl groups with halogens, alkyl groups, amines, azido groups or functionalized as ethers or esters. Additionally, the entire sugar may be replaced with sterically and electronically similar structures, including aza-sugars and carbocyclic sugar analogs. Modifications in the purine or pyrimidine base moiety include, for example, alkylated purines and pyrimidines, acylated purines or pyrimidines, or other heterocyclic substitutes known to those of skill in the art.

Multiple genetic sequences can be also be used in the present methods. Thus, the sequences for different proteins may be located on one strand or plasmid. Non-encoding sequences may be also be present, to the extent that they are necessary to achieve appropriate expression.

The nucleic acids used in the present method can be isolated from natural sources, obtained from such sources as ATCC or GenBank libraries or prepared by synthetic methods. Synthetic nucleic acids can be prepared by a variety of solution or solid phase methods. Generally, solid phase synthesis is preferred. Detailed descriptions of the procedures for solid phase synthesis of nucleic acids by phosphite-triester, phosphotriester, and H-phosphonate chemistries are widely available. See, for example, Itakura, U.S. Pat. No. 4,401,796; Caruthers, et al., U.S. Pat. Nos. 4,458.066 and 4,500,707; Beaucage, et al., Tetrahedron Lett., 22:1859–1862 (1981); Matteucci, et al., J. Am. Chem. Soc., 103:3185–3191 (1981); Caruthers, et al., Genetic Engineering, 4:1–17 (1982); Jones, chapter 2, Atkinson, et al., chapter 3, and Sproat, et al., chapter 4, in *Oligonucleotide Synthesis: A Practical Approach*, Gait (ed.), IRL Press, Washington D.C. (1984); Froehler, et al., Tetrahedron Lett., 27:469–472 (1986); Froehler, et al., Nucleic Acids Res., 14:5399–5407 (1986); Sinha, et al. Tetrahedron Lett., 24:5843–5846 (1983); and Sinha, et al., Nucl. Acids Res., 12:4539–4557 (1984) which are incorporated herein by reference.

a. Vectors for Introduction and Expression of Genes in Cells

An important aspect of this invention is the use of the lipid-nucleic acid particles provided herein to introduce selected genes into cells in vitro and in vivo, followed by expression of the selected gene in the host cell. Thus, the nucleic acids in the particles specifically encompass vectors that are capable of being expressed in a host cell. Promoter, enhancer, stress or chemically-regulated promoters, antibiotic-sensitive or nutrient-sensitive regions, as well as therapeutic protein encoding sequences, may be included as required.

In brief summary, the expression of natural or synthetic nucleic acids is typically achieved by operably linking a nucleic acid of interest to a promoter (which is either constitutive or inducible), incorporating the construct into an expression vector, and introducing the vector into a suitable host cell. Typical vectors contain transcription and translation terminators, transcription and translation initiation sequences, and promoters useful for regulation of the expression of the particular nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman and Smith (1979), *Gene,* 8: 81–97; Roberts et al. (1987), *Nature,* 328: 731–734; Berger and Kimmel, *Guide to Molecular Cloning Techniques, Methods in Enzymology,* volume 152, Academic Press, Inc., San Diego, Calif. (Berger); Sambrook et al. (1989), MOLECULAR CLONING—A LABORATORY MANUAL (2nd ed.) Vol. 1–3, Cold Spring Harbor Laboratory, Cold Spring Harbor Press, N.Y., (Sambrook); and F. M. Ausubel et al., CURRENT PROTOCOLS IN MOLECULAR BIOLOGY, eds., Current Protocols. a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.), as well as many other commercial sources known to one of skill.

Vectors to which foreign nucleic acids are operably linked may be used to introduce these nucleic acids into host cells and mediate their replication and/or expression. "Cloning vectors" are useful for replicating and amplifying the foreign nucleic acids and obtaining clones of specific foreign nucleic acid-containing vectors. "Expression vectors" mediate the expression of the foreign nucleic acid. Some vectors are both cloning and expression vectors.

In general, the particular vector used to transport a foreign gene into the cell is not particularly critical. Any of the conventional vectors used for expression in the chosen host cell may be used.

An expression vector typically comprises a eukaryotic transcription unit or "expression cassette" that contains all the elements required for the expression of exogenous genes in eukaryotic cells. A typical expression cassette contains a promoter operably linked to the DNA sequence encoding a desired protein and signals required for efficient polyadenylation of the transcript.

Eukaryotic promoters typically contain two types of recognition sequences, the TATA box and upstream promoter elements. The TATA box, located 25–30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus, the long term repeat from various retroviruses such as murine leukemia virus, murine or Rous sarcoma virus and HIV. See, *Enhancers and Eukaryotic Expression,* Cold Spring Harbor Press, Cold Spring Harbor, N.Y. 1983, which is incorporated herein by reference.

In addition to a promoter sequence, the expression cassette should also contain a transcription termination region downstream of the structural gene to provide for efficient termination. The termination region may be obtained from the same source as the promoter sequence or may be obtained from a different source.

If the mRNA encoded by the selected structural gene is to be efficiently translated, polyadenylation sequences are also commonly added to the vector construct. Two distinct sequence elements are required for accurate and efficient polyadenylation: GU or U rich sequences located downstream from the polyadenylation site and a highly conserved sequence of six nucleotides, AAUAAA, located 11–30 nucleotides upstream. Termination and polyadenylation signals that are suitable for the present invention include those derived from SV40, or a partial genomic copy of a gene already resident on the expression vector.

In addition to the elements already described, the expression vector of the present invention-may typically contain other specialized elements intended to increase the level of expression of cloned nucleic acids or to facilitate the identification of cells that carry the transduced DNA. For instance, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The expression vectors of the present invention will typically contain both prokaryotic sequences that facilitate the cloning of the vector in bacteria as well as one or more eukaryotic transcription units that are expressed only in eukaryotic cells, such as mammalian cells. The prokaryotic sequences are preferably chosen such that they do not interfere with the replication of the DNA in eukaryotic cells.

Selected genes are normally be expressed when the DNA sequence is functionally inserted into a vector. "Functionally inserted" means that it is inserted in proper reading frame and orientation and operably linked to proper regulatory elements. Typically, a gene will be inserted downstream from a promoter and will be followed by a stop codon, although production as a hybrid protein followed by cleavage may be used, if desired.

Expression vectors containing regulatory elements from eukaryotic viruses such as retroviruses are typically used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pA V009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

While a variety of vectors may be used, it should be noted that viral vectors such as retroviral vectors are useful for modifying eukaryotic cells because of the high efficiency with which the retroviral vectors transfect target cells and integrate into the target cell genome. Additionally, the retroviruses harboring the retroviral vector are capable of infecting cells from a wide variety of tissues.

In addition to the retroviral vectors mentioned above, cells may be lipofected with adeno-associated viral vectors. See, e.g., *Methods in Enzymology,* Vol. 185, Academic Press, Inc., San Diego, Calif. (D. V. Goeddel, ed.) (1990) or M. Krieger (1990), *Gene Transfer and Expression—A Laboratory Manual,* Stockton Press, New York, N.Y., and the references cited therein. Adeno associated viruses (AAVS) require helper viruses such as adenovirus or herpes virus to achieve productive infection. In the absence of helper virus functions, AAV integrates (site-specifically) into a host cell's genome, but the integrated AAV genome has no pathogenic effect. The integration step allows the AAV genome to remain genetically intact until the host is exposed to the appropriate environmental conditions (e.g., a lytic helper virus), whereupon it re-enters the lytic life-cycle. Samulski (1993), *Current Opinion in Genetic and Development,* 3: 74–80, and the references cited therein provides an overview of the AAV life cycle. See also West et al. (1987), *Virology,* 160: 38–47; Carter et al. (1989), U.S. Pat. No. 4,797,368; Carter et al. (1993), WO 93/24641; Kotin (1994), *Human Gene Therapy,* 5: 793–801; Muzyczka (1994), *J. Clin. Invest.,* 94: 1351 and Samulski, supra, for an overview of AAV vectors.

Plasmids designed for producing recombinant vaccinia, such as pGS62, (Langford, C. L. et al. (1986), *Mol. Cell. Biol.,* 6: 3191–3199) may also be used. This plasmid consists of a cloning site for insertion of foreign nucleic acids, the P7.5 promoter of vaccinia to direct synthesis of the inserted nucleic acid, and the vaccinia TK gene flanking both ends of the foreign nucleic acid.

Whatever the vector is used, generally the vector is genetically engineered to contain, in expressible form, a gene of interest. The particular gene selected will depend on the intended treatment. Examples of such genes of interest are described below at Section D.3. Insertion of Functional Copy of a Gene, and throughout the specification.

The vectors further usually comprise selectable markers which result in nucleic acid amplification such as the sodium, potassium ATPase, thymidine kinase, aminoglycoside phosphotransferase, hygromycin B phosphotransferase, xanthine-guanine phosphoribosyl transferase, CAD (carbamyl phosphate synthetase, aspartate transcarbamylase, and dihydroorotase), adenosine deaminase, dihydrofolate reductase, and asparagine synthetase and ouabain selection. Alternatively, high yield expression systems not involving nucleic acid amplification are also suitable, such as using a bacculovirus vector in insect cells, with the encoding sequence under the direction of the polyhedrin promoter or other strong baculovirus promoters.

When nucleic acids other than plasmids are used the nucleic acids can contain nucleic acid analogs, for example, the antisense derivatives described in a review by Stein, et al., Science 261:1004–1011 (1993) and in U.S. Pat. Nos. 5,264,423 and 5,276,019, the disclosures of which are incorporated herein by reference.

B. Methods of Making the Particles

In one embodiment, the present invention provides lipid-nucleic acid particles produced via novel, hydrophobic nucleic acid-lipid intermediate complexes. The complexes are preferably charge-neutralized. Manipulation of these complexes in either detergent-based or organic solvent-based systems can lead to particle formation in which the nucleic acid is protected.

Figure 2:
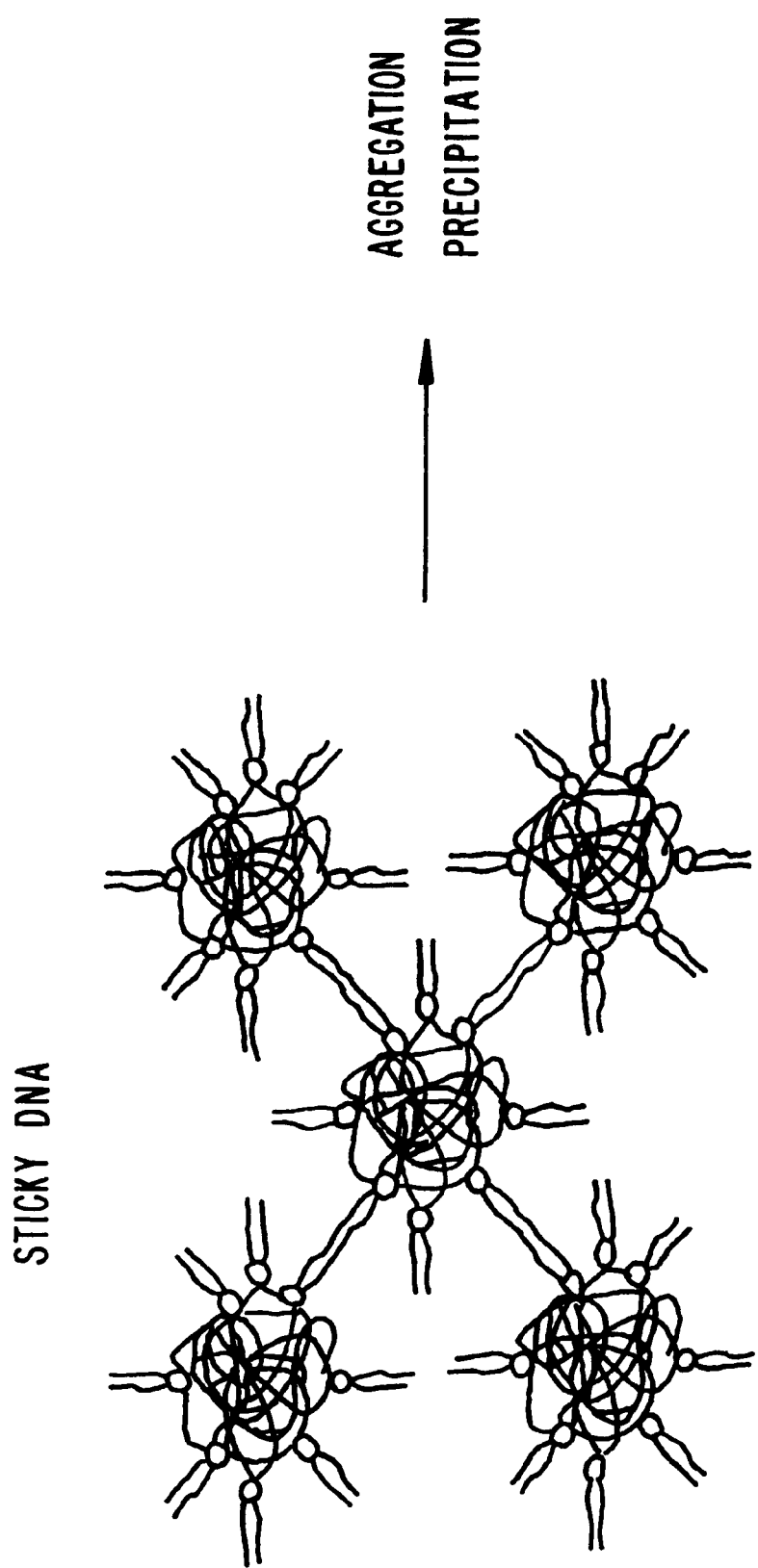
FIG. 2 illustrates an aggregation and precipitation which commonly occurs during the entrapment of large nucleic acids in lipid complexes.

Lipid-nucleic acid formulations can be formed by combining the nucleic acid with a preformed cationic liposome (see, U.S. Pat. Nos. 4,897,355, 5,264,618, 5,279,833 and 5,283,185). In such methods, the nucleic acid is attracted to the cationic surface charge of the liposome and the resulting complexes are thought to be of the liposome-covered "sandwich-type." As a result, a portion of the nucleic acid or plasmid remains exposed in serum and can be degraded by enzymes such as DNAse I. Others have attempted to incorporate the nucleic acid or plasmid into the interior of a liposome during formation. These methods typically result in the aggregation in solution of the cationic lipid-nucleic acid complexes (see FIG. 2). Passive loading of a plasmid into a preformed liposome has also not proven successful. Finally, the liposome-plasmid complexes which have been formed are typically 200 to 400 nm in size and are therefore cleared more rapidly from circulation than smaller sized complexes or particles.

The present invention provides a method of preparing serum-stable plasmid-lipid particles in which the plasmid is encapsulated in a lipid-bilayer and is protected from degradation. Additionally, the particles formed in the present invention are preferably neutral or negatively-charged at physiological pH. For in vivo applications, neutral particles are advantageous, while for in vitro applications the particles are more preferably negatively charged. This provides the further advantage of reduced aggregation over the positively-charged liposome formulations in which a nucleic acid can be encapsulated in cationic lipids.

Figure 3:
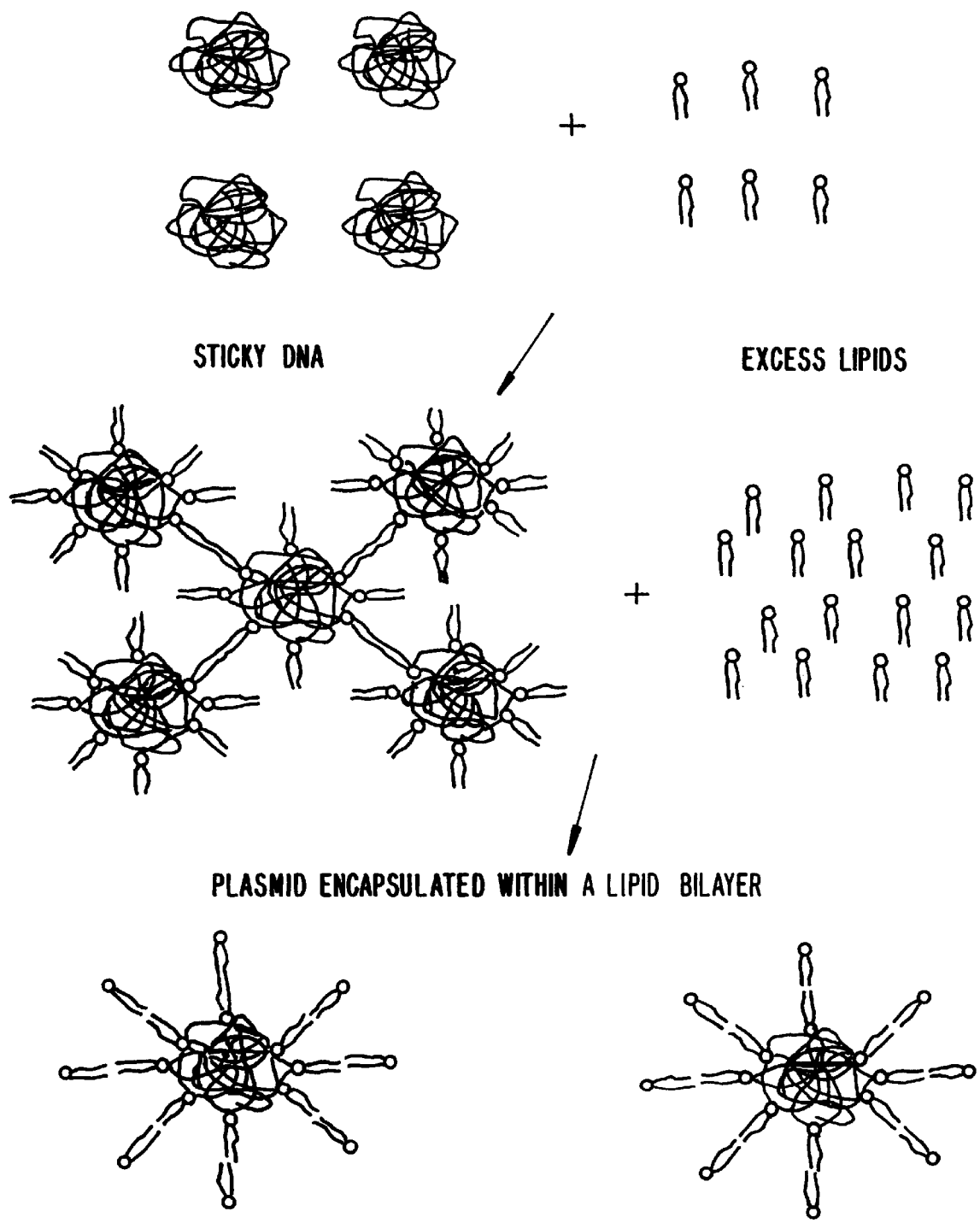
FIG. 3 provides a schematic representation of the preparation of plasmid-lipid particles according to certain embodiments of the present invention.

The particles made by the methods of this invention have a size of about 50 to about 150 nm, with a majority of the particles being about 65 to 85 nm. The particles can be formed by either a detergent dialysis method or by a modification of a reverse-phase method which utilizes organic solvents to provide a single phase during mixing of the components. Without intending to be bound by any particular mechanism of formation, FIG. 3 depicts a detergent dialysis approach to the formation of the plasmid-lipid particles. With reference to FIG. 3, a plasmid or other large nucleic acid is contacted with a detergent solution of cationic lipids to form a coated plasmid complex. These coated plasmids can aggregate and precipitate. However, the presence of a detergent reduces this aggregation and allows the coated plasmids to react with excess lipids (typically, non-cationic lipids) to form particles in which the plasmid is encapsulated in a lipid bilayer. As noted above, these particles differ from the more classical liposomes both in size (liposomes being typically 200–400 nm) in that there is little or no aqueous medium encapsulated by the particle's lipid bilayer. The methods described below for the formation of plasmid-lipid particles using organic solvents follow a similar scheme.

In some embodiments, the particles are formed using detergent dialysis. Thus, the present invention provides a method for the preparation of serum-stable plasmid-lipid particles, comprising:

(a) combining a plasmid with cationic lipids in a detergent solution to form a coated plasmid-lipid complex;

(b) contacting non-cationic lipids with the coated plasmid-lipid complex to form a detergent solution comprising a plasmid-lipid complex and non-cationic lipids; and (c) dialyzing the detergent solution of step (b) to provide a solution of serum-stable plasmid-lipid particles, wherein the plasmid is encapsulated in a lipid bilayer and the particles are serum-stable and have a size of from about 50 to about 150 nm.

An initial solution of coated plasmid-lipid complexes is formed by combining the plasmid with the cationic lipids in a detergent solution.

In these embodiments, the detergent solution is preferably an aqueous solution of a neutral detergent having a critical micelle concentration of 15–300 mM, more preferably 20–50 mM. Examples of suitable detergents include, for example, N,N'-((octanoylimino)-bis-(trimethylene))-bis-(D-gluconamide) (BIGCHAP); BRIJ 35; Deoxy-BIGCHAP; dodecylpoly(ethylene glycol) ether; Tween 20; Tween 40; Tween 60; Tween 80; Tween 85; Mega 8; Mega 9; Zwittergent® 3–08; Zwittergent® 3–10; Triton X-405; hexyl-, heptyl-, octyl- and nonyl-β-D-glucopyranoside; and heptylthioglucopyranoside; with octyl β-D-glucopyranoside and Tween-20 being the most preferred. The concentration of detergent in the detergent solution is typically about 100 mM to about 2 M, preferably from about 200 mM to about 1.5 M.

The cationic lipids and plasmid will typically be combined to produce a charge ratio (+/−) of about 1:1 to about 20:1, preferably in a ratio of about 1:1 to about 12:1, and more preferably in a ratio of about 2:1 to about 6:1. Additionally, the overall concentration of plasmid in solution will typically be from about 25 µg/mL to about 1 mg/mL, preferably from about 25 µg/mL to about 200 µg/mL, and more preferably from about 50 µg/mL to about 100 µg/mL. The combination of plasmids and cationic lipids in detergent solution is kept, typically at room temperature, for a period of time which is sufficient for the coated complexes to form. Alternatively, the plasmids and cationic lipids can be combined in the detergent solution and warmed to temperatures of up to about 37° C. For plasmids which are particularly sensitive to temperature, the coated complexes can be formed at lower temperatures, typically down to about 4° C.

The detergent solution of the coated plasmid-lipid complexes is then contacted with non-cationic lipids to provide a detergent solution of plasmid-lipid complexes and non-cationic lipids. The non-cationic lipids which are useful in this step include, diacylphosphatidylcholine, diacylphosphatidylethanolamine, ceramide, sphingomyelin, cephalin, cardiolipin, and cerebrosides. In preferred embodiments, the non-cationic lipids are diacylphosphatidylcholine, diacylphosphatidylethanolamine, ceramide or sphingomyelin. The acyl groups in these lipids are preferably acyl groups derived from fatty acids having $C_{10}$–$C_{24}$ carbon chains. More preferably the acyl groups are lauroyl, myristoyl, palmitoyl, stearoyl or oleoyl. In particularly preferred embodiments, the non-cationic lipid will be 1,2-sn-dioleoylphosphatidylethanolamine (DOPE), palmitoyl oleoyl phosphatidylcholine (POPC) or egg phosphatidylcholine (EPC). In the most preferred embodiments, the plasmid-lipid particles will be fusogenic particles with enhanced properties in vivo and the non-cationic lipid will be DOPE. In other preferred embodiments, the non-cationic lipids will further comprise polyethylene glycol-based polymers such as PEG 2000, PEG 5000 and polyethylene glycol conjugated to ceramides, as described in co-pending U.S. Ser. No. 08/316,429, incorporated herein by reference.

The amount of non-cationic lipid which is used in the present methods is typically about 2 to about 20 mg of total lipids to 50 µg of plasmid. Preferably the amount of total lipid is from about 5 to about 10 mg per 50 µg of plasmid.

Following formation of the detergent solution of plasmid-lipid complexes and non-cationic lipids, the detergent is removed, preferably by dialysis. The removal of the detergent results in the formation of a lipid-bilayer which surrounds the plasmid providing serum-stable plasmid-lipid particles which have a size of from about 50 nm to about 150 nm. The particles thus formed do not aggregate and are optionally sized to achieve a uniform particle size.

The serum-stable plasmid-lipid particles can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles is described in U.S. Pat. No. 4,737,323, incorporated herein by reference. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In another group of embodiments, the present invention provides a method for the preparation of serum-stable plasmid-lipid particles, comprising;

(a) preparing a mixture comprising cationic lipids and non-cationic lipids in an organic solvent;

(b) contacting an aqueous solution of nucleic acid with said mixture in step (a) to provide a clear single phase; and (c) removing said organic solvent to provide a suspension of plasmid-lipid particles, wherein said plasmid is encapsulated in a lipid bilayer, and said particles are stable in serum and have a size of from about 50 to about 150 nm.

The plasmids (or nucleic acids), cationic lipids and non-cationic lipids which are useful in this group of embodiments are as described for the detergent dialysis methods above.

The selection of an organic solvent will typically involve consideration of solvent polarity and the ease with which the solvent can be removed at the later stages of particle formation. The organic solvent, which is also used as a solubilizing agent, is in an amount sufficient to provide a clear single phase mixture of plasmid and lipids. Suitable solvents include chloroform, dichloromethane, diethylether, cyclohexane, cyclopentane, benzene, toluene, methanol, or other aliphatic alcohols such as propanol, isopropanol, butanol, tert-butanol, iso-butanol, pentanol and hexanol. Combinations of two or more solvents may also be used in the present invention.

Contacting the plasmid with the organic solution of cationic and non-cationic lipids is accomplished by mixing together a first solution of plasmid, which is typically an aqueous solution and a second organic solution of the lipids. One of skill in the art will understand that this mixing can take place by any number of methods, for example by mechanical means such as by using vortex mixers.

After the plasmid has been contacted with the organic solution of lipids, the organic solvent is removed, thus forming an aqueous suspension of serum-stable plasmid-lipid particles. The methods used to remove the organic solvent will typically involve evaporation at reduced pressures or blowing a stream of inert gas (e.g., nitrogen or argon) across the mixture.

The serum-stable plasmid-lipid particles thus formed will typically be sized from about 50 nm to 150 nm. To achieve further size reduction or homogeneity of size in the particles, sizing can be conducted as described above.

In other embodiments, the methods will further comprise adding nonlipid polycations which are useful to effect the transformation of cells using the present compositions. Examples of suitable nonlipid polycations include, hexadimethrine bromide (sold under the brandname POLYBRENE®, from Aldrich Chemical Co., Milwaukee, Wis., USA) or other salts of heaxadimethrine. Other suitable polycations include, for example, salts of poly-L-ornithine, poly-L-arginine, poly-L-lysine, poly-D-lysine, polyallylamine and polyethyleneimine.

In other embodiments, the polyoxyethylene conjugates which are used in the plasmid-lipid particles of the present invention can be prepared by combining the conjugating group (i.e. phosphatidic acid or phosphatidylethanolamine) with an appropriately functionalized polyoxyethylene derivative. For example, phosphatidylethanolamine can be combined with polyoxyethylene bis(p-toluenesulfonate) to provide a phosphatidylethanolamine-polyoxyethylene conjugate. See, Woodle, et al., Biochim. Biophys. Acta 1105:193–200 (1992), incorporated herein by reference.

In certain embodiments, the formation of the lipid-nucleic acid complexes can be carried out either in a monophase system (e.g., a Bligh and Dyer monophase or similar mixture of aqueous and organic solvents) or in a two phase system with suitable mixing.

When formation of the complexes is carried out in a monophase system, the cationic lipids and nucleic acids are each dissolved in a volume of the monophase mixture. Combination of the two solutions provides a single mixture in which the complexes form. Alternatively, the complexes can form in two-phase mixtures in which the cationic lipids bind to the nucleic acid (which is present in the aqueous phase), and "pull" it in to the organic phase.

Without intending to be bound by any particular theory of formation, FIG. 1 provides a model for the binding of monocationic lipids to DNA which results in the formation of a hydrophobic (organic-soluble) lipid-nucleic acid complex. In this figure, cationic lipids first bind to the DNA to form a complex in which the DNA is uncondensed. This complex is soluble in the organic phase or in a monophase and the DNA remains uncondensed. Upon the addition of other lipids and removal of solvent, and hydration, the complexes form particles (described in more detail below).

In another embodiment, the present invention provides a method for the preparation of lipid-nucleic acid particles, comprising:

(a) contacting nucleic acids with a solution comprising non-cationic lipids and a detergent to form a nucleic acid-lipid mixture;

(b) contacting cationic lipids with the nucleic acid-lipid mixture to neutralize a portion of the negative charge of the nucleic acids and form a charge-neutralized mixture of nucleic acids and lipids; and (c) removing the detergent from the charge-neutralized mixture to provide the lipid-nucleic acid particles in which the nucleic acids are protected from degradation.

Figure 30:
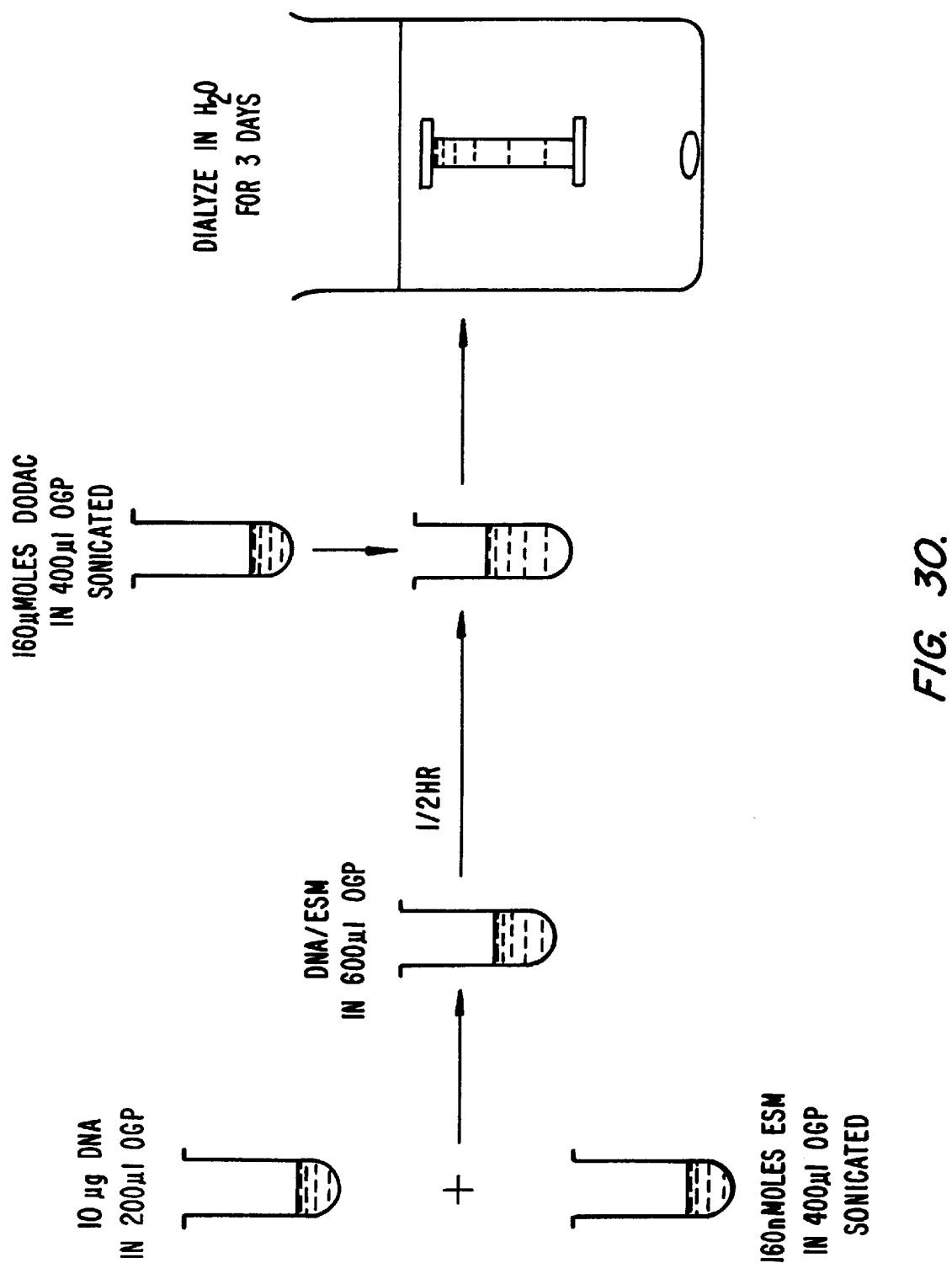
FIG. 30 illustrates a protocol for preparing lipid-nucleic acid particles using detergent dialysis.

Without intending to be limited by any particular aspect of the illustration, FIG. 30 provides a depiction of one method of forming the particles using detergent dialysis. In this figure, DNA in an aqueous detergent solution (OGP) is combined with non-cationic lipids (ESM) in an aqueous detergent solution and allowed to anneal for about 30 min. A previously sonicated mixture of cationic lipid (DODAC) in detergent is added and the resulting mixture is dialyzed for 3 days to remove detergent and thereby form lipid-nucleic acid particles. One of skill in the art will understand that for the kinetic formation of such particles, the order of addition of cationic lipids and non-cationic lipids could be reversed, or the lipids could be added simultaneously. In addition, it is possible to cover the nucleic acid with multivalent cations, such that it now binds anions.

In one group of embodiments, the solution of non-cationic lipids and detergent is an aqueous solution. Contacting the nucleic acids with the solution of non-cationic lipids and detergent is typically accomplished by mixing together a first-solution of nucleic acids and a second solution of the lipids and detergent. One of skill in the art will understand that this mixing can take place by any number of methods, for example by mechanical means such as by using vortex mixers. Preferably, the nucleic acid solution is also a detergent solution. The amount of non-cationic lipid which is used in the present method is typically determined based on the amount of cationic lipid used, and is typically of from about 0.2 to 5 times the amount of cationic lipid, preferably about 0.5 to 2 times the amount of cationic lipid used.

The nucleic acid-lipid mixture thus formed is contacted with cationic lipids to neutralize a portion of the negative charge which is associated with the nucleic acids (or other polyanionic materials) present. The amount of cationic lipids used will typically be sufficient to neutralize at least 50% of the negative charge of the nucleic acid. Preferably, the negative charge will be at least 70% neutralized, more preferably at least 90% neutralized. Cationic lipids which are useful in the present invention, include, for example, DODAC, DOTMA, DDAB, DOTAP, DC-Chol and DMRIE. These lipids and related analogs have been described in co-pending U.S. Ser. No. 08/316,399; U.S. Pat. Nos. 5,208,036, 5,264,618, 5,279,833 and 5,283,185, the disclosures of which are incorporated herein by reference. Additionally, a number of commercial preparations of cationic lipids are available and can be used in the present invention. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic lipids comprising DOGS in ethanol from Promega Corp., Madison, Wis., USA).

Contacting the cationic lipids with the nucleic acid-lipid mixture can be accomplished by any of a number of techniques, preferably by mixing together a solution of the cationic lipid and a solution containing the nucleic acid-lipid mixture. Upon mixing the two solutions (or contacting in any other manner), a portion of the negative charge associated with the nucleic acid is neutralized. Nevertheless, the nucleic acid remains in an uncondensed state and acquires hydrophilic characteristics.

After the cationic lipids have been contacted with the nucleic acid-lipid mixture, the detergent (or combination of detergent and organic solvent) is removed, thus forming the lipid-nucleic acid particles. The methods used to remove the detergent will typically involve dialysis. When organic solvents are present, removal is typically accomplished by evaporation at reduced pressures or by blowing a stream of inert gas (e.g., nitrogen or argon) across the mixture.

The particles thus formed will typically be sized from about 100 nm to several microns. To achieve further size reduction or homogeneity of size in the particles, the lipid-nucleic acid particles can be sonicated, filtered or subjected to other sizing techniques which are used in liposomal formulations and are known to those of skill in the art.

In other embodiments, the methods will further comprise adding nonlipid polycations which are useful to effect the lipofection of cells using the present compositions. Examples of suitable nonlipid polycations include, hexadimethrine bromide (sold under the brandname POLYBRENE®, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine and polyethyleneimine. Addition of these salts is preferably after the particles have been formed.

In another aspect, the present invention provides methods for the preparation of lipid-nucleic acid particles, comprising:

(a) contacting an amount of cationic lipids with nucleic acids in a solution; the solution comprising of from about 15–35% water and about 65–85% organic solvent and the amount of cationic lipids being sufficient to produce a +/− charge ratio of from about 0.85 to about 2.0, to provide a hydrophobic, charge-neutralized lipid-nucleic acid complex;

(b) contacting the hydrophobic, charge-neutralized lipid-nucleic acid complex in solution with non-cationic lipids, to provide a lipid-nucleic acid mixture; and (c) removing the organic solvents from the lipid-nucleic acid mixture to provide lipid-nucleic acid particles in which the nucleic acids are protected from degradation.

The nucleic acids, non-cationic lipids, cationic lipids and organic solvents which are useful in this aspect of the invention are the same as those described for the methods above which used detergents. In one group of embodiments, the solution of step (a) is a monophase. In another group of embodiments, the solution of step (a) is two-phase.

In preferred embodiments, the cationic lipids are DODAC, DDAB, DOTMA, DOSPA, DMRIE, DOGS or combinations thereof. In other preferred embodiments, the non-cationic lipids are ESM, DOPE, polyethylene glycol-based polymers (e.g., PEG 2000, PEG 5000, PEG-modified phospholipids or PEG-modified ceramides) or combinations thereof. In still other preferred embodiments, the organic solvents are methanol, chloroform, methylene chloride, ethanol, diethyl ether or combinations thereof.

In a particularly preferred embodiment, the nucleic acid is a plasmid; the cationic lipid is DODAC, DDAB, DOTMA, DOSPA, DMRIE, DOGS or combinations thereof; the non-cationic lipid is ESM, DOPE, polyethylene glycol-based polymers or combinations thereof; and the organic solvent is methanol, chloroform, methylene chloride, ethanol, diethyl ether or combinations thereof.

As above, contacting the nucleic acids with the cationic lipids is typically accomplished by mixing together a first solution of nucleic acids and a second solution of the lipids, preferably by mechanical means such as by using vortex mixers. The resulting mixture contains complexes as described for one aspect of the invention above. These complexes are then converted to particles by the addition of non-cationic lipids and the removal of the organic solvent. The addition of the non-cationic lipids is typically accomplished by simply adding a solution of the non-cationic lipids to the mixture containing the complexes. A reverse addition can also be used. Subsequent removal of organic solvents can be accomplished by methods known to those of skill in the art and also described above.

The amount of non-cationic lipids which is used in this aspect of the invention is typically an amount of from about 0.2 to 5 times the amount (on a mole basis) of cationic lipids which was used to provide the charge-neutralized lipid-nucleic acid complex. Preferably, the amount is from 0.5 to 2 times the amount of cationic lipids used.

In yet another aspect, the present invention provides lipid-nucleic acid particles which are prepared by the methods described above. In these embodiments, the lipid-nucleic acid particles are either net charge neutral or carry an overall charge which provides the particles with greater gene lipofection activity. Preferably, the nucleic acid component of the particles is a nucleic acid which encodes a desired protein or blocks the production of an undesired protein. In particularly preferred embodiments, the nucleic acid is a plasmid, the non-cationic lipid is egg sphingomyelin and the cationic lipid is DODAC.

As noted above, the lipid-nucleic acid particles are useful for the lipofection of cells, either in vitro or in vivo. Accordingly, the present invention provides, in yet another aspect, a method for introducing a nucleic acid into a cell, comprising;

(a) preparing a lipid-nucleic acid particle according to the methods above; and (b) contacting the cell with the lipid-nucleic acid particle for a period of time sufficient to introduce the nucleic acid into the cell.

Although discussed in more detail below, preferred embodiments are those in which the lipid-nucleic acid particle comprises a plasmid, DODAC and ESM.

Unlike viral-based gene therapy vectors which can only incorporate a relatively small non-viral nucleic acid sequence into the viral genome because of size limitations for packaging virion particles, the lipid-nucleic acid complexes of the present invention may be used to transfer large (e.g., 50–5,000 kilobase) exogenous nucleic acids into cells. This aspect of lipofection is particularly advantageous since many genes which may be targets for gene therapy span over 100 kilobases (e.g., amyloid precursor protein (APP) gene, Huntington's chorea gene) and large homologous targeting constructs or transgenes may be required for therapy.

Cells can be lipofected with an exogenous nucleic acid at high efficiency and with cell type specificity by contacting the cells with a receptor-recognition transfection complex comprising: (1) an exogenous nucleic acid, (2) a receptor-ligand protein ("rlp" which is covalently linked to a polycation, and (3) a cationic or neutral lipid. It has been found that a combination of a polycation-linked receptor-recognition protein and a suitable cationic (or neutral) lipid can be used to transfect nucleic acids, and that the combination retains cell type targeting specificity conferred by the receptor-recognition protein and also exhibits high efficiency transfection conferred, in part, by the inclusion of a cationic lipid, neutral lipid, or lipopolyamine.

The exogenous nucleic acid is typically dsDNA, ssDNA, ssRNA, dsRNA; most typically the exogenous nucleic acid is dsDNA such as a cloned DNA sequence in a cloning vector such as a plasmid or viral genome. Multiple species of exogenous nucleic acid may be combined in a transfection complex, such as for co-transfection of unlinked nucleic acid sequences or to accomplish in vivo homologous recombination shuffling. Frequently, the exogenous nucleic acid(s) are not capable of autonomous replication in cells which incorporate the transfection complex, and are either transiently expressed or are stably integrated into a host cell chromosome by homologous recombination or nonhomologous integration. Often at least one selectable marker (e.g., a neo$^R$ expression cassette) is included in the exogenous nucleic acid(s) to facilitate selection of cells which have incorporated the exogenous nucleic acid(s). Typically, an exogenous nucleic acid comprises a structural gene encoding a polypeptide to be expressed in a target cell which has incorporated the exogenous nucleic acid, and the structural gene usually is operably linked to appropriate cis-acting regulatory elements (e.g., promoter, enhancer, polyadenylation site). Although gene therapy may be performed in a variety of ways, a typical receptor-recognition lipofection complex comprises a nucleic acid which comprises at least one transcriptional unit.

The lipid nucleic acid particles of the invention can be designed to contain, in addition to the species of nucleic acid, a receptor-recognition molecule (rlm), such as a protein. The rlm can be covalently bound to lipids that comprise the nucleic acid-lipid particle. Its presence on the particle increases the efficiency aand specificity with the particle contacts and enters target cells. For example, a suitable rlm is a non-immunoglobulin protein that binds to a cell surface receptor of a target cell which mediates internalization of a transfection complex comprising the rlm-polycation conjugate by, for example, the process of endocytosis and/or membrane fusion. Additional suitable rlm species typically are naturally-occurring physiological ligands which comprise a polypeptide portion (e.g., adhesion molecules such as ICAM-1, ICAM-2, ELAM-1, VCAM-1). Viral proteins (e.g., spike glycoproteins) which bind to viral receptors on eukaryotic cells and mediate virus internalization may also be used as rlm species for forming rlm-polycation conjugates. Examples also include viral glycoproteins which attach to cell surface receptors and lead to internalization and/or membrane fusion include the gB, gC, gD, gE, gH, and gI virion glycoproteins of HSV-1, and gp120 of HIV-1.

Fragments and analogs of naturally-occurring proteins may be used as well as full-length mature proteins as rlm species in forming transfection complexes of the invention. For example, fragments, analogs, and fusion proteins comprising a portion of an adhesion molecule or virion attachment protein which mediates attachment to a target cell may be used as rlm species without other portions of the naturally-occurring full-length protein that are not essential for cell attachment and/or membrane fusion. Thus, for example, a cytoplasmic tail peptide portion of a virion glycoprotein usually may be omitted and the resultant protein may still serve as a suitable rlm.

The rlm selected will vary with the particular target cell type. For specific targeting to hepatocytes, asialoglycoproteins (galactose-terminal) are preferred as rlm species. Examples of asialoglycoproteins include asialoorosomucoid, asialofetuin, and desialylated vesicular stomatitis virus virion proteins. These can be formed by chemical or enzymatic desialylation of those glycoproteins that possess terminal sialic acid and penultimate galactose residues. Alternatively, rlm species suitable for forming lipofection complexes that selectively target hepatocytes may be created by coupling lactose or other galactose-terminal carbohydrates (e.g., arabinogalactan) to non-galactose-bearing proteins by reductive lactosamination. Other useful galactose-terminal carbohydrates for hepatocyte targeting include carbohydrate trees obtained from natural glycoproteins, especially tri- and tetra-antennary structures that contain either terminal galactose residues or that can be enzymatically treated to expose terminal galactose residues. For targeting macrophages, endothelial cells, or lymphocytes, rlm species comprising mannose or mannose-6-phosphate, or complex carbohydrates comprising these terminal carbohydrate structures may be used.

Since a variety of different cell surface receptors exist on the surfaces of mammalian cells, cell-specific targeting of nucleic acids to nonhepatic cells can involve lipofection complexes that comprise various rlm species. For example, transferrin can be used as a suitable rlm for forming receptor-recognition transfection complexes to cells expressing transferrin receptors. Other receptor ligands such as polypeptide hormones (e.g., growth hormone, PDGF, FGF, EGF, insulin, IL-2, IL-4, etc.) may be used to localize receptor-recognition transfection complexes to cells expressing the cognate receptor.

The nucleic acid-lipid particles may comprise multiple rlm species. Frequently, an agent having membrane fusion activity (e.g., influenza virus hemagglutinin, HSV-1 gB and gD) is used as an rlm for forming rlm-polycation complexes, either alone or in combination with other rlm species, typically with those which lack membrane fusion activity.

These transfection methods generally comprise the steps of: (1) forming a nucleic acid-lipid-rlm particle consisting essentially of an exogenous nucleic acid, a polycation conjugate consisting essentially of a polycation linked to a non-immunoglobulin receptor-recognition molecule that binds to a predetermined cell surface receptor, and a lipid component consisting essentially of a neutral or cationic lipid (optionally including a quaternary ammonium detergent and/or a lipopolyamine), and (2) contacting cells expressing the predetermined cell surface receptor with a composition comprising the receptor-recognition transfection complex under physiological transfection conditions which permit uptake of the exogenous nucleic acid into said cells. In alternative embodiments, the rlm is attached to the polycation by covalent linkage, frequently by covalent linkage through a crosslinking agent or by peptide linkage.

Overall particle charge is an important property of the particles, as it may affect particle clearance from the blood. Particles with prolonged circulation half-lives are typically desirable for therapeutic and diagnostic uses. For instance, particles which can be maintained from 8, 12, or up to 24 hours in the bloodstream are particularly preferred. Negatively charged liposomes and particles are typically, taken up more rapidly by the reticuloendothelial system (Juliano, *Biochem. Biophys. Res. Commun.* 63:651 (1975)) and thus have shorter half-lives in the bloodstream.

C. Pharmaceutical Preparations

The nucleic acid-lipid particles of the present invention can be administered either alone or in mixture with a physiologically-acceptable carrier (such as physiological saline or phosphate buffer) selected in accordance with the route of administration and standard pharmaceutical practice. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc.

The pharmaceutical carrier is generally added following particle formation. Thus, after the particle is formed, the particle can be diluted into pharmaceutically acceptable carriers such as normal saline.

The concentration of particles in the pharmaceutical formulations can vary widely, i.e., from less than about 0.05%, usually at or at least about 2–5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration. It is often desirable to include polyethylene glycol (PEG), PEG-ceramide, or modified (e.g., ganglioside $G_{M1}$-modified) lipids to the particles. Addition of such components prevents particle aggregation and provides a means for increasing circulation lifetime and increasing the delivery of the lipid-nucleic acid particles to the target tissues. Typically, the concentration of the PEG, PEG-ceramide or $G_{M1}$-modified lipids in the particle will be about 1–15%.

The pharmaceutical compositions may be sterilized by conventional, well known sterilization techniques. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

In another example of their use, lipid-nucleic acid particles can be incorporated into a broad range of topical dosage forms including but not limited to gels, oils, emulsions and the like. For instance, the suspension containing the nucleic acid-lipid particles can be formulated and administered as topical creams, pastes, ointments, gels, lotions and the like.

The present invention also provides lipid-nucleic acid particles in kit form. The kit will typically be comprised of a container which is compartmentalized for holding the various elements of the kit. The kit will contain the compositions of the present inventions, preferably in dehydrated form, with instructions for their rehydration and administration. In still other embodiments, the particles and/or compositions comprising the particles will have a targeting moiety attached to the surface of the particle. Methods of attaching targeting moieties (e.g., antibodies, proteins) to lipids (such as those used in the present particles) are known to those of skill in the art.

D. Administration of Lipid-Nucleic Acid Particle Formulations

The serum-stable nucleic acid-lipid particles of the present invention are useful for the introduction of nucleic acids into cells. Accordingly, the present invention also provides methods for introducing a nucleic acids (e.g., a plasmid) into a cell. The methods are carried out in vitro or in vivo by first forming the particles as described above, then contacting the particles with the cells for a period of time sufficient for transfection to occur.

The nucleic acid-lipid particles of the present invention can be adsorbed to almost any cell type with which they are mixed or contacted. Once adsorbed, the particles can either be endocytosed by a portion of the cells, exchange lipids with cell membranes, or fuse with the cells. Transfer or incorporation of the nucleic acid portion of the particle can take place via any one of these pathways. In particular, when fusion takes place, the particle membrane is integrated into the cell membrane and the contents of the particle combine with the intracellular fluid.

1. In vitro Gene Transfer

For in vitro applications, the delivery of nucleic acids can be to any cell grown in culture, whether of plant or animal origin, vertebrate or invertebrate, and of any tissue or type. In preferred embodiments, the cells will be animal cells, more preferably mammalian cells, and most preferably human cells.

Contact between the cells and the lipid-nucleic acid particles, when carried out in vitro, takes place in a biologically compatible medium. The concentration of particles varies widely depending on the particular application, but is generally between about 1 μmol and about 10 mmol. Treatment of the cells with the nucleic acid-lipid particles is generally carried out at physiological temperatures (about 37° C.) for periods of time of from about 1 to 48 hours, preferably of from about 2 to 4 hours.

In one group of preferred embodiments, a lipid-nucleic acid particle suspension is added to 60–80% confluent plated cells having a cell density of from about $10^3$ to about $10^5$ cells/mL, more preferably about $2 \times 10^4$ cells/mL. The concentration of the suspension added to the cells is preferably of from about 0.01 to 0.2 μg/mL, more preferably about 0.1 μg/mL.

2. In vivo Gene Transfer

Alternatively, the compositions of the present invention can also be used for the in vivo gene transfer, using methods which are known to those of skill in the art. In particular, Zhu, et al., Science 261:209–211 (1993), incorporated herein by reference, describes the intravenous delivery of cytomegalovirus (CMV)-chloramphenicol acetyltransferase (CAT) expression plasmid using DOTMA-DOPE complexes. Hyde, et al., Nature 362:250–256 (1993), incorporated herein by reference, describes the delivery of the cystic fibrosis transmembrane conductance regulator (CFTR) gene to epithelia of the airway and to alveoli in the lung of mice, using liposomes. Brigham, et al., Am. J. Med. Sci. 298:278–281 (1989), incorporated herein by reference, describes the in vivo transfection of lungs of mice with a functioning prokaryotic gene encoding the intracellular enzyme chloramphenicol acetyltransferase (CAT).

For in vivo administration, the pharmaceutical compositions are preferably administered parenterally, i.e., intraarticularly, intravenously, intraperitoneally, subcutaneously, or intramuscularly. More preferably, the pharmaceutical compositions are administered intravenously or intraperitoneally by a bolus injection. For example, see Stadler, et al., U.S. Pat. No. 5,286,634, which is incorporated herein by reference. Intracellular nucleic acid delivery has also been discussed in Straubringer, et al., METHODS IN ENZYMOLOGY, Academic Press, New York. 101:512–527 (1983); Mannino, et al., Biotechniques 6:682–690 (1988); Nicolau, et al., Crit. Rev. Ther. Drug Carrier Syst. 6:239–271 (1989), and Behr, Acc. Chem. Res. 26:274–278 (1993). Still other methods of administering lipid-based therapeutics are described in, for example, Rahman et al., U.S. Pat. No. 3,993,754; Sears, U.S. Pat. No. 4,145,410; Papahadjopoulos et al., U.S. Pat. No. 4,235,871;

Schneider, U.S. Pat. No. 4,224,179; Lenk et al., U.S. Pat. No. 4,522,803; and Fountain et al., U.S. Pat. No. 4,588,578.

In certain embodiments, the pharmaceutical preparations may be contacted with the target tissue by direct application of the preparation to the tissue. The application may be made by topical, "open" or "closed" procedures. By "topical", it is meant the direct application of the pharmaceutical preparation to a tissue exposed to the environment, such as the skin, oropharynx, external auditory canal, and the like. "Open" procedures are those procedures which include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

The lipid-nucleic acid particles can also be administered in an aerosol inhaled into the lungs (see, Brigham, et al., Am. J. Sci. 298(4):278–281 (1989)) or by direct injection at the site of disease (Culver, HUMAN GENE THERAPY, Mary-Ann Liebert, Inc., Publishers, New York. pp.70–71 (1994)).

The methods of the present invention may be practiced in a variety of hosts. Preferred hosts include mammalian species, such as humans, non-human primates, dogs, cats, cattle, horses, sheep, and the like.

The amount of particles administered will depend upon the the ratio of nucleic acid to lipid; the particular nucleic acid used, the disease state being diagnosed; the age, weight, and condition of the patient and the judgement of the clinician; but will generally be between about 0.01 and about 50 mg per kilogram of body weight; preferably between about 0.1 and about 5 mg/kg of body weight or about $10^8$–$10^{10}$ particles per injection.

3. Insertion of Functional Copy of a Gene

Some methods of gene therapy serve to compensate for a defect in an endogenous gene by integrating a functional copy of the gene into the host chromosome. The inserted gene replicates with the host DNA and is expressed at a level to compensate for the defective gene. Diseases amendable to treatment by this approach are often characterized by recessive mutations. That is, both copies of an endogenous gene must be defective for symptoms to appear. Such diseases include cystic fibrosis, sickle cell anemia, β-thalassemia, phenylketonuria, galactosemia, Wilson's disease, hemochromatosis, severe combined immunodeficiency disease, alpha-1-antitrypsin deficiency, albinism, alkaptonuria, lysosomal storage diseases, Ehlers-Danlos syndrome, hemophilia, glucose-6-phosphate dehydrogenase deficiency, agammaglobulimenia, diabetes insipidus, Lesch-Nyhan syndrome, muscular dystrophy, Wiskott-Aldrich syndrome, Fabry's disease, fragile X-syndrome, and the like. Other recessive mutations are known in the art, and the use of the methods of the present invention to treat them is contemplated herein.

There are several methods for introducing an exogenous functional gene to compensate for the above genetic defects. In one approach, cells are removed from a patient suffering from the disease and contacted with a lipid-vector complex in vitro. Cells should be removed from a tissue type in which disease symptoms are manifested. If the cells are capable of replication, and the vector used includes a selective marker, cells having internalized and expressed the marker can be selected. Particularly if selection is not performed, it is important that the frequency of gene transfer into cells be high, for example, at least about 1, 5, 10, 25 or 50% of cells.

After integration of the vector into the cellular genome, and optionally, selection, cells are reintroduced into the patient. In this application, and others discussed below (except site-specific recombination to correct dominant mutations), it is not necessary that the gene supplied by the lipid-nucleic acid particle be delivered to the same site as is occupied by the defective gene for which it is compensating.

Alternatively, the lipid-vector complex can be introduced directly into a patient as a pharmaceutical composition. The complex is delivered to the tissue(s) affected by the genetic disorder being treated in a therapeutically effective dose. In this and other methods, a therapeutically effective dose is an amount sufficient to cure, or at least partially arrest, the symptoms of the disease and its complications. Effective doses of the compositions of the present invention, for the treatment of the above described conditions will vary depending upon many different factors, including means of administration, target site, physiological state of the patient, and other medicants administered. Thus, treatment dosages will need to be titrated to optimize safety and efficacy. Doses ranging from about 10 ng to 1 g, 100 ng to 100 mg, 1 $\mu$g to 10 mg, or 30–300 $\mu$g DNA per patient are typical. Routes of administration include oral, nasal, gastric, intravenous, intradermal and intramuscular.

The nucleic acid-lipid complexes can also be used to transfect embryonic stem cells or zygotes to achieve germ-line alterations. See Jaenisch, Science, 240, 1468–1474 (1988); Gordon et al. (1984) Methods Enzymol. 101, 414; Hogan et al., Manipulation of the Mouse Embryo: A Laboratory Manual, C.S.H.L. N.Y. (1986); and Hammer et al. (1985) Nature 315, 680; Gandolfi et al. (1987) J. Reprod. Fert. 81, 23–28; Rexroad et al. (1988) J. Anim. Sci. 66, 947–953 and Eyestone et al. (1989) J. Reprod. Fert. 85, 715–720; Camous et al. (1984) J. Reprod. Fert. 72, 779–785; Heyman et al. (1987) Theriogenology 27, 5968. However, these methods are presently more suitable for veterinary applications that human treatment due to ethical and regulatory constraints in manipulating human embryos.

As an example, cystic fibrosis (CF) is a usually fatal recessive genetic disease, having a high incidence in Caucasian populations. The gene responsible for this disease was isolated by Riordan et al, Science 245, 1059–1065 (1989). It encodes a protein called the cystic fibrosis transmembrane conductance regulator (CFTR) which is involved in the transfer of chloride ions (Cl$^-$) through epithelial cell membranes. Mutations in the gene cause defects of Cl$^-$ secretion in epithelial cells leading to the various clinical manifestations. Although CF has a number of symptoms including thickened exocrine gland secretions, pancreatic deficiency, intestinal blockage and malabsorption of fat, the most serious factor affecting mortality is chronic lung disease. Accordingly, to treat a CF patient, a vector containing a coding sequence for a functional CFTR gene product can be complexed with lipid, and optionally, a pharmaceutical excipient and introduced into the patient via nasal administration so that the vector-lipid composition reaches the lungs. The dose of vector-lipid complex is preferably about $10^8$–$10^{10}$ particles.

As another example, defects in the α or γ globin genes (see McDonagh & Nienhuis in *Hematology of Infancy and Childhood* (eds. Nathan & Oski, Saunders, Pa., 1992) at pp. 783–879) can be compensated for by ex vivo treatment of hemopoietic stem cells with an nucleic acid-lipid complex containing a functional copy of the gene. The gene integrates into the stem cells which are then reintroduced into the patient. Defects in the gene responsible for Fanconi Anemia Complement Group C can be treated by an analogous strategy (see Walsh et al., *J. Clin. Invest.* 94, 1440–1448 (1994)).

Other applications include the introduction of a functional copy of a tumor suppressor gene into cancerous cell or cells at risk of becoming cancerous. Individuals having defects in one or both copies of an endogenous tumor suppressor gene are particularly at risk of developing cancers. For example, Li-Fraumeni syndrome is a hereditary condition in which individuals receive mutant p53 alleles, resulting in the early onset of various cancers (Harris, *Science* 262, 1980–1981 (1993) Frebourg et al., *PNAS* 89, 6413–6417 (1992); Malkin et al., *Science* 250, 1233 (1990)). Expression of a tumor suppressor gene in a cancerous cell or a cell at risk of becoming cancerous is effective to prevent, arrest and/or reverse cellular proliferation and other manifestations of the cancerous state. Suitable tumor suppressor genes for use in the invention include p53 (Buchman et al., *Gene* 70, 245–252 (1988)), APC, DCC, Rb, WT1, and NF1 (Marx, *Science* 260, 751–752 (1993); Marshall, *Cell* 64, 313–326 (1991)). Lipid-nucleic acid complexes bearing a functional copy of a tumor suppressor gene are usually administered in vivo by the route most proximal to the intended site of action. For example, skin cancers can be treated by topical administration and leukemia by intravenous administration.

4. Suppression of Gene Expression

Methods of gene therapy using the nucleic acid-lipid complexes of the invention can also be used for prophylactic or therapeutic treatment of patients or cells, infected with or at risk of being infected with, a pathogenic microorganism, such as HIV. The effectiveness of antisense molecules in blocking target gene functions of impeding virus replication has been demonstrated in a number of different systems (Friedman et al., *Nature* 335, 452–54 (1988), Malim et al., *Cell* 58, 205–14 (1989) & Trono at al., *Cell* 59, 113–20 (1989)). The vector used includes a DNA segment encoding an antisense transcript, which is complementary to a segment of the genome from the pathogenic microorganism. The segment should preferably play an essential role in the lifecycle of the microorganism, and should also be unique to the microorganism (or at least absent from the genome of the natural genome of a patient undergoing therapy). For example, suitable sites for inhibition on the HIV virus includes TAR, REV or nef (Chatterjee et al., *Science* 258, 1485–1488 (1992)). Rev is a regulatory RNA binding protein that facilitates the export of unspliced HIV pre mRNA from the nucleus. Malim et al., *Nature* 338, 254 (1989). Tat is thought to be a transcriptional activator that functions by binding a recognition sequence in 5' flanking mRNA. Karn & Graeble, *Trends Genet.* 8, 365 (1992). The nucleic acid-lipid complex is introduced into leukocytes or hemopoietic stem cells, either ex vivo or by intravenous injection in a therapeutically effective dose. The treatment can be administered prophylactically to HIV- persons, or to persons already infected with HIV.

Analogous methods are used for suppressing expression of endogenous recipient cell genes encoding adhesion proteins. Suppression of adhesion protein expression in useful in aborting undesirable inflammatory responses. Adhesion proteins that can be suppressed by antisense segments present in selected vectors include integrins, selectins, and immunoglobulin (Ig) superfamily members (see Springer, *Nature* 346, 425–433 (1990). Osborn, *Cell* 62, 3 (1990); Hynes, *Cell* 69, 11 (1992)). Integrins are heterodimeric transmembrane glycoproteins consisting of an α chain (120–180 kDa) and a β chain (90–110 kDa), generally having short cytoplasmic domains. The three known integrins, LFA-1, Mac-1 and P150,95, have different alpha subunits, designated CD11a, CD11b and CD11c, and a common beta subunit designated CD18. LFA-1 ($\alpha_L\beta_2$) is expressed on lymphocytes, granulocyte and monocytes, and binds predominantly to an Ig-family member counter-receptor termed ICAM-1 (and perhaps to a lesser extent ICAM-2). ICAM-1 is expressed on many cells, including leukocytes and endothelial cells, and is up-regulated on vascular endothelium by cytokines such as TNF and IL-1. Mac-1 ($\alpha_M\beta_2$) is distributed on neutrophils and monocytes, and also binds to ICAM-1 (and possibly ICAM-2). The third β2 integrin, P150,95 ($\alpha_X\beta_2$), is also found on neutrophils and monocytes. The selectins consist of L-selectin, E-selectin and P-selectin.

5. Cells to be Transformed

The compositions and methods of the present invention are used to treat a wide variety of cell types, in vivo and in vitro. Among those most often targeted for gene therapy are hematopoietic precursor (stem) cells. Other cells include those of which a proportion of the targeted cells are nondividing or slow dividing. These include, for example, fibroblasts, keratinocytes, endothelial cells, skeletal and smooth muscle cells, osteoblasts, neurons, quiescent lymphocytes, terminally differentiated cells, slow or non-cycling primary cells, parenchymal cells, lymphoid cells, epithelial cells, bone cells, etc. The methods and compositions can be employed with cells of a wide variety of vertebrates, including mammals, and especially those of veterinary importance, e.g., canine, feline, equine, bovine, ovine, caprine, rodent, lagomorph, swine, etc., in addition to human cell populations.

To the extent that tissue culture of cells may be required, it is well known in the art. Freshney (1994) (*Culture of Animal Cells, a Manual of Basic Technique, third edition* Wiley-Liss, New York), Kuchler et al. (1977) *Biochemical Methods in Cell Culture and Virology*, Kuchler, R. J., Dowden, Hutchinson and Ross, Inc., and the references cited therein provides a general guide to the culture of cells. Cultured cell systems often will be in the form of monolayers of cells, although cell suspensions are also used.

Gene therapy relies on the efficient delivery of therapeutic genes to target cells. Most of the somatic cells that have been targeted for gene therapy, e.g., hematopoietic cells, skin fibroblasts and keratinocytes, hepatocytes, endothelial cells, muscle cells and lymphocytes, are normally non-dividing. Retroviral vectors, which are the most widely used vectors for gene therapy, unfortunately require cell division for effective transduction (Miller et al., *Mol. Cell. Biol.* 10:4239–4242 (1990)). This is also true with other gene therapy vectors such as the adeno-associated vectors (Russell et al., *Proc. Natl. Acad. Sci. USA* 91: 8915–8919 (1994); Alexander et al., *J. Virol.* 68: 8282–8287 (1994); Srivastrava, *Blood Cells* 20: 531–538 (1994)). Recently, HIV-based vectors has been reported to transfect non-dividing cells (CITE) Nonetheless, the majority of stem cells, a preferred target for many gene therapy treatments, are normally not proliferating. Thus, the efficiency of transduction is often relatively low, and the gene product may not be expressed in therapeutically or prophylactically effective amounts. This has led investigators to develop techniques such as stimulating the stem cells to proliferate priot to or during gene transfer (e.g., by treatment with growth factors) pretreatment with 5-fluorouracil, infection in the presence of cytokines, and extending the vector infection period to increase the likelihood that stem cells are dividing during infection, but these have met with limited success.

6. Detection of Foreign Nucleic Acids

After a given cell is transduced with a nucleic acid construct that encodes a gene of interest, it is important to detect which cells or cell lines express the gene product and to assess the level of expression of the gene product in engineered cells. This requires the detection of nucleic acids that encode the gene products.

Nucleic acids and proteins are detected and quantified herein by any of a number of means well known to those of skill in the art. These include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like. The detection of nucleic acids proceeds by well known methods such as Southern analysis, northern analysis, gel electrophoresis, PCR, radiolabeling, scintillation counting, and affinity chromatography.

The selection of a nucleic acid hybridization format is not critical. A variety of nucleic acid hybridization formats are known to those skilled in the art. For example, common formats include sandwich assays and competition or displacement assays. Hybridization techniques are generally described in "Nucleic Acid Hybridization, A Practical Approach," Ed. Hames, B. D. and Higgins, S. J., IRL Press, 1985.

The sensitivity of the hybridization assays may be enhanced through use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al. (1987), U.S. Pat. No. 4,683,202; *PCR Protocols A Guide to Methods and Applications* (Innis et al. eds) Academic Press Inc. San Diego, Calif. (1990) (Innis); Amheim & Levinson (Oct. 1, 1990), *C&EN* 36–47; *The Journal Of NIH Research* (1991), 3: 81–94; (Kwoh et al. (1989), *Proc. Natl. Acad. Sci. USA*, 86: 1173; Guatelli et al. (1990), *Proc. Natl. Acad. Sci. USA*, 87: 1874; Lomell et al. (1989), *J. Clin. Chem.*, 35: 1826; Landegren et al. (1988), *Science*, 241: 1077–1080; Van Brunt (1990), *Biotechnology*, 8: 291–294; Wu and Wallace (1989), *Gene*, 4: 560; Barringer et al. (1990), *Gene*, 89: 117, and Sooknanan and Malek (1995), *Biotechnology*, 13: 563–564. Improved methods of cloning in vitro amplified nucleic acids are described in Wallace et al., U.S. Pat. No. 5,426,039. Other methods recently described in the art are the nucleic acid sequence based amplification (NASBA™, Cangene, Mississauga, Ontario) and Q Beta Replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation.

Oligonucleotides for use as probes, e.g., in in vitro amplification methods, for use as gene probes, or as inhibitor components are typically synthesized chemically according to the solid phase phosphoramidite triester method described by Beaucage and Caruthers (1981), *Tetrahedron Letts.*, 22(20): 1859–1862, e.g., using an automated synthesizer, as described in Needham-VanDevanter et al. (1984), *Nucleic Acids Res.*, 12: 6159–6168. Purification of oligonucleotides, where necessary, is typically performed by either native acrylamide gel electrophoresis or by anion-exchange HPLC as described in Pearson and Regnier (1983), *J. Chrom.*, 255: 137–149. The sequence of the synthetic oligonucleotides can be verified using the chemical degradation method of Maxam and Gilbert (1980) in Grossman and Moldave (eds.) Academic Press, New York, *Methods in Enzymology*, 65: 499–560.

An alternative means for determining the level of expression of the gene is in situ hybridization. In situ hybridization assays are well known and are generally described in Angerer et al. (1987), *Methods Enzymol.*, 152: 649–660. In an in situ hybridization assay cells are fixed to a solid support, typically a glass slide. If DNA is to be probed, the cells are denatured with heat or alkali. The cells are then contacted with a hybridization solution at a moderate temperature to permit annealing of specific probes that are labelled. The probes are preferably labelled with radioisotopes or fluorescent reporters.

7. Detection of Foreign Gene Products

The expression of the gene of interest to produce a product may be detected or quantified by a variety of methods. Preferred methods involve the use of specific antibodies.

Methods of producing polyclonal and monoclonal antibodies are known to those of skill in the art. See, e.g., Coligan (1991), CURRENT PROTOCOLS IN IMMUNOLOGY, Wiley/Greene, NY; and Harlow and Lane (1989), ANTIBODIES: A LABORATORY MANUAL, Cold Spring Harbor Press, NY; Stites et al. (eds.) BASIC AND CLINICAL IMMUNOLOGY (4th ed.) Lange Medical Publications, Los Altos, Calif., and references cited therein; Goding (1986), MONOCLONAL ANTIBODIES: PRINCIPLES AND PRACTICE (2d ed.) Academic Press, New York, N.Y.; and Kohler and Milstein (1975), *Nature*, 256: 495–497. Such techniques include antibody preparation by selection of antibodies from libraries of recombinant antibodies in phage or similar vectors. See, Huse et al. (1989), *Science*, 246: 1275–1281; and Ward et al. (1989), *Nature*, 341: 544–546. Specific monoclonal and polyclonal antibodies and antisera will usually bind with a $K_D$ of at least about 0.1 mM, more usually at least about 1 $\mu$M, preferably at least about 0.1 $\mu$M or better, and most typically and preferably, 0.01 $\mu$M or better.

The presence of a desired polypeptide (including peptide, transcript, or enzymatic digestion product) in a sample may be detected and quantified using Western blot analysis. The technique generally comprises separating sample products by gel electrophoresis on the basis of molecular weight, transferring the separated proteins to a suitable solid support, (such as a nitrocellulose filter, a nylon filter, or derivatized nylon filter), and incubating the sample with labeling antibodies that specifically bind to the analyte protein. The labeling antibodies specifically bind to analyte on the solid support. These antibodies are directly labeled, or alternatively are subsequently detected using labeling agents such as antibodies (e.g., labeled sheep anti-mouse antibodies where the antibody to an analyte is a murine antibody) that specifically bind to the labeling antibody.

VII. EXAMPLES

The following examples are offered solely for the purposes of illustration, and are intended neither to limit nor to define the invention. In each of these examples, the term "DNA" or "plasmid" refers to the plasmid pCMV (pCMV4-CAT).

A. Materials

Transfecting agents Lipofectin and Lipofectamine were purchased from Gibco/BRL (Grand Island, N.Y., USA). Transfectam Reagent was purchased from Promega Corp. (Madison, Wis., USA). The monocationic lipid DDAB, calcium chloride, L-lysine (free base), poly L-lysine hydrobromide (Avg. MW 52,000), n-octyl -D-glucopyranoside (OGP) and DNase I were obtained from Sigma Chemical Company (St. Louis, Mo., USA). TO-PRO-1 (thiazole orange monomer) was obtained from Molecular Probes Inc., Eugene, Oreg., USA. The plasmid pCMV (GenBank accession # U02451) encoding $E.$ $coli$-galactosidase (-gal), a 7.2 kb plasmid DNA reporter gene, was obtained from Clontech Laboratories, Palo Alto, Calif., USA. β-gal DNA was propagated and purified using standard techniques (Sambrook et al., Molecular Cloning, A Laboratory Manual, Second Ed., Cold Spring Harbor, N.Y. (1989)). Egg sphingomyclin (SM) and 1,2-dioleoyl-sn-Glycero-3-phosphoethanolamine (DOPE) were purchased from Avanti Polar Lipids (Alabaster, Ala.). N-N-diolcoyl-N,N-dimethylammonium chloride (DODAC) was synthesized and supplied by Steven Ansell of INEX Pharmaceuticals Corp. (Vancouver, B.C.). TO-PRO-1 was purchased from Molecular Probes Inc. (Eugene, Ore.). Dialysis membrane (SPECTRA/POR, mwco: 12.000–14,000) was purchased from Fisher Scientific (Ottawa, ON). All other chemicals used were reagent grade and all solvents used were HPLC grade. Radiolabeled DNA was used as a tracer and was generated by incorporating 3H-dUTP into the plasmid during bacterial growth, resulting in specific activities of ~50,000 dpm/g of DNA. All other chemicals used in these Examples were of reagent grade and all solvents used were HPLC grade. Sterile distilled water was used throughout all experiments. All materials were used without further purification.

B. Methods

Bligh and Dyer Extraction Procedure

Non-cationic lipids, cationic lipids and DNA were solubilized in chloroform: methanol:water (1:2.1:1) prior to mixing. This mixture of solvents and water is equivalent to that used in the preparation of a Bligh and Dyer monophase (Bligh and Dyer, Can. J. Biochem. Physiol. 37:91–97 (1959)). Typically, DNA was added to achieve a final concentration of 10 g/mL in solution while lipid was added at various concentrations. Trace quantities of 3H-plasmid DNA were added such that 2000 to 4000 dpm were present per 10 g unlabelled DNA. The reaction mixtures were incubated at room temperature for 30 min in a total volume of 1 mL. Subsequently the Bligh and Dyer monophase was partitioned into a two phase system by the addition of water and chloroform (250 L each). The samples were mixed by vortexing and the separation of the lower organic and upper aqueous phases was facilitated by centrifugation at 2000 rpm for 5 min at room temperature. The aqueous phase was removed and retained for scintillation counting. The solvent phase was dried using a stream of nitrogen gas, and the resulting film was resuspended in SOLVABLE solubilizing agent (Dupont NEN, Boston, Mass., USA) and incubated at 50° C. for 1 hour. This last step was necessary to solubilize the dried DNA/lipid complex since the addition of the scintillation cocktail alone was not sufficient to dissociate the complex. PICOFLUOR scintillant (Canberra Packard, Meriden, Conn., USA) was added to all samples and the radioactivity (3H-DNA) was measured using a Packard TR 1900 Scintillation Counter (Canberra Packard).

Assays evaluating the stability of charge-neutralized, lipid-nucleic acid complexes were done in the presence of varying concentration of NaCl and OGP. Briefly, cationic lipid-nucleic acid complexes were prepared under conditions where 100% of the plasmid was expected to be recovered in the organic phase. NaCl or OGP was then added to the monophase system and incubations carried out at room temperature for 15 min. Bligh and Dyer extractions were performed as described above. The binding of calcium, L-lysine, and poly-L-lysine to the plasmid was evaluated using a modification of the above procedure. These nonlipid cationic materials were dissolved at various concentrations in sterile distilled water and incubated with the plasmid (10 g/mL final concentration in water) at room temperature for 30 min in a final volume of 250 L. Reaction volumes were adjusted to 1 mL with chloroform:methanol (1:2.1) to produce a monophase. Bligh and Dyer extractions were then performed as described.

Dye Intercalation Assay

The fluorochrome TO-PRO-1 was used to evaluate the state of condensation of the plasmid in the charge-neutralized lipid-nucleic acid complex. TO-PRO-1 was used in this study due to its stable intercalation into the plasmid as well as the high sensitivity in the fluorescence detection compared with the more common intercalator ethidium bromide (see, Hirons, et al., Cytometry 15:129–140 (1994)). Plasmid was dissolved in either the Bligh and Dyer monophase or in 100 mM OGP. Poly-L-lysine or DODAC were each added to 10 g plasmid at a 1:1 charge ratio.

Agarose Gel Electrophoresis

Complexes involving plasmid and poly-L-lysine were formed at a nucleic acid concentration of 10 g/mL and a 1:1 charge ratio in the presence of 100 mM OGP. Complexes involving the cationic lipid DODAC and plasmid were formed at a plasmid concentration of 10 g/mL and increasing concentrations of DODAC (10 to 320 nmoles/mL). The mixtures were incubated at room temperature for 30 min prior to loading onto a 0.8% agarose gel. Electrophoresis was carried out in TBE buffer according to standard techniques (Sambrook, et al., Molecular Cloning: A Laboratory Manual, Second Edition, Cold Spring Harbor, N.Y. (1989)). Nucleic acids were visualized after staining the gel with ethidium bromide (0.5 g/mL, 20 min) by photography with UV transillumination.

DNAse I Assay

To evaluate the protective effect of cationic lipids on DNA, the complexes formed in the presence of OGP were incubated with DNase I. Preformed charge-neutralized lipid-nucleic acid complexes (plasmid/DODAC; 1:1 charge ratio) were mixed with DNase I at a concentration where plasmid alone was susceptible to degradation at 37° C. for 10 min.

The reactions were stopped by the addition of 25 mM EDTA and the samples were extracted using the Bligh and Dyer procedure in the presence of 150 mM NaCl. Under these conditions the charge-neutralized lipid-nucleic acid complexes dissociate and plasmid can be efficiently recovered in the aqueous fraction. This DNA was precipitated with 1/10th volume of 3 M sodium acetate (pH 5.2) and 2.5 volumes of 95% EtOH and recovered by centrifugation at 14,000 g for 30 min at 4C. The DNA pellet was resuspended in sterile distilled water and subjected to electrophoresis on a 0.8% agarose gel.

EXAMPLE 1

This example illustrates the encapsulation of a plasmid in a lipid particle using either a reverse-phase method or a detergent dialysis method.

Reverse Phase Method pCMV4-CAT plasmid was encapsulated in a lipid particle which was constructed using about 10 mg or 20 mg of lipid. The encapsulation method involved a modification of the classical reverse phase method for entrapment. Generally, 1.050 ml of chloroform: methanol in a 1:2–1 mole % ratio was added to a lipid film containing 2 μl of $^{14}$C-cholesteryl hexadecyl ether (6.66 μl/μCi). This was followed by the addition of 220 μl $H_2O$ and 33 μl $^3$H-pCMVCAT plasmid (158,000 dpm/μl; 1.5 mg/ml). This combination provided a clear single phase. The chloroform and most of the methanol were removed under a stream of nitrogen while vortexing. In some cases, the resulting 250 μl suspension of encapsulated plasmid was diluted with 1 ml of $H_2O$ and extruded 5 times through one 400 nm filter followed by extrusion 5 times through one 200 nm filter. The resulting vesicle size was approximately 150 to 200 nm in diameter. Liposome sizes before extrusion varied greatly depending on the lipid composition.

Detergent Dialysis Method pCMVCAT was incubated with DODAC at various DODAC concentrations in 100 μl of 1 M n-octyl-B-D-glucopyranoside and 400 μl of $H_2O$ for 30 min at room temperature. The resulting plasmid:DODAC mixture was added to a suspension of approximately 10 mg of lipid containing 1 μl, $^{14}$C-cholesteryl hexadecyl ether; 6.66 μl/Ci in 100 μl of 1M n-octyl-β-D-glucopyranoside. The suspension was dialysed against HBS at pH 7.4 overnight. The resulting encapsulated plasmid could be used without further sizing.

EXAMPLE 2

This example illustrates the level of plasmid "protection" from the external medium using anion exchange chromatography.

The extent of encapsulation or protection of the plasmid from the external medium was assessed by anion exchange chromatography as follows: a 50 μl aliquot of each sample was eluted on a DEAE Sepharose CL-6B column and the fractions were assessed for both $^3$H-plasmid and $^{14}$C-lipid by scintillation counting. Any exposed negative charges, such as those present on DNA molecules will bind-to the anion exchange column and will not elute with the $^{14}$C-lipid. DNA which has its negative charge, "protected" or non-exposed will not bind to the anion exchange resin and will elute with the $^{14}$C-lipid. Alternatively, plasmid DNA was measured using the indicator dye, PicoGreen®.

Reverse Phase Method

Figure 4:
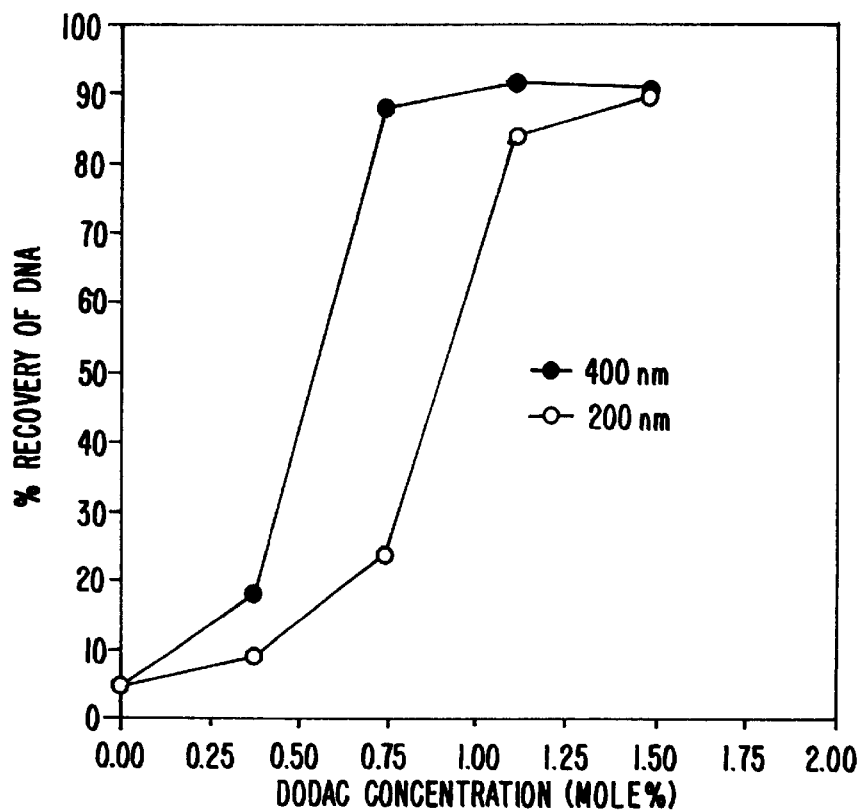
FIG. 4 illustrates the recovery of $^3$H-DNA from encapsulated particles following the reverse-phase preparation of the particles and extrusion through a 400 nm filter and a 200 nm filter. Lipid composition is POPC:DODAC:PEG-Cer-$C_{20}$. PEG-CerC$_{20}$ was held constant at 10 mole % and POPC and DODAC were changed relative to each other. 20 mg lipid; 50 µg plasmid DNA (7.5 kbp).
Figure 5:
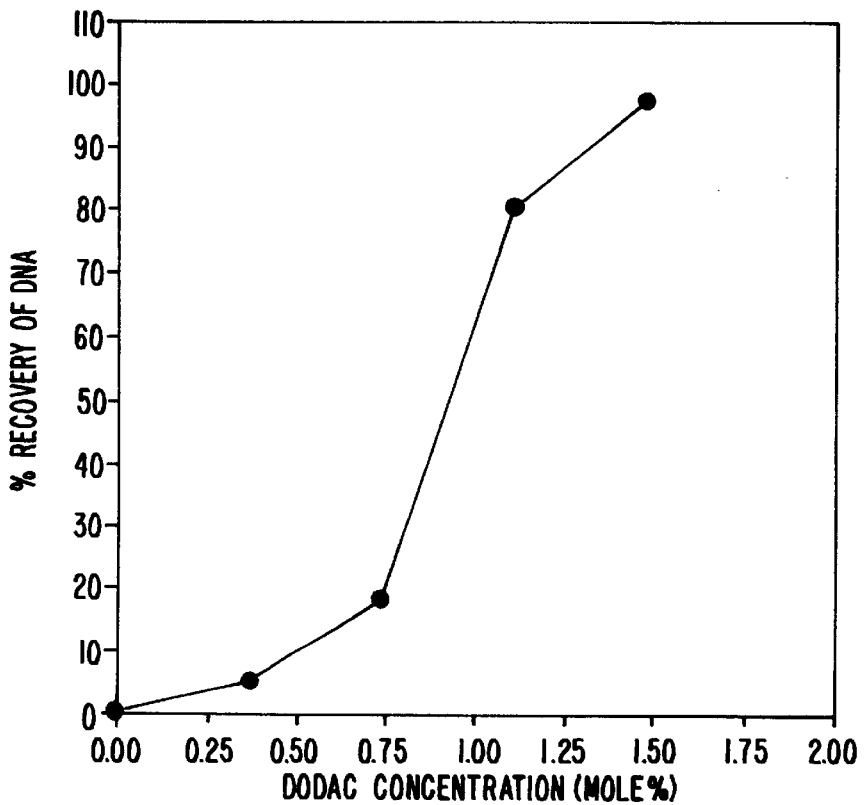
FIG. 5 illustrates the recovery of 3H-DNA from particles prepared using a reverse-phase procedure. The particles were extruded through a 200 nm filter and eluted on a DEAE Sepharose CL-6B anion exchange column. The percent recovery reported is based on the amount recovered after filtration. Lipid composition is as in FIG. 4.
Figure 7:
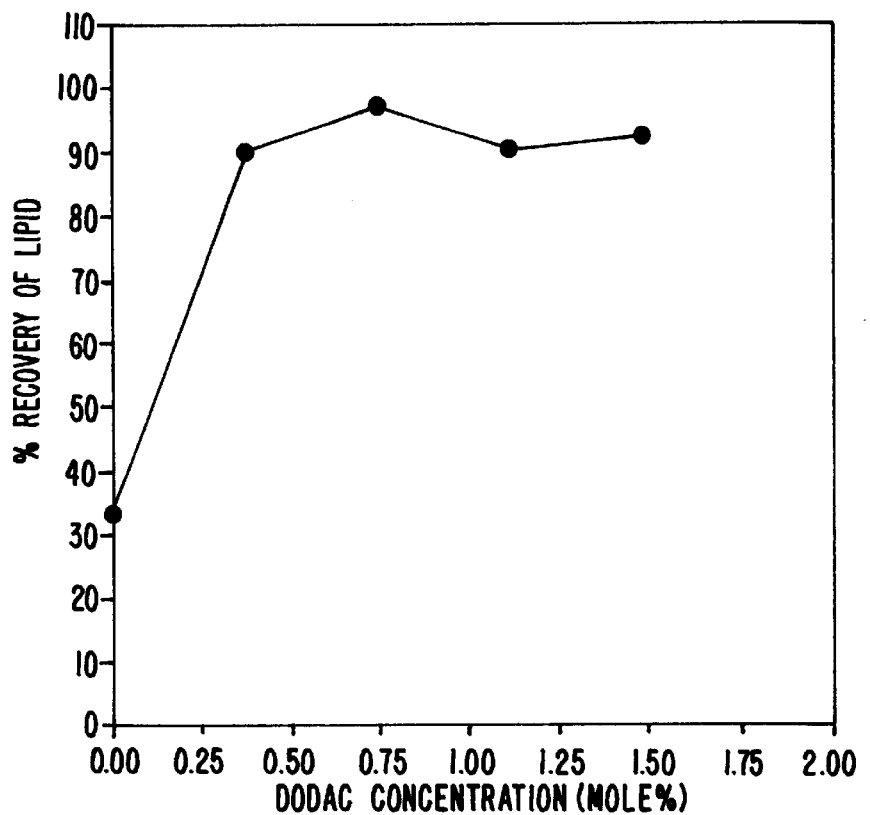
FIG. 7 illustrates the recovery of $^{14}$C-lipid from particles prepared using a reverse-phase procedure. The particles were extruded through a 200 nm filter and eluted on a DEAE Sepharose CL-6B anion exchange column. The percent recovery reported is based on the amount recovered after filtration. Lipid composition is as in FIG. 4.
Figure 6:
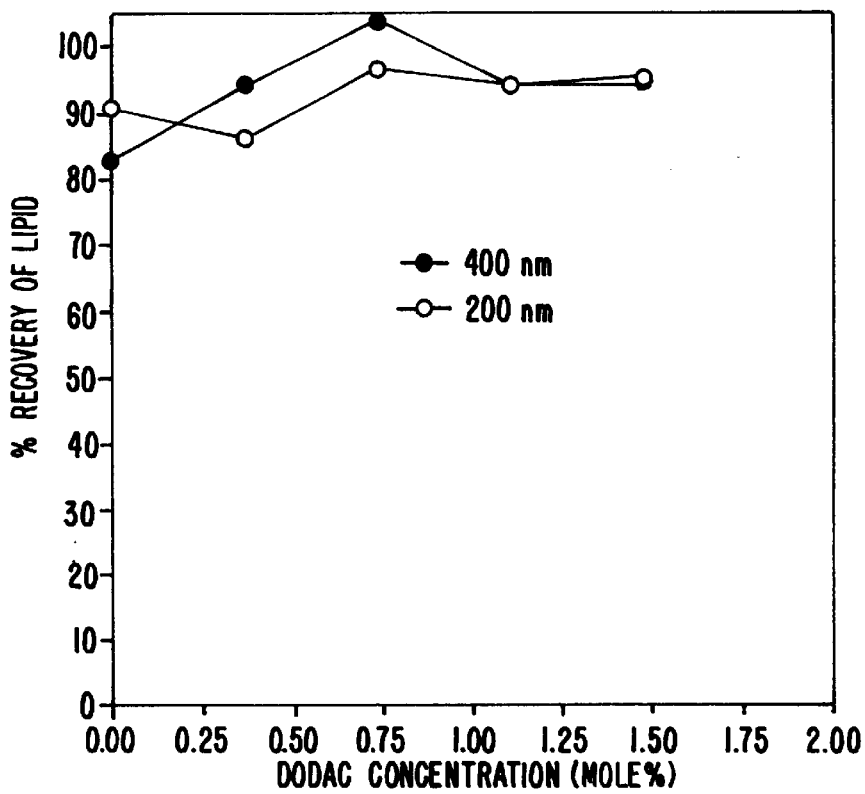
FIG. 6 illustrates the recovery of $^{14}$C-lipid from encapsulated particles following the reverse-phase preparation of the particles and extrusion through a 400 nm filter and a 200 nm filter. Lipid composition is as in FIG. 4.

FIG. 4 presents the results describing the relationship between the amount of DODAC present in the formulation and the encapsulation efficiency for POPC:DODAC:PEG-Cer-$C_{20}$ (20 mg total lipid) compositions after extrusion through a 400 nm filter and a 200 nm filter as measured by anion exchange chromatography. Lipid was composed of 10% PEG-Cer-$C_{20}$ and the remaining percentage was attributable to POPC and DODAC. An increase in percent plasmid recovered was observed corresponding to an increase in DODAC concentration. No plasmid was recovered in the absence of DODAC while, at a DODAC concentration of 1.5 mole %, 90% of the plasmid was recovered after extrusion through a 200 nm filter. Nearly 100% of the plasmid recovered from extrusion through a 200 mn filter was recovered by anion exchange chromatography (FIG. 5) suggesting that all of the recovered plasmid was encapsulated. This corresponded to an overall encapsulation efficiency of about 70%. Lipid recoveries after extrusion and anion exchange chromatography were 90% after extrusion through a 400 nm filter and 70% after extrusion through a 200 nm filter (see FIG. 6). Of the 70% lipid recovered after extrusion through a 200 nm fitter, nearly 100% was recovered after anion exchange chromatography (FIG. 7). Lipid and plasmid recovery after extrusion and anion exchange chromatography were nearly identical. Table 1 illustrates the encapsulation efficiencies using several different lipid compositions. It is quite evident that a wide range of lipid compositions may be used. It is also interesting to note that PEG-Cer does not appear to be necessary in many of these lipid compositions.

TABLE 1

Some examples of plasmid DNA encapsulation by the modified reverse phase method. Data are shown only when at least 70% of the lipid was recovered from anion exchange chromatography.

| Reverse Phase Lipid composition | % encapsulation |
| --- | --- |
| EPC-DODAC (98.9:1.1) | 98% |
| DOPE:EPC:DODAC (10:88.9:1.1) | 24% |
| DOPE:EPC:DODAC (20:78.9:1,I) | 13% |
| DOPE:EPC:DODAC (40:58.9:1,I) | 16% |
| DOPE:EPC:DODAC-(10:85.5:4.5) | 78% |
| DOPE:EPC:DODAC (15:80.5:4.5) | 67% |
| DOPE:SM:EPC:DODAC (15:40:40:5) | 53% |
| DOPE:SM:EPC:DODAC (20:37.5:37.5:5) | 37% |
| DOPE:EPC:DODAC:PEG-Cer-C8 (25:64:1:10) | 83% |
| DOPE:EPC:DODAC:PEG-Cer-C8 (50:39:1:10) | 90% |

Dialysis Method

Figure 8:
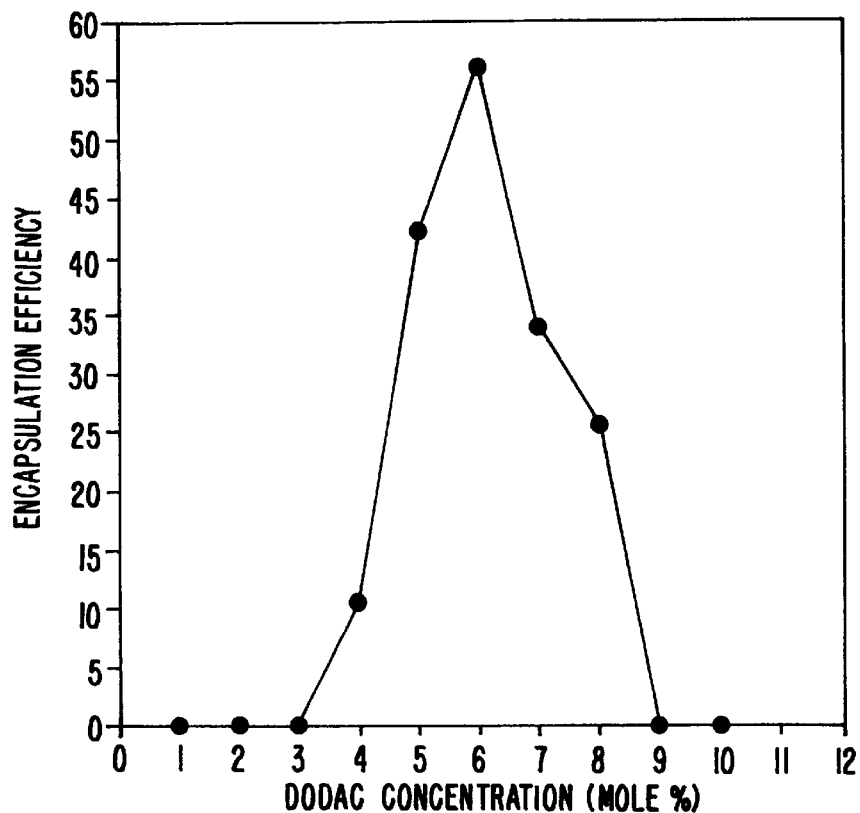
FIG. 8 illustrates the effect of DODAC concentration on the encapsulation of plasmid DNA. Encapsulation efficiency was measured by anion exchange chromatography. Vesicles were composed of DOPE, DODAC and 10 mole % PEG-Cer-$C_{20}$ (symbol) or EPC, DODAC and 10 mole % PEG-Cer-$C_{20}$ (symbol). Total lipid and DNA concentrations were 10 mmole/ml and 50 µg/ml, respectively.

FIG. 8 presents the results describing tile relationship between the amount of DODAC present in the formulation and the encapsulation efficiency for DOPE:DODAC:PEG-Cer-$C_{20}$ (84:6: 10) as measured by anion exchange chromatography. Table 2 illustrates the encapsulation efficiencies using several different lipid compositions. It is quite evident that a wide range of lipid compositions may be used. It is interesting to note that PEG-Cer appears to be necessary in these lipid compositions.

TABLE 2

Some examples of plasmid DNA encapsulation by the detergent dialysis method. Data are shown only when at least 70% of the lipid was recovered from anion exchange chromatography.
Detergent dialysis

| Lipid composition | % encap-sulation | amount of DNA | comments |
|---|---|---|---|
| DOPE:DODAC:PEG-CER-$C_8$ (79:6:15) | 64% | 50 µg–400 µg/10 µmole lipid | dialyzed against 150 mM NaCl |
| DOPE:DODAC:PEG-CER-$C_{14}$ (84:6:10) | 60% | 50 µg–400 µg/10 µmole lipid | dialysed against 150 mM NaCl |
| DOPE:DODAC:PEG-CER-$C_{20}$ (84:6:10) | 52% | 50 µg–400 µg/10 µmole lipid | dialysed against 150 mM NaCl |
| DOPE:DODAC:EPC:PEG-CER-$C_8$ (59:6:20:15) | 20% | 50 µg–400 µg/10 µmole lipid | dialysed against 150 mM NaCl |
| DOPE:DODAC:DOPC:PEG-CER-$C_{14}$ (74:6:10:10) | 36% | 50 µg–400 µg/10 µmole lipid | dialysed against 150 mM NaCl |
| DOPE:DODAC:DOPC:PEG-CER-$C_{14}$ (64:6:20:10) | 17% | 50 µg–400 µg/10 µmole lipid | dialysed against 150 mM NaCl |
| DOPE:DODAC:EPC:Chol:PEG-CER-$C_{14}$ (41:9:20:20:10) | 57% | 50 µg–400 µg/10 µmole lipid | dialysed against 150 mM NaCl |
| DOPE:DODAC:EPC:Chol:PEG-CER-$C_{14}$ (51:9:20:10:10) | 50% | 50 µg–400 µg/10 µmole lipid | dialysed against 150 mM NaCl |
| DOPE:DODAC:PEG-$C_{14}$ (80:10:10) | 22.5% | 50 µg–400 µg/10 µmole lipid | dialysed against 150 mM NaCl |
| DOPE:DODAC:PEG-$C_{14}$ (79:11:10) | 22.7% | 50 µg–400 µg/10 µmole lipid | dialysed against 300 mM NaCl* |
| DOPE:DODAC:PEG-$C_{20}$ (89.4:0.6:10) | 57% | 50 µg/10 µmole lipid | dialysed against 5 mM NaCl* |
| DOPE:DODAC:PEG-CER-$C_{14}$ *87:3:10) | 51% | 50 µg/10 µmole lipid | dialysed against 50 mM NaCl* |

*See Example 6.

EXAMPLE 3

This example illustrates the serum stability achieved using plasmid:lipid particles prepared by the methods of Example 1.

To establish the serum stability of the plasmid-lipid particles aliquots of the particle mixtures prepared according to both the reverse phase and dialysis method of Example 1 were incubated in 80% mouse serum (Cedar Lane) for 30 min at 37° C. Prior to incubation, the lipid associated plasmid was eluted on a DEAE Sepharose CL-6B column to remove unencapsulated plasmid. Following incubation, an aliquot of the incubation mixture was eluted in HBS on a Sepharose CL-4B column.

Figure 9A:
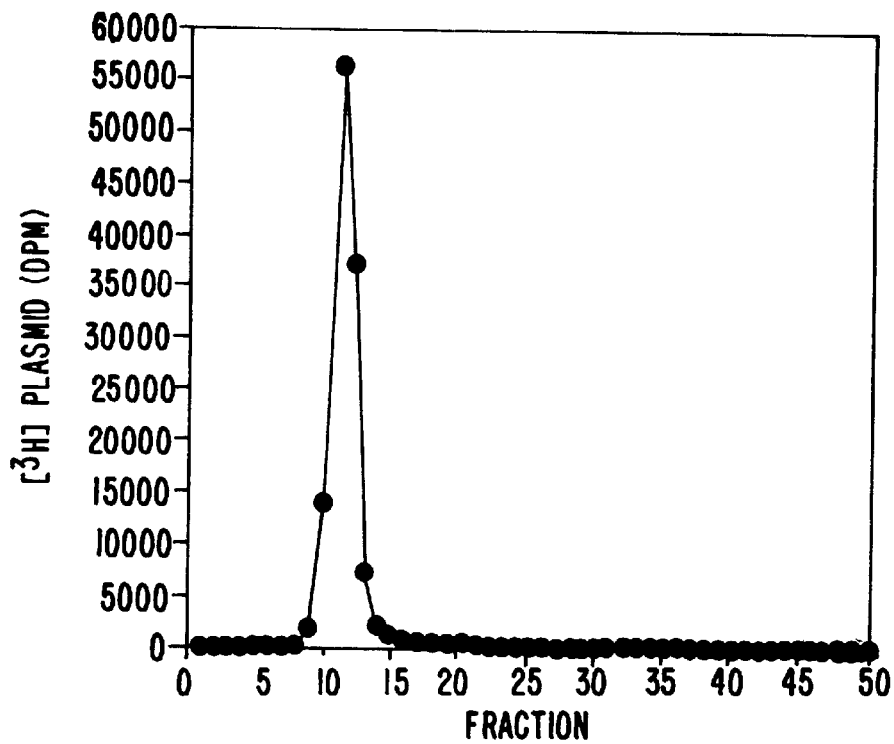
FIGS. 9A and 9B illustrate the effect of serum nucleases on free pCMVCAT DNA as assessed by column chromatography before (A) and after (B) incubation in 80% mouse serum. Free $^3$H-DNA (PCMVCAT) was eluted on a Sepharose CL-4B column in HBS, pH 7.4.
Figure 9B:
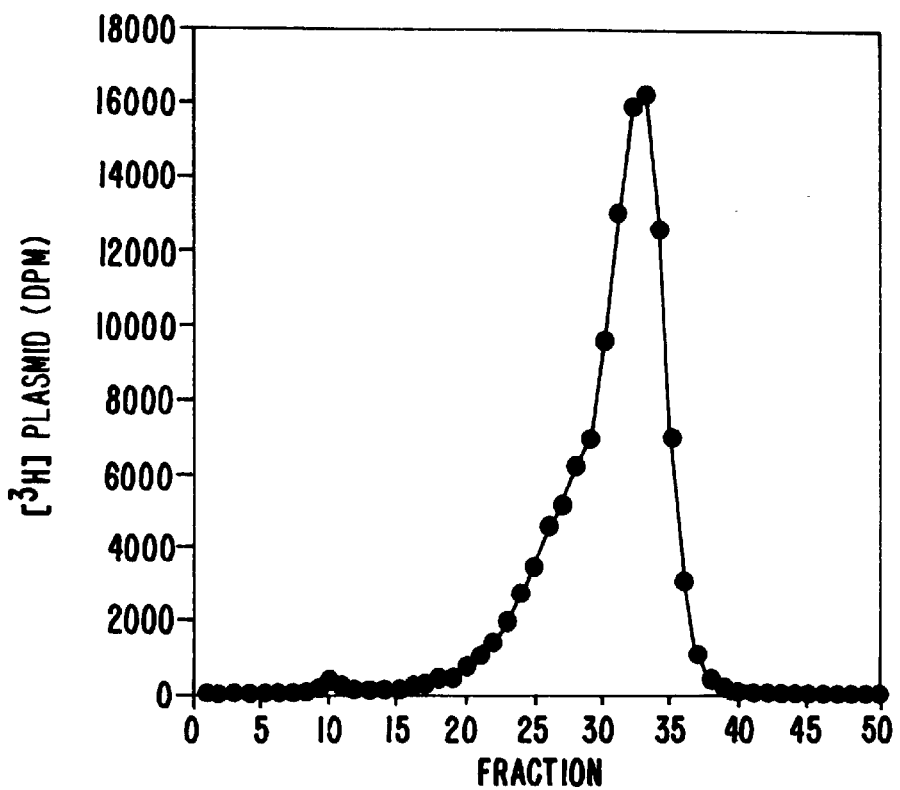

As a control, 1.5 mg of free $^3$H-pCMVCAT was eluted on a Sepharose CL-4B column in HBS, pH 7.4 (see FIG. 9A). For comparison, 1.5 mg of free $^3$H-pCMVCAT was incubated in 500 µl of mouse serum at 37° C. for 30 min and eluted in the same manner (FIG. 9B). Note that in FIG. 9A, the free plasmid eluted in the void volume of the column while, in FIG. 9B, the plasmid incubated in serum eluted in the included volume suggesting that the plasmid had been digested by serum enzymes.

Serum Stability of Plasmid-lipid Particles Prepared by Reverse Phase

Figure 10:
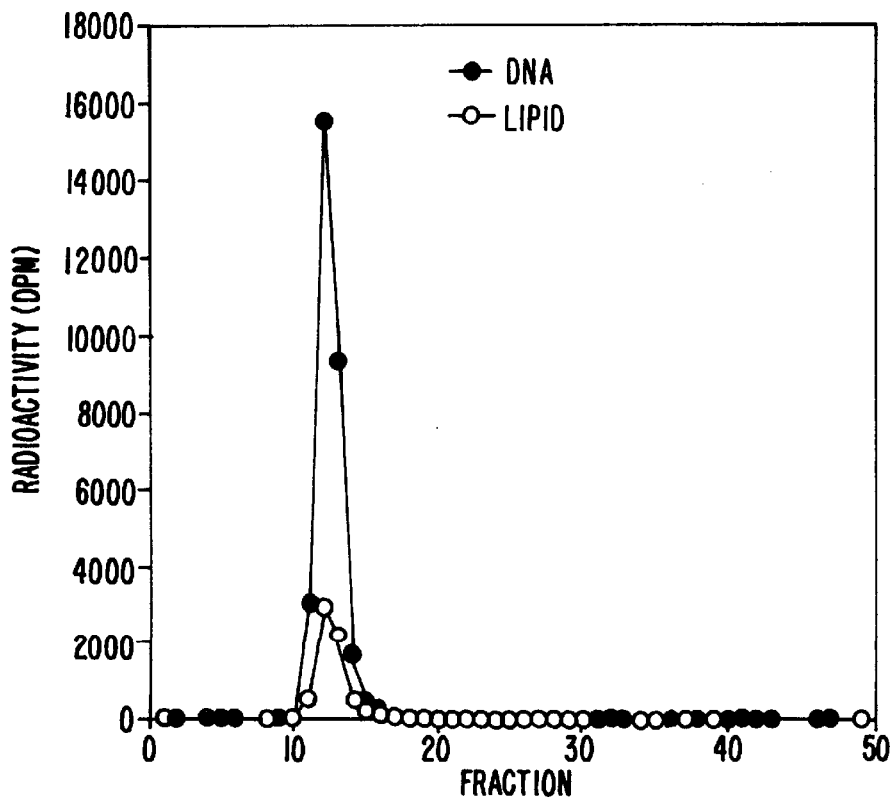
FIG. 10 illustrates the effect of serum nucleases on encapsulated pCMVCAT DNA (prepared by reverse-phase) as assessed by column chromatography. Sepharose CL-4B column profile of encapsulated pCMV plasmid incubated in 80% mouse serum for 30 min. (A) External DNA was removed by ion exchange chromatography prior to incubation in serum. (B) External DNA was not removed prior to incubation in serum. Lipid composition was POPC:DODAC:PEG-Cer-$C_{20}$. Total lipid and plasmid concentrations were 20 µmole/ml and 50 µg/ml prior to anion exchange chromatography.

The stability of plasmid-lipid particles was assessed by incubation of a 50 µl aliquot in 500 µl of mouse serum (Cedar Lane) for 15 min at 37° C. A 500 µl aliquot of the incubation mixture was eluted in HBS on a Sepharose CL-4B column (FIG. 10). Comigration of the plasmid and lipid in the void volume strongly suggests that no plasmid degradation has occurred. Any serum-degraded plasmid or lipid should have been detected as a peak at around fraction 35 (see control results in FIG. 9B).

Serum Stability of Plasmid-lipid Particles Prepared by Dialysis

Figure 11A:
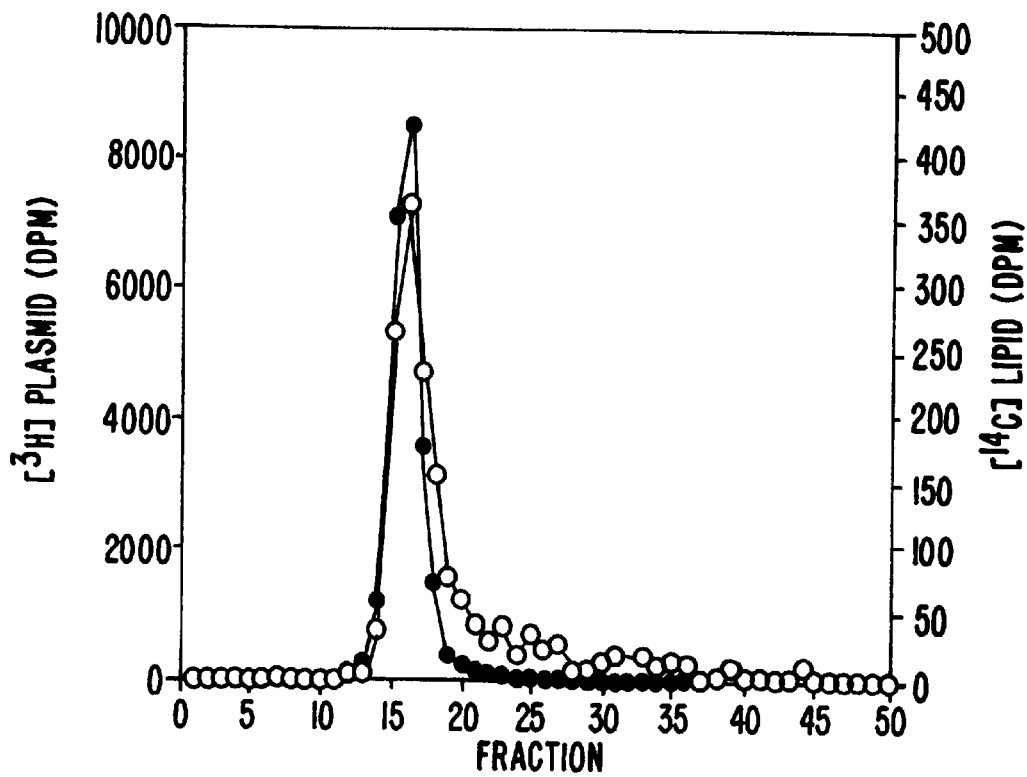
FIGS. 11A and 11B illustrate the effect of serum nucleases on encapsulated pCMVCAT DNA (prepared by detergent dialysis) as assessed by column chromatography. Sepharose CL-4B column profile of encapsulated pCMV plasmid incubated in 80% mouse serum for 30 min. (A) External DNA was removed by ion exchange chromatography prior to incubation in serum. (B) External DNA was not removed prior to incubation in serum. The lipid composition was DOPE:DODAC:PEG-Cer-$C_{20}$ (84:6:10). Total lipid and plasmid concentrations were 10 µmole/ml and 400 µg/ml prior to anion exchange chromatography.
Figure 11B:
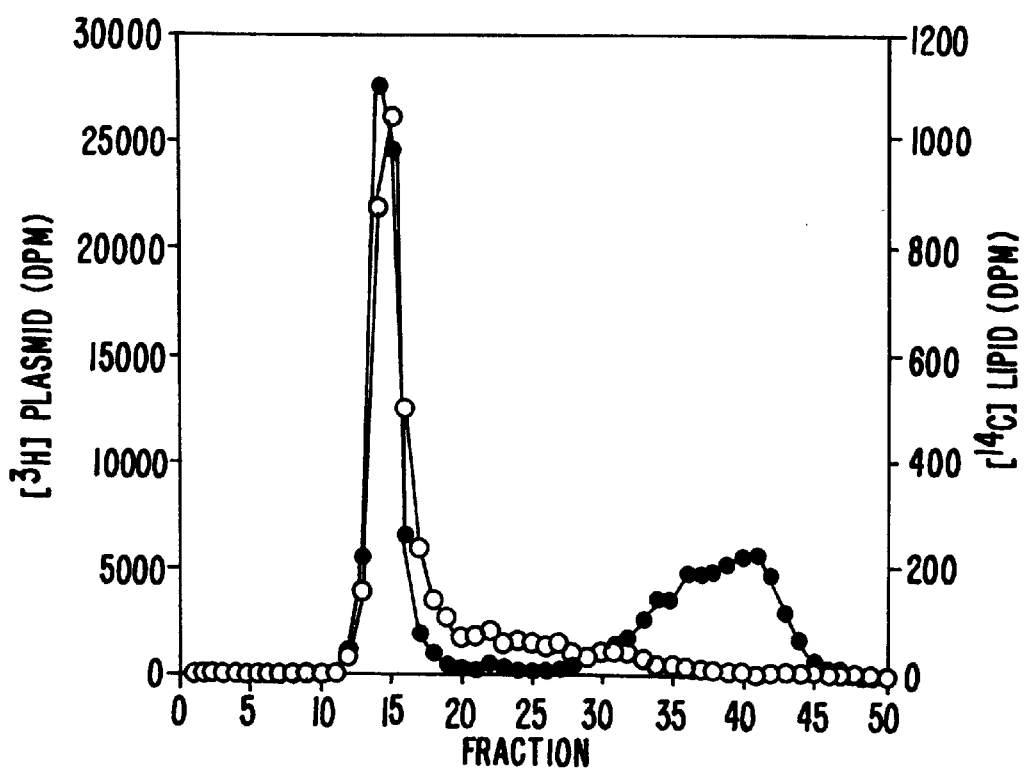

A 50 µl aliquot of a particle suspension was incubated in 500 µl of mouse serum at 37° C. for 30 min and eluted on a Sepharose CL-4B column as described above. FIG. 11 shows the elution profile of the sample after incubation in serum. As can be seen in FIG. 11A, 94% of the plasmid is recovered in the void volume suggesting that essentially all of the plasmid recovered from anion exchange chromatography was encapsulated.

To demonstrate that this experiment reflects encapsulation and not inhibition of serum nucleases by lipids in the formulation, an encapsulated plasmid DNA formulation which had not been treated by anion exchange chromatography was incubated in mouse serum for 30 min (FIG. 11B). 47% of the encapsulated plasmid DNA was eluted in the included volume while 53% was eluted in the void volume of the column. The trapping efficiency as measured by anion exchange chromatography was 55%.

EXAMPLE 4

Figure 12A:
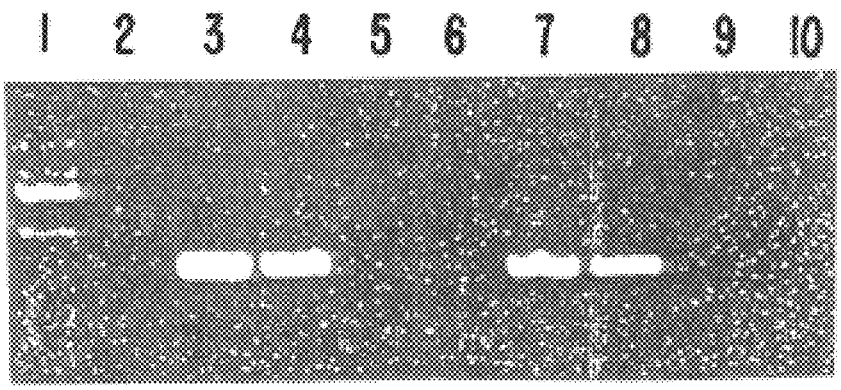
FIGS. 12A and 12B illustrate the resistance of plasmid complexed to preformed liposomes composed of DOPE:DODAC(50:50) (A) and plasmid encapsulated within DOPE:DODAC:PEG-Cer-$C_{14}$ particles (B) to digestion by DNAse I. Plasmid DNA was extracted and subjected to PCR (polymerized chain reaction) to amplify for visualization on a gel. Free plasmid was used as a control. Lane 1:1 kb DNA marker; Lane 2: PCR negative control (no DNA); Lane 3: free plasmid alone; Lane 4: free plasmid in 0.05% detergent (Triton X-100); Lane 5: free plasmid incubated with DNAse I in the absence of detergent; Lane 6: free plasmid incubated with DNAse I in the presence of detergent: Lane 7: complexed (A) or encapsulated (B) plasmid alone; Lane 8: complexed (A) or encapsulated (B) plasmid in 0.05% detergent; Lane 9: complexed (A) or encapsulated (B) plasmid incubated in DNAse I in the absence of detergent; Lane 10: complexed (A) or encapsulated (B) plasmid incubated in DNAse I in the presence of detergent.
Figure 12B:
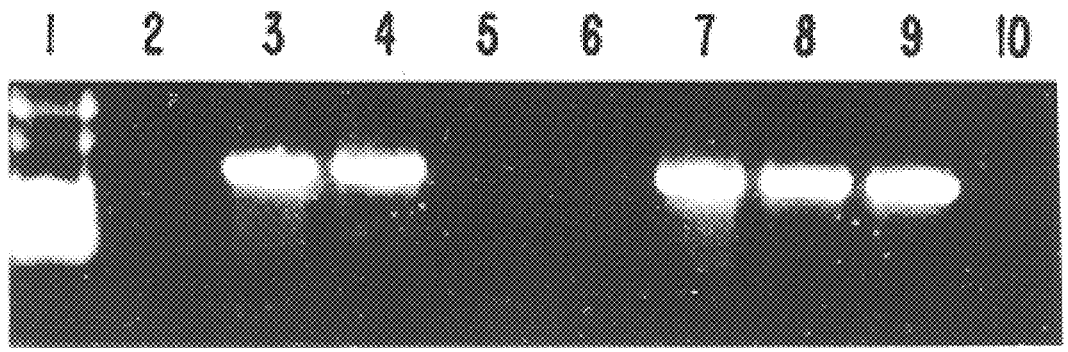

This example illustrates the in vitro resistance of the plasmid:lipid particles to DNase I digestion. Complexes formed by the addition of DOPE:DODAC (50:50) vesicles to plasmid DNA were compared to the encapsulated formulation (DOPE:DODAC:PEG-Cer-$C_{14}$; 84:6:10). The samples were incubated in Dnase I, amplified by PCR (Polymerase Chain Reaction) and run on an agarose gel. The DNA bands were visualized with ethidium bromide. The complexes were not stable in the DNase I (FIG. 12A) in the absence of detergent (lane 9) w@e the encapsulated plasmid (FIG. 12B) was stable (lane 9).

EXAMPLE 5

Figure 13:
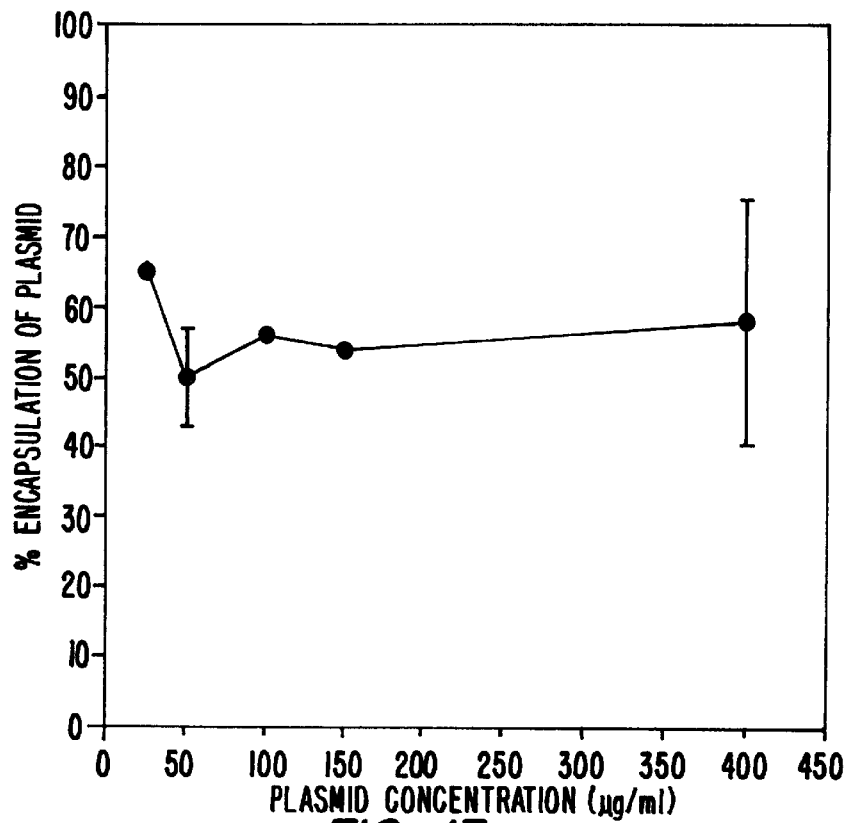
FIG. 13 illustrates the effect of plasmid DNA concentration on encapsulation efficiency (detergent dialysis). Vesicles were composed of DOPE: DODAC:PEG-Cer (84:6: 10) at a lipid concentration of 10 $\mu$mole/ml.
Figure 14:
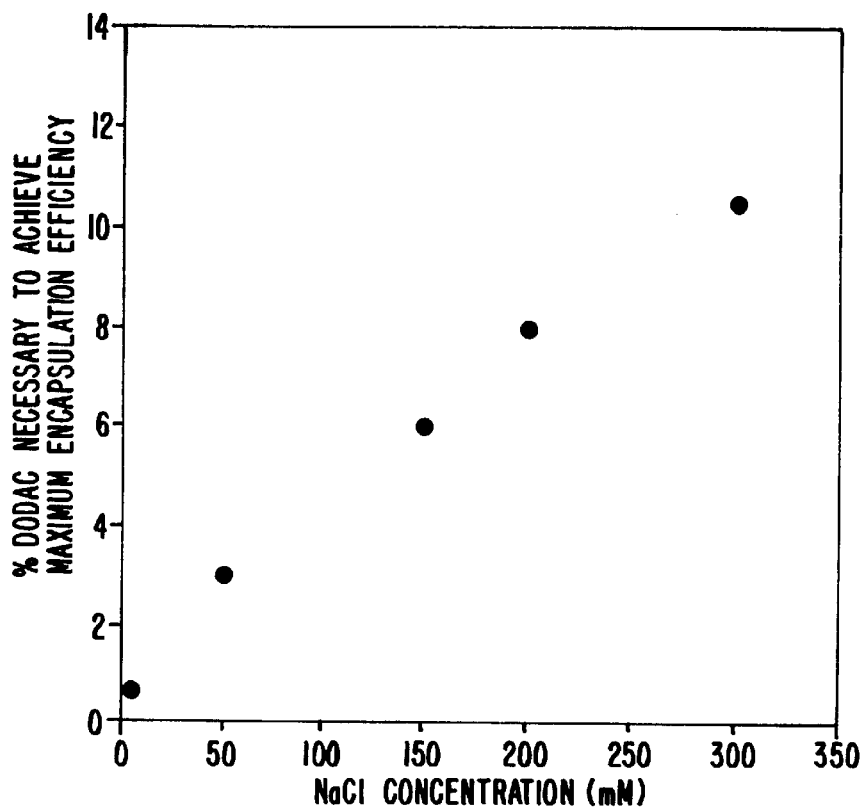
FIG. 14 illustrates the effect of NaCl concentration on the optimal DODAC concentration for plasmid entrapment. Lipid composition was DOPE:DODAC:PEG-Cer-$C_{14}$ (or PEG-Cer-$C_{20}$). PEG-Cer was held constant at 10 mole %. Total lipid concentration was 10 $\mu$mole/ml. Plasmid concentration was 50 $\mu$g/ml.

This example illustrates the dependence of plasmid concentration on encapsulation efficiency.

pCMVCAT plasmid was encapsulated in the lipid particles by detergent dialysis as described in Example 1. Encapsulation was approximately 50% –60% for all concentrations tested (FIG. 13). Encapsulation efficiency was independent of plasmid concentration over the range studied.

EXAMPLE 6

This example illustrates the dependence of optimal DODAC concentration for entrapment on NaCl concentration.

We found that the optimum DODAC concentration for entrapment was not only dependent oil the lipid composition but also was dependent on the NaCl concentration of the dialysis buffer. pCMVCAT plasmid was encapsulated in the lipid particles by detergent dialysis as described in Example 1. FIG. (14) shows the optimum DODAC concentration for encapsulation of pCMVCAT plasmid at different NaCl concentrations. Note that the amount of DODAC required in the membrane could be controlled in a predictable manner simply by changing the NaCl concentration during dialysis.

EXAMPLE 7

This example illustrates the size distribution of plasmid-lipid particles as measured by. quasielastic light scattering using a Nicomp Submicron Particle Sizer (Model 370).

Detergent Dialysis

Figure 15:
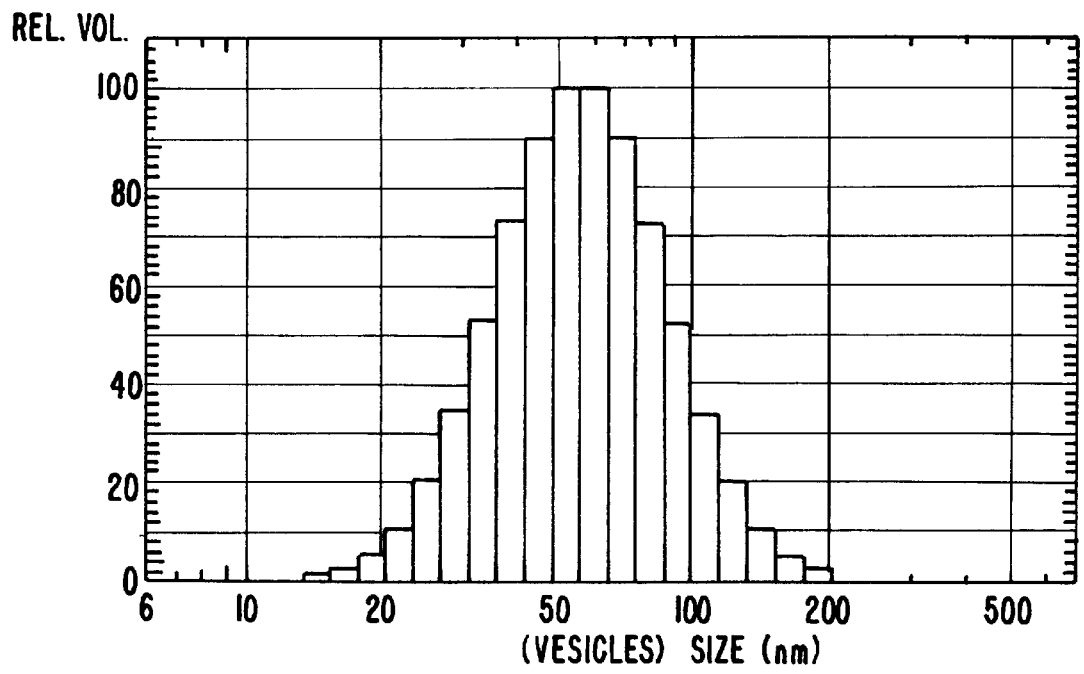
FIG. 15 illustrates the size distribution of plasmid:lipid particles prepared by the detergent dialysis procedure (Volume weighted analysis). Lipid composition was DOPE:DODAC:PEG-Cer-$C_{20}$) (84:6:10).
Figure 16:
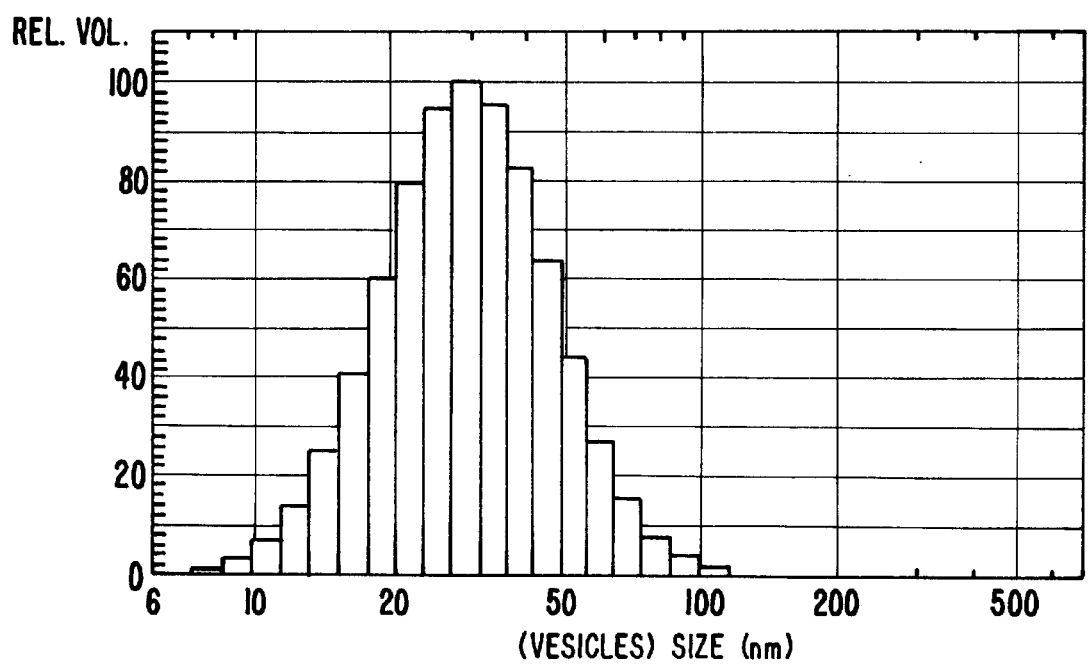
FIG. 16 illustrates the size distribution of plasmid:lipid particles prepared by the detergent dialysis procedure (Number weighted analysis). Lipid composition was DOPE:DODAC:PEG-Cer-$C_{20}$ (84:6:10).

Plasmid-lipid particles were prepared by detergent dialysis as described in Example 1. The lipid composition was DOPE:DODAC:PEO-Cer-$C_{20}$. The particles were sized using a Nicomp Submicron Particle Sizer. FIG. 15 shows the volume weighted measurement while FIG. 16 shows the number weighted measurement.

EXAMPLE 8

This example illustrates the size distribution and structure of the plasmid-lipid particles as measured by cryoelectron microscopy.

Cryoelectron microscopy is a relatively nonperturbing technique which routinely has been used to study liposome shape. Liposomes are visible in the vitreous ice layer due to the relatively electron-dense phosphate head groups. The same would apply to DNA since it consists of many phosphate groups.

Cryoelectron microscopy was performed as described previously (Chakrabarti et al., 1992; Wheeler et al., 1994). Vesicles containing plasmid DNA were enriched from the formulation by differential centrifugation. A 500 µl aliquot of the formulation was centrifuged in a microultracentrifuge for 90 min at 60,000×g. The supernatant was decanted and the pellet was resuspended in 100 ml of HBS. A drop of the suspension was placed on a 700 mesh gold grid, blotted from behind with Whatman No. 50 filter paper to form a thin film and vitrified by plunging into liquid ethane cooled with liquid nitrogen in a Reichart Jung Universal Cryo Fixation system (Reichart Corp.). The grid was transferred to a Zeiss 10C STEM electron microscope equipped with a Gatan 126 cold stage. The stage and anticontaminator were kept at 120K and 115k, respectively, with liquid nitrogen. Regions of thin vitreous ice were observed with an acceleration voltage of 60 kV.

Figure 17A:
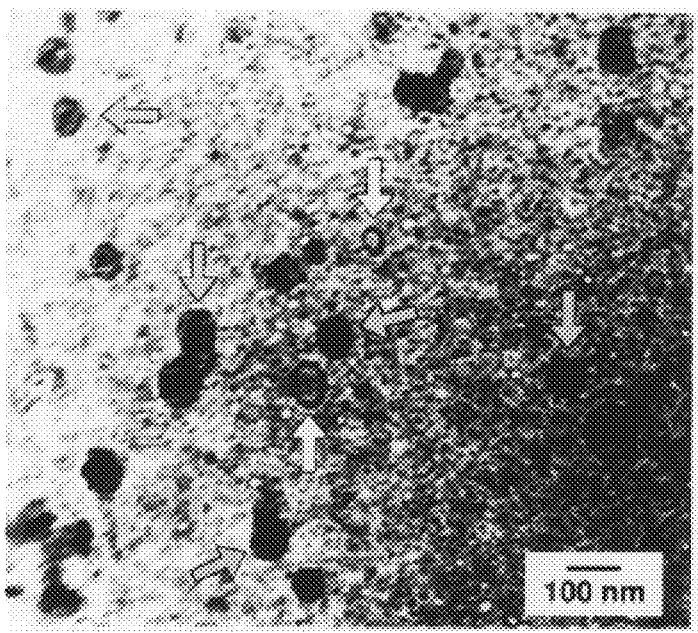
FIGS. 17A and 17B provide electron micrographs of liposomes composed of DOPE:DODAC:PEO-Cer-$C_{20}$ without encapsulated plasmid (A) and the plasmid:lipid particles (B). The small arrows denote empty liposomes approximately 100 nm in diameter. These are compared to electron-dense particles surrounded by a membrane bilayer (large arrows). Scale bar=100 nm.
Figure 17B:
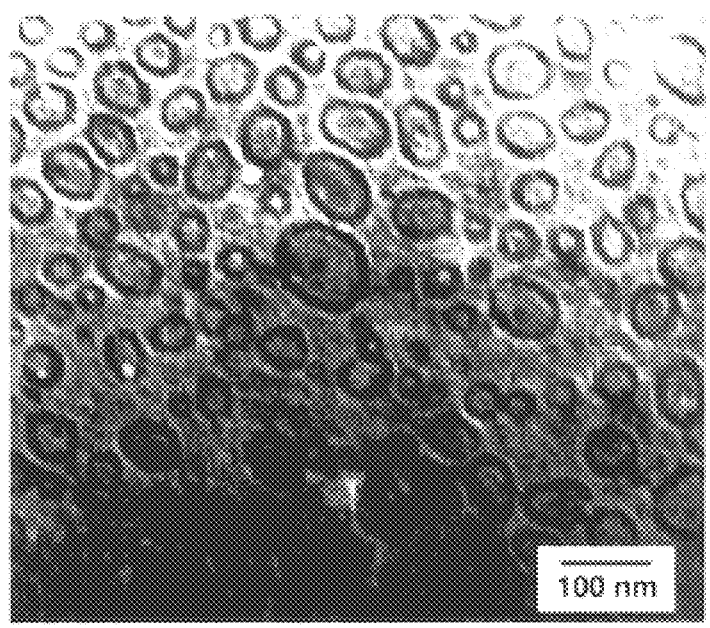

FIG. 17A is a cryoelectron microscopy picture of an encapsulated plasmid DNA formulation. For this preparation, 400 µg of plasmid DNA was used. The lipid composition was DOPE:DODAC:PEG-Cer-$C_{14}$ (84:6:10). The small arrows denote empty liposomes approximately 100 nm in diameter. These are compared to the lipid particles containing electron-dense centers (large arrows). These electron-dense centers presumably correspond to plasmid DNA. These structures were not seen in formulations made in the absence of DNA FIG. 17B.

EXAMPLE 9

This example illustrates the blood clearance of the plasmid:lipid particles in mice.

Reverse Phase

Figure 18:
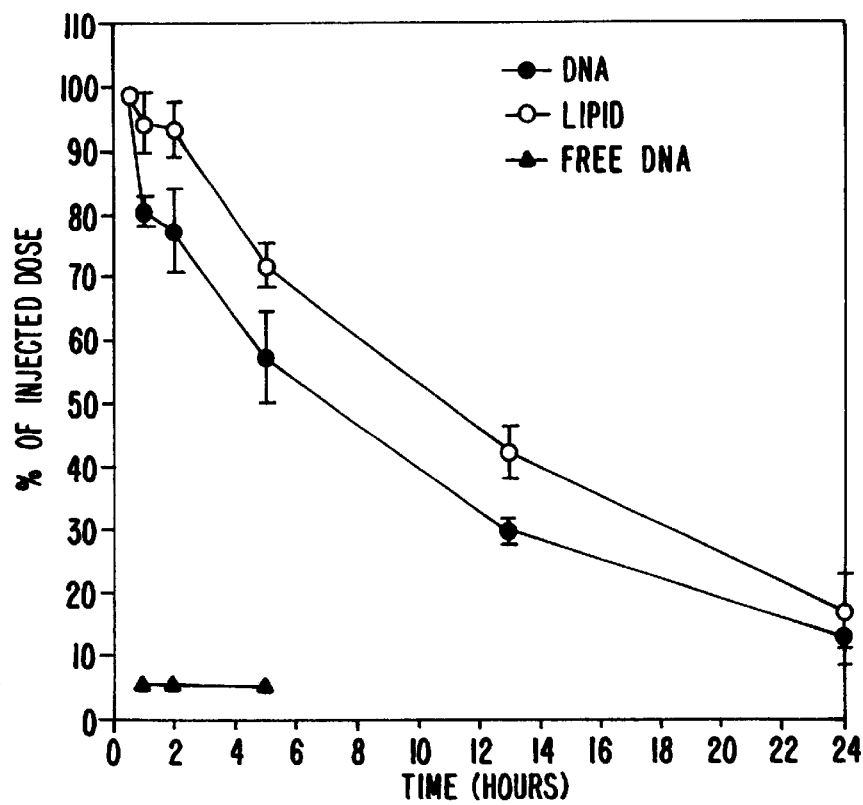
FIG. 18 shows the clearance of $^3$H-DNA and $^{14}$C-lipid from particles (prepared by reverse-phase methods) after injection into ICR mice. The figure includes free $^3$H-DNA after injection as a comparison. Lipid composition is POPC:DODAC:PEG-Cer-$C_{20}$.

Encapsulated plasmid blood clearance was tested in three ICR mire as a function of percent recovered dose over time. Percent recovery of free $^3$H-plasmid was plotted over a similar time course as a control (see FIG. 18). The encapsulated plasmid exhibits a clearance rate which is much slower than that of $^3$H-plasmid. Additionally, the plasmid:lipid ratio does not change significantly over the time course of the experiment confirming that the plasmid clearance rate is associated with the clearance rate of the lipid carrier itself.

Detergent Dialysis

Fusogenic particles of pCMVCAT encapsulated in DOPE:DODAC:PEG-Cer-$C_{14}$ or DOPE:DODAC:PEG-Cer-$C_{20}$ (84:6: 10 mole %) were prepared as follows;

pCMVCAT (50 µg)(42 of µl of $_3$H-pCMVCAT; 108 dpm/µl, 1.19 mg/ml) was incubated with DODAC in 100 µl of 1 M OGP and 400 µl of water for 30 min at room temperature. This DNA:DODAC complex mixture was added to a suspension of DOPE-PEG-Cer-$C_{14}$ or DOPE:PEG-Cer-$C_{20}$ and the particles were constructed as described in Example 1 (detergent dialysis). The plasmid:lipid particles for blood clearance studies contained 0.75 µl of $^{14}$C-cholesteryl hexadecyl ether (CHE) (6.66 µl/µCi) in I 00 µl of I M OGP and 400 µl of water.

Clearance of pCMVCAT encapsulated in DOPE:DODAC:PEG-Cer-$C_{14}$ and DOPE:DODAC.PEC-Cer-$C_{20}$(84:6:10).

External "encapsulated" DNA was removed by anion exchange chromatography using DEAE Sepharose CL-6B prior to injection into mice. Encapsulation efficiencies were approximately 42% for the systems containing PEG-Cer-$C_{20}$ and 60% for the systems containing PEG-Cer-Cer,$_{14}$.

Three groups of three female ICR mice (20–25 g) were injected with 200 µl of DNA-encapsulated with the plasmid:lipid particle. One group of mice was sacrificed and blood was taken at each of three time points (1, 2 and 5 hours). The plasma was separated from whole blood by centrifugation in 0.5 ml EDTA coated Tainer tubes. A 200 µl aliquot of the plasma from each mouse was assayed for $^3$H-DNA and $^{14}$C-lipid by scintillation counting.

Figure 19A:
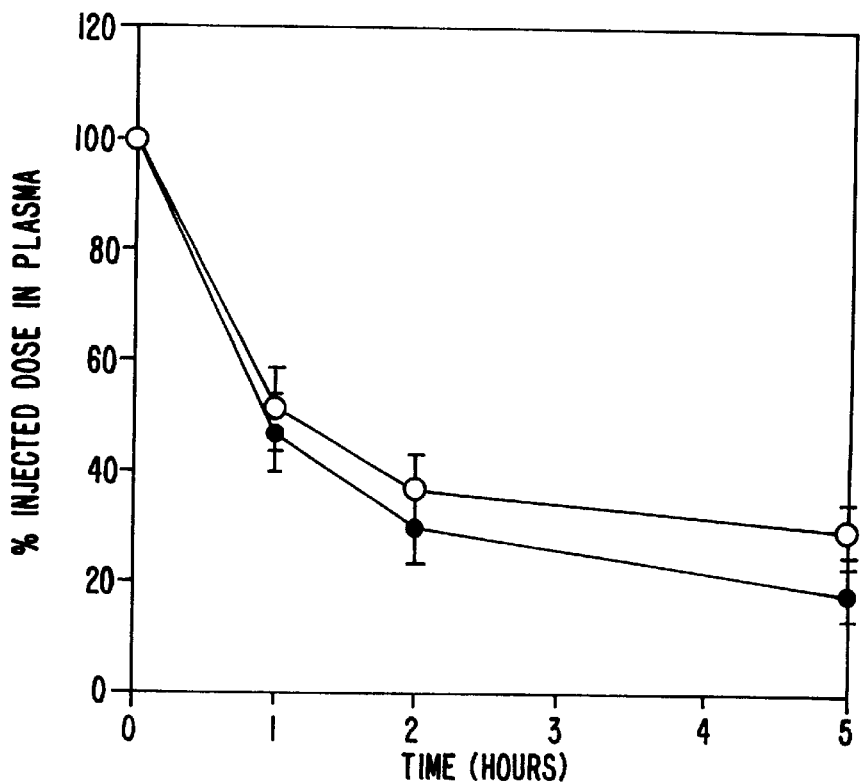
FIGS. 19A and 19B show the clearance $^3$H-DNA and $^{14}$C-lipid from particles (prepared by detergent dialysis methods) after injection into ICR mice. Lipid compositions were (A) DOPE:DODAC-PEG-Cer-$C_{20}$ (84:6:10) and (B) DOPE:DODAC-PEG-Cer-$C_{14}$ (84:6:10).

FIG. 19A shows the Clearance of DNA encapsulated in a particle composed of DOPE:DODAC:PEG-Cer-$C_{20}$ (84:6:10). The DNA and lipid were cleared much less rapidly from the circulation than when the DOPE:DODAC:PEG-Cer-$C_{14}$ composition was used. Nearly 50% of the lipid and DNA are present after 2 hour. A significant amount of DNA and lipid were still present after 5 hours. The amount of DNA and lipid injected was 1.8 µg and 853 µg, respectively.

Figure 19B:
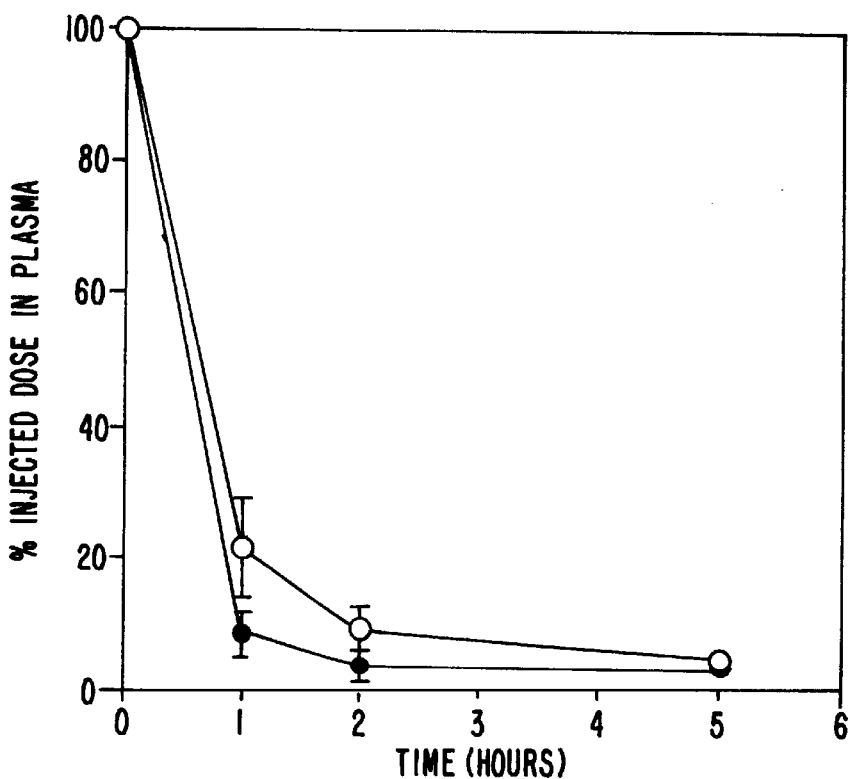

FIG. 19B shows the clearance of DNA encapsulated in particle composed of DOPE:DODAC:PEG-Cer$_{14}$ (84:6: mole %). Both DNA and lipid are cleared rapidly from the circulation with only about 20% of the lipid and 10% of the DNA present in the plasma after 1 hour. The amount of DNA and lipid injected was 2.7 µg and 912 µg, respectively.

EXAMPLE 10

This example illustrates the in vitro transfection of BHK cells grown in tissue culture.

EXAMPLE 11

This example illustrates the in vivo transfection of tissues in mice.

In vivo Transfection in Lung, Liver and Spleen

Three groups of four ICR mice were injected via tail vein with pCMVCAT encapsulated in lipid particles composed of DOPE:DODAC:PEG-Cer-$C_{14}$ (84:6:10) or DOPE:DODAC:PEG-Cer-$C_{20}$, prepared as described in Example 7, The mice were sacrificed after 2, 4 and 8 days and the lung, liver and spleen were assayed for CAT activity according to a modification of Deigh, *Anal. Biochem.,* 156:251–256 (1986). The amount of plasmid injected was 2.6 μg for the particles containing PEG-Cer-C$_{14}$ and 1.5 μg for the particles containing PEG-Cer-C$_{20}$.

Figure 20:
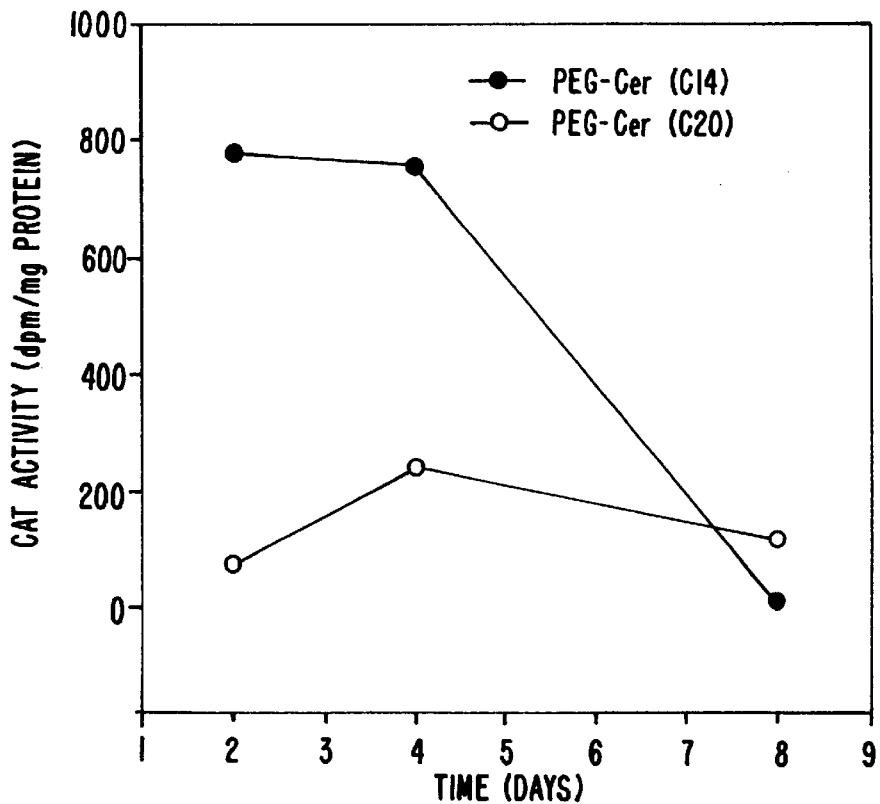
FIG. 20 shows the results of in vivo gene transfer which occurs in the lungs of mice. Lipid composition is DOPE-DODAC-PEG-Cer-$C_{20}$ or DOPE:DODAC:PEG-Cer-$C_{14}$ (84:6: 10).

FIG. 20 shows the results of in vivo transfection achieved in the lung. As can be seen from this figure, treatment with DOPE:DODAC:PEG-Cer-C$_{14}$ resulted in transfection (based on CAT activity) up to 4 days. DOPE:DODAC:PEG-Cer-C$_{20}$ while resulting in overall lower levels of CAT activity), provided relatively constant levels of enzyme activity over 8 days.

Figure 21:
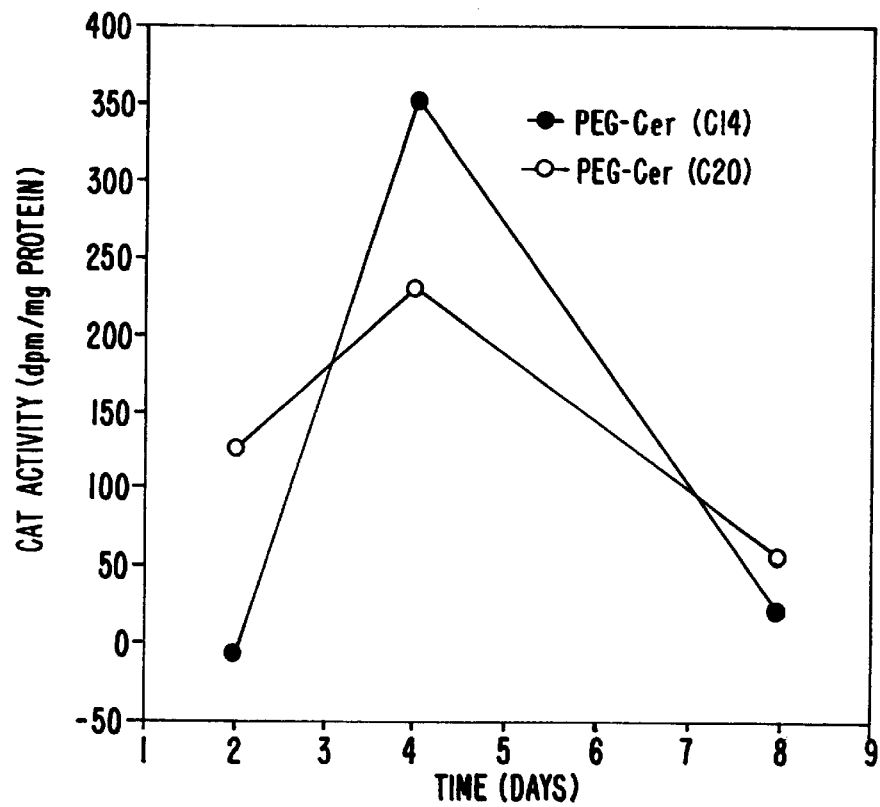
FIG. 21 shows the results of in vivo gene transfer which occurs in the liver mice. Lipid composition is DOPE-DODAC-PEG-Cer-$C_{20}$ or DOPE:DODAC:PEG-Cer-$C_{14}$ (84:6: 10).

FIG. 21 shows the results of transfection achieved in the liver. For both formulations, transfection (and CAT activity) reached a maximum at 4 days.

Figure 22:
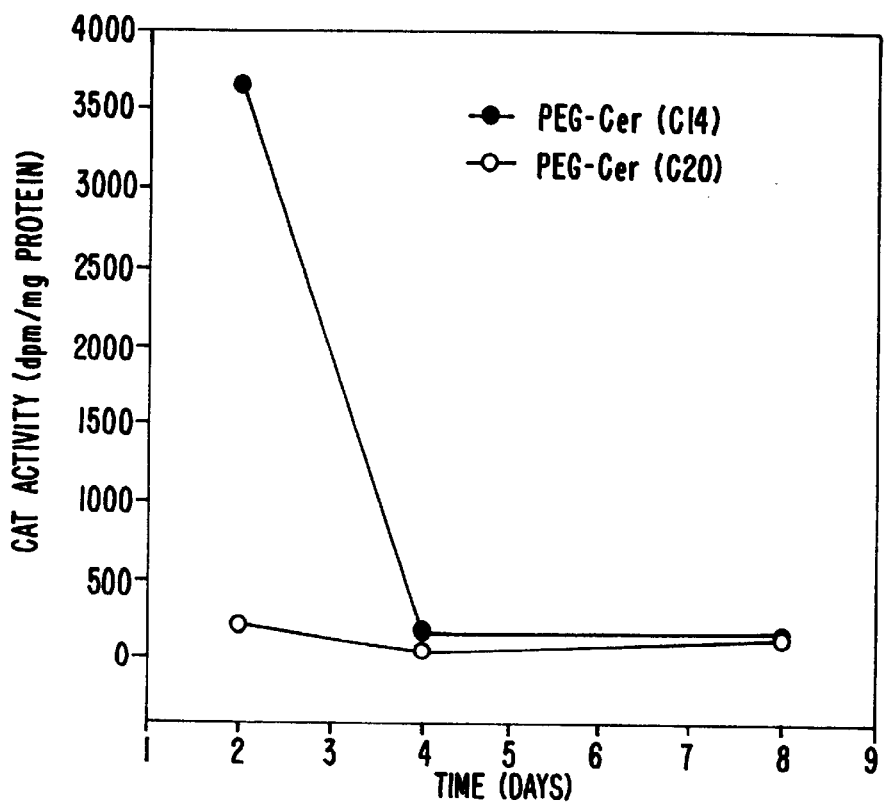
FIG. 22 shows the results of in vivo gene transfer which occurs in the spleen of mice. Lipid composition is DOPE-DODAC-PEG-Cer-$C_{20}$ or DOPE:DODAC:PEG-Cer-$C_{14}$ (84:6:10).

FIG. 22 shows the results of transfection achieved in the spleen wherein the maximum transfection was found for both formulations to occur after 2 days.

Examples 12–18 illustrate the formation and characterization of charge-neutralized lipid-nucleic acid intermediate complexes, in which the nucleic acid adopts hydrophobic character. In each of these examples, the term "DNA" or "plasmid" refers to the plasmid pCMVβ. Examples 19 and 20 illustrate the preparation and characterization of lipid-nucleic acid particles which are suitable for transfection of cells. Examples 21–23 illustrate the serum stability and transfecting ability of these lipid-nucleic acid particles.

EXAMPLE 12

This example provides a comparison of cationic lipids and non-cationic lipids in effecting the formation of hydrophobic charge-neutralized lipid-nucleic acid complexes.

Figure 23:
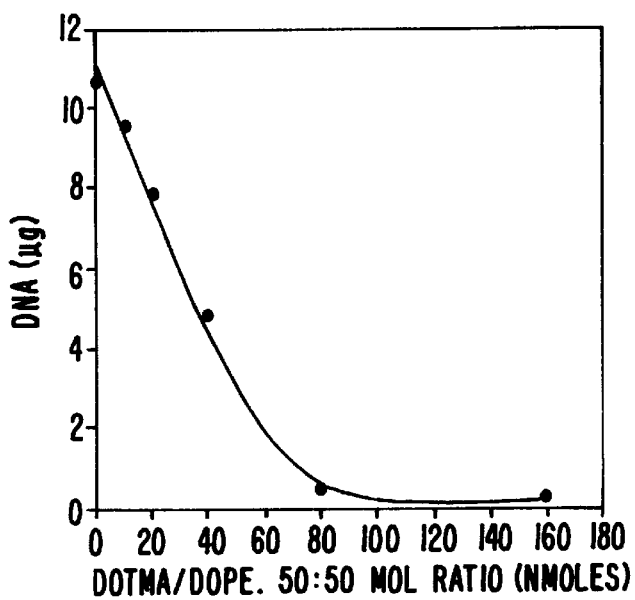
FIG. 23 shows the effect of increasing amounts of LIPO-FECTIN® (DOTMA/DOPE; 50:50 mol ratio) on the recovery of $\beta$gal plasmid DNA in the aqueous phase following Bligh and Dyer extraction of the lipid-nucleic acid complexes.

LIPOFECTIN® consists of sonicated unilamellar vesicles composed of DOTMA and DOPE (50:50 mole ratio, see, Felgner, et al., Proc. Natl. Acad. Sci, USA 84:7413–7417 (1987)). The liposomes are prepared in water and are provided at a total lipid concentration of 1 mg/mL. DNA (10 μg) was mixed with the liposomes in water, as described below in Example 2, to provide from 0 to 160 nmoles total lipid. Each of the mixtures was extracted using the Bligh and Dyer procedure. Surprisingly, in the presence of LIPOFECTIN®, there was a concentration dependent reduction in DNA recovered from the aqueous phase (see FIG. 23). Addition of 80 nmoles of total lipid to 10 μg DNA resulted in greater than 95% loss of DNA from the aqueous phase. This effect could not be achieved using liposomes prepared from egg phosphatidylcholine/DOPE (50:50 mole ratio). Thus, the hydrophobic complex which forms and is drawn into the organic phase is a result of the cationic lipid present in the complex.

EXAMPLE 13

This example provides a comparison of several cationic lipids in forming hydrophobic, charge-neutralized lipid-nucleic acid complexes which partition into organic solvents.

Figure 24A:
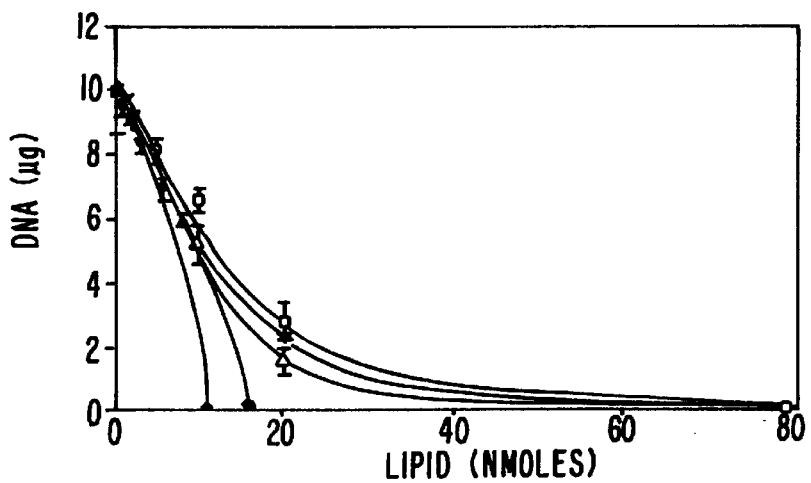
FIGS. 24A and 24B show the effect of increasing amounts of cationic lipid on the recovery of plasmid DNA in the aqueous (A) and organic (B) phase following Bligh and Dyer extraction of the lipid-nucleic acid complexes.
Figure 24B:
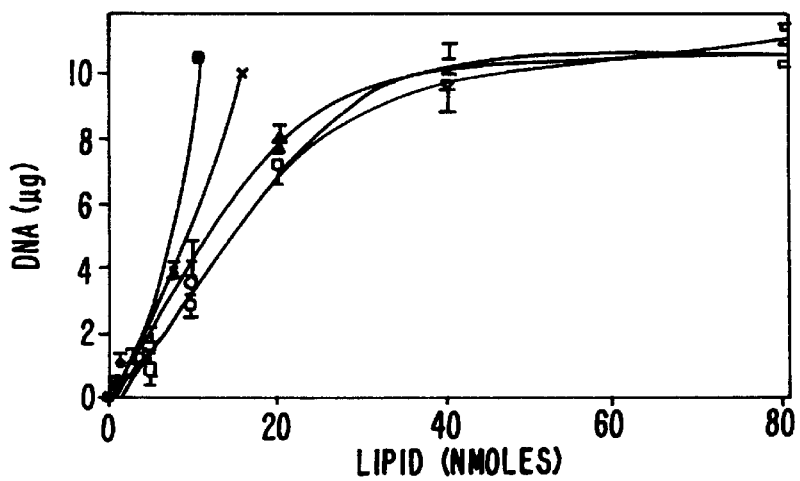

Purified monovalent cationic lipids (DOTMA, DDAB and DODAC) were each added to DNA in a Bligh and Dyer monophase solvent system. The resulting mixtures were each partitioned into two phases by the addition of water and chloroform. Plasmid DNA levels were determined in the aqueous and organic phases as described above. The results are presented in FIG. 24, and are consistent with the results presented in FIG. 23. In particular, there was found to be a cationic lipid dependent loss of DNA from the aqueous phase (FIG. 24A). There was no visible evidence of precipitated material at the aqueous/organic interface and quantification of the DNA in samples collected to include the interface did not account for appreciable DNA levels (results not shown). The DNA was found to be quantitatively transferred to the organic phase (FIG. 24B). Additionally, greater than 95% of the DNA in the monophase could be recovered in the organic phase when 40 nmoles monovalent cationic lipid was added. This value is identical to results presented in FIG. 23 in which 80 nmoles of LIPOFECTIN® (50 mol % DOTMA) resulted in the complete loss of DNA from the aqueous phase. The results presented in FIG. 24 indicate that the three different monovalent cationic lipids behave in a similar fashion under the conditions used.

EXAMPLE 14

This example illustrates the influence of multivalent cationic lipids and cationic nonlipid species on DNA partitioning into organic solvents.

LIPOFECTAMINE® (DOSPA:DOPE, 75:25 mol ratio), and TRANSFECTAM® (100% DOGS) were added to DNA (10 μg) as preformed liposomes, as described in Example 13. The liposomes contain headgroups derived from spermine and exhibit positive charges of 5 and 4, respectively at pH <7. As expected, significantly lower amounts of these lipids (calculated on the basis of moles) are required to mediate DNA partitioning into the organic phase (see FIG. 24). Complete partitioning of the DNA into the organic phase was achieved after addition of approximately 10 nmoles DOSPA and DOGS.

Figure 25A:
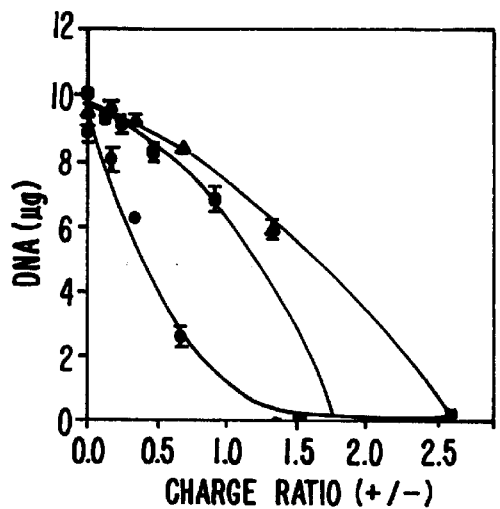
FIGS. 25A, 25B, 25C and 25D show the recovery of plasmid DNA from aqueous (A and C) and organic (B and D) fractions following Bligh and Dyer extraction and expressed as a function of charge ratio (+/−).
Figure 25B:
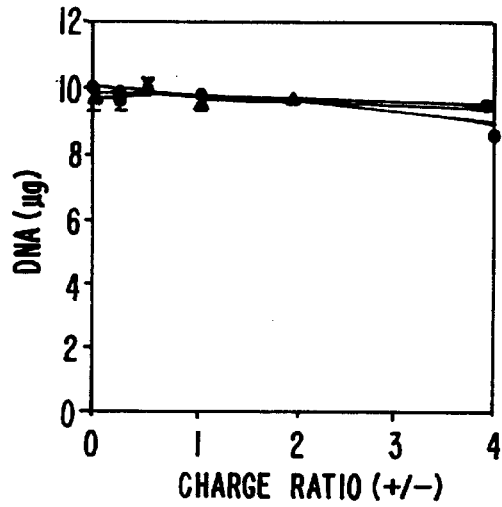
Figure 25C:
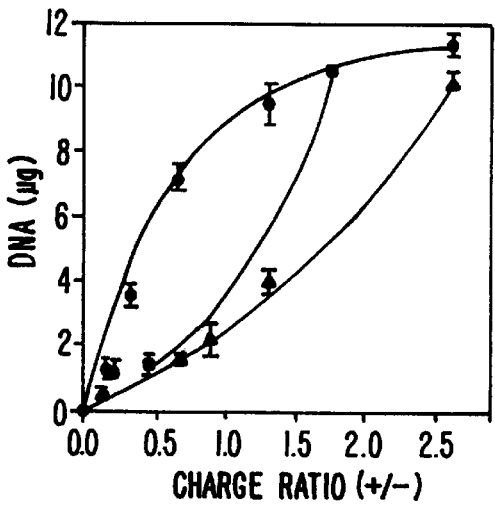
Figure 25D:
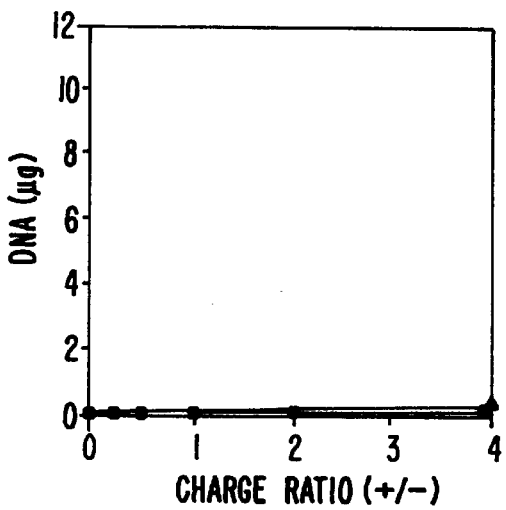

Previous studies have demonstrated that DNA condenses into small toroid or rod shaped structures when the DNA phosphate charge is at least 90% neutralized (see Wilson, et al., Biochemistry 18:2192–2196 (1979). The data presented in FIG. 24 was therefore expressed as a function of cation/phosphate charge ratio (FIGS. 25A and 25B). For comparison, results obtained after the addition of the nonlipid-based monovalent (lysine), divalent (calcium) and multivalent (poly-L-lysine) cations are included (FIGS. 25C and 5D). The results shown in FIG. 25 demonstrate that for monovalent cationic lipids, greater than 99% of the DNA partitioned into the organic phase when a +/− charge ratio >1 was achieved. Similar results were observed when the polyvalent lipids DOSPA and DOGS were used, although a slightly greater charge ratio was required to mediate efficient DNA transfer. However, DNA partitioning into the organic phase did not occur as a result of simple charge neutralization. When the DNA was mixed with the nonlipid cations, at charge ratios up to and in excess of 4, the majority of the DNA was invariably recovered in the aqueous phase.

EXAMPLE 15

This example illustrates that the hydrophobic, charge-neutralized lipid-nucleic acid complexes formed as described in Examples 12–14 provide the nucleic acid in an uncondensed (unprotected) configuration.

Figure 26A:
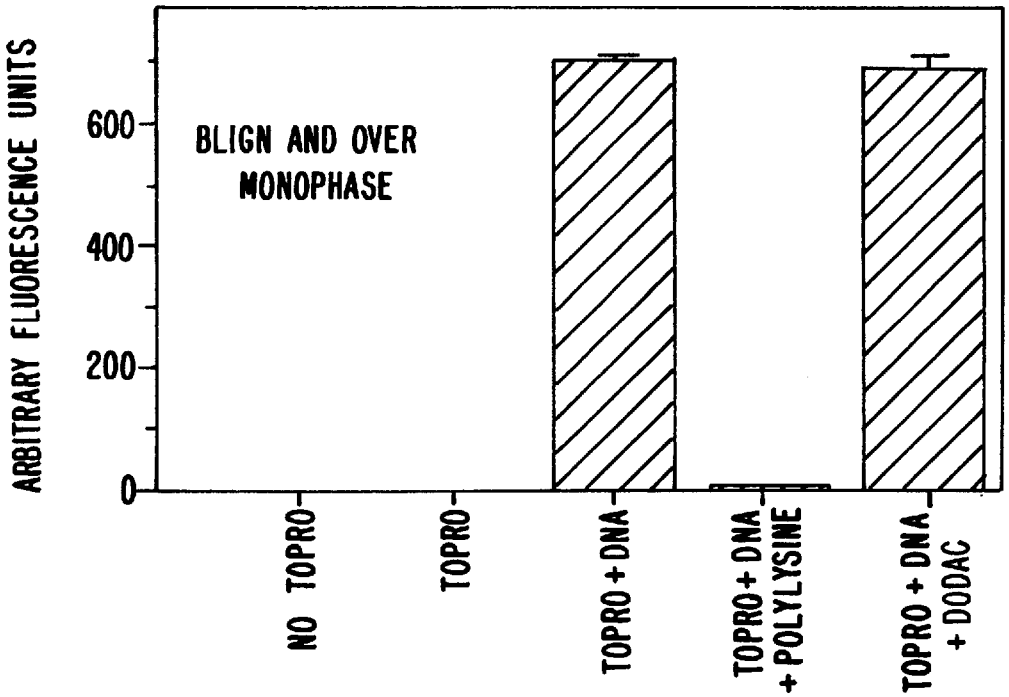
FIGS. 26A and 26B illustrate the DNA condensation by poly-L-lysine and DODAC assayed by TO-PRO-1 dye intercalation. Condensation state was assessed in a Bligh and Dyer monophase (A) and in 100 mM OGP (B).
Figure 26B:
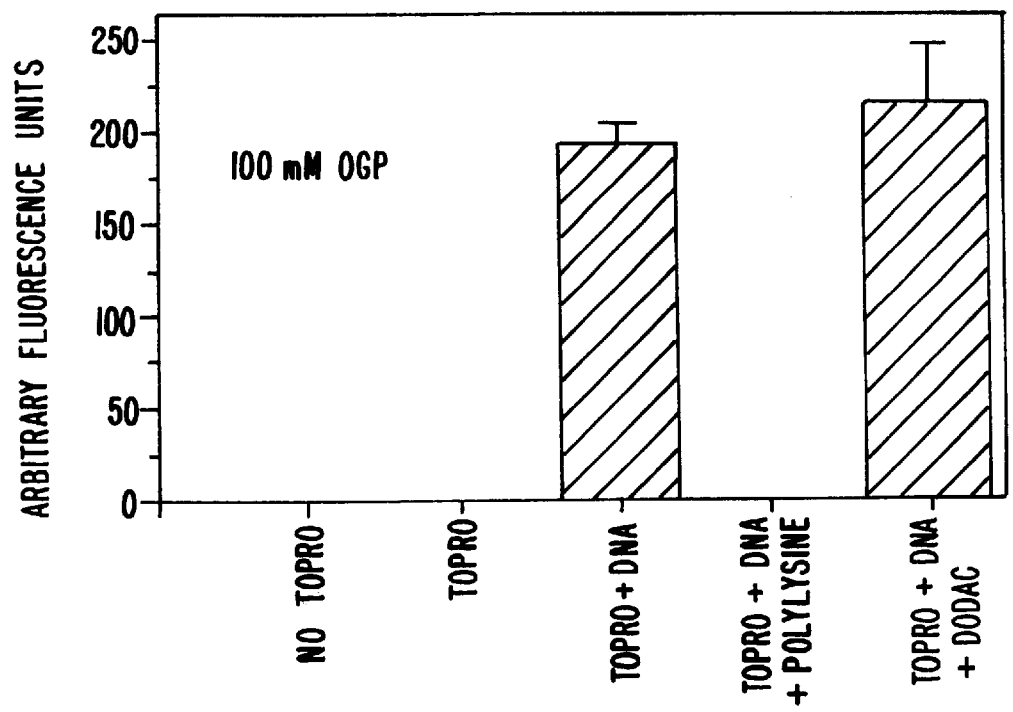

Evaluation of the hydrophobic, charge-neutralized lipid-nucleic acid complexes was carried out by assessing the ability of a small fluorescent probe to bind to the nucleic acid in the complex. This evaluation is similar to an approach using ethidium bromide (see Gershon, et al., Biochemistry 32:7143–7151 (1993)). TO-PRO-1 is a more sensitive, membrane impermeable, nucleic acid intercalating dye and therefore, provides a more stringent test of DNA binding. DNA was mixed with either a monovalent cationic lipid or poly-L-lysine in the Bligh and Dyer monophase (FIG. 26A). TO-PRO-1 was then added to a final concentration of 1 μM and fluorescence was measured at 533 nm (probe excitation at 509 nm). In the absence of DNA no fluorescence was observed. However, when plasmid DNA was added (10 µg/mL) there was a >600 fold increase in fluorescence at 533 nm. When TO-PRO-1 was added to the DNA/poly-1-lysine mixture, no fluorescence was observed. This is consistent with the existence of the DNA in a condensed state due to charge neutralization. In dramatic contrast, addition of TO-PRO-1 to a hydrophobic charge-neutralized lipid-nucleic acid complex (plasmid/DODAC complex), TO-PRO-1 binding was not excluded. This result is consistent with the concept that DNA within the hydrophobic complex does not exist as a condensed structure. FIG. 26B shows that similar results were obtained when TO-PRO-1 was added to plasmid DNA mixed with either poly-L-lysine or the cationic lipid DODAC in the presence of 100 mM OGP, a nonionic detergent.

EXAMPLE 16

Figure 27:
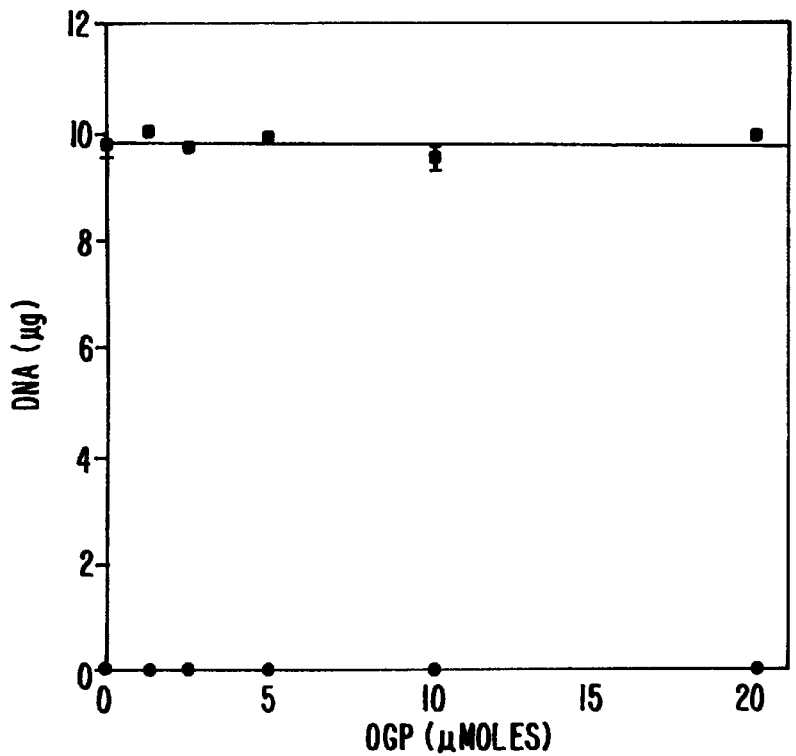
FIG. 27 illustrates the effects of increasing amounts of OGP on the recovery of plasmid DNA from the aqueous and organic phases following Bligh and Dyer extraction of lipid-nucleic acid complexes (plasmid/DODAC).
Figure 28:
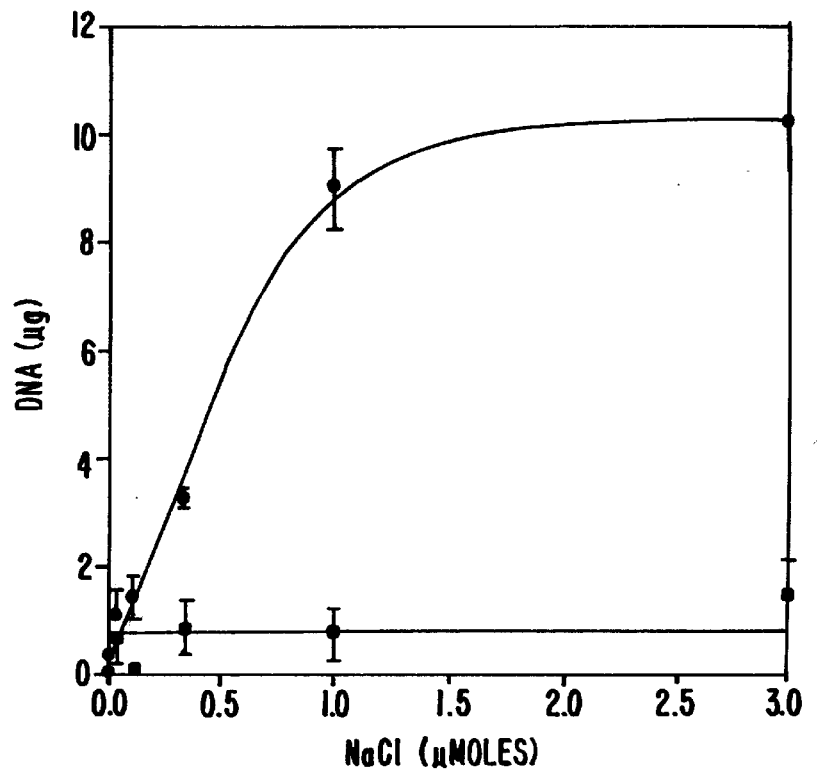
FIG. 28 shows the effects of increasing amounts of NaCl on the recovery of plasmid DNA from the aqueous phase following Bligh and Dyer extraction of lipid-nucleic acid complexes.

This example illustrates the stability of the hydrophobic, charge-neutralized lipid-nucleic acid complex in detergent solutions (FIG. 27) and instability in the presence of added salts (FIG. 28).

Plasmid DNA (10 µg) was mixed with 40 nmoles of DODAC in a Bligh and Dyer monophase as described in Example 12. OGP was added to achieve concentration up to 20 mM (20 µmoles in 1 mL) prior to separating the sample into two phases. This concentration was the maximum amount which could be added from a 2 M stock solution of OGP without disrupting the monophase system. Regardless of the OGP concentration, greater than 99% of the DNA partitioned into the organic phase, demonstrating the stability of the hydrophobic, charge-neutralized complexes.

The effect of increasing concentrations of NaCl on the stability of the hydrophobic, charge-neutralized lipid-nucleic acid complex was also evaluated. As illustrated in FIG. 28, monovalent cationic lipid binding to DNA was completely inhibited in the presence of 1 µmole NaCl. At this level, $Na^+$ is present in a 25 molar excess relative to the amount of cationic lipid added. As expected, the complex between DNA and the polyvalent lipid DOSPA was more stable in the presence of NaCl. In fact, addition of $Na^+$ in a 300-fold molar excess relative to DOSPA did not cause partitioning of the charge-neutralize lipid-nucleic acid complex into the aqueous phase.

EXAMPLE 17

This example illustrates the influence of cationic lipid binding on DNA migration by agarose gel electrophoresis.

Figure 29A:
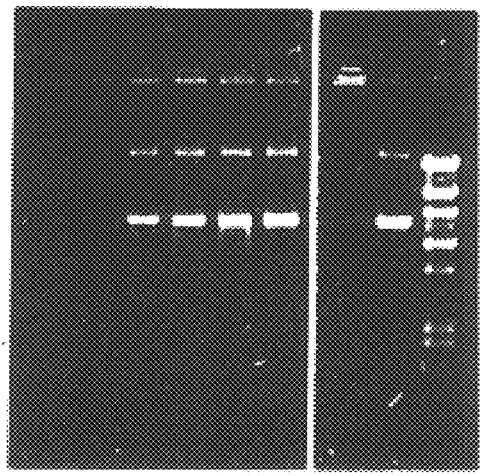
FIGS. 29A and 29B show the effect of poly-L-lysine and DODAC on the electrophoretic mobility of plasmid DNA.

FIG. 29A shows the gel mobility characteristics of the charge-neutralized lipid-nucleic acid complexes made in the presence of OGP compared to that of the poly-L-lysine condensed DNA control. Lane 2 shows that the nonlipid-based DNA/poly-L-lysine complexes exhibit significantly reduced mobility in an agarose gel. This result is consistent with studies which have demonstrated that DNA condensed with cationic liposomes adopt a macromolecular structure that does not move within an applied electric field (see, Bertling, et al., Biotechnol. Appl. Biochem. 13:390–405 (1991)). This effect may be a consequence of charge neutralization and/or increases in molecular size. In contrast, when DNA is mixed with cationic lipids under conditions of Example 12, there is no indication that the migration of DNA has been altered (see FIG. 29A, lanes 3–5). These studies provide further evidence suggesting that cationic lipid binding to DNA using the methods of the present invention does not result in the condensation of DNA. Changes in DNA mobility were observed, however, when the cationic lipid concentration was increase beyond cationic lipid to DNA phosphate charge ratios of 2 (see lanes 6 to 8). For example, addition of 320 nmoles of DODAC resulted in a decrease in DNA migrating into the gel and a small proportion of the DNA migrating near the top of the gel. This indicates that condensation of DNA can be achieved with excess cationic lipids.

EXAMPLE 18

This example illustrates the ability of cationic lipids to protect plasmid DNA from enzymatic digestion.

Figure 29B:
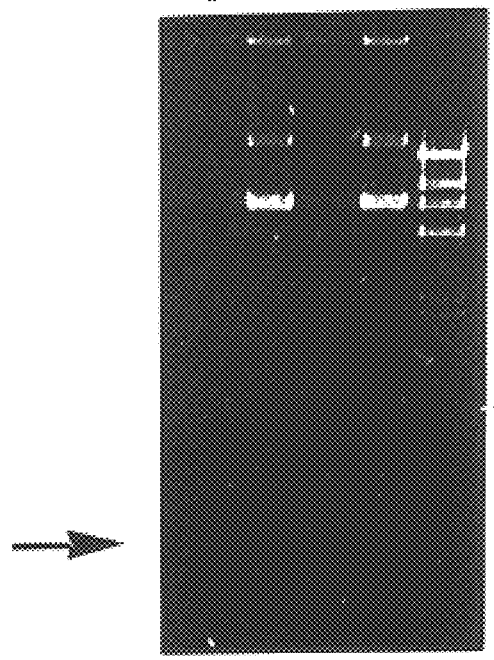

To determine the ability of cationic lipids to protect plasmid DNA from enzymatic digestion, DNase I mediated degradation of the lipid-nucleic acid complex (plasmid/DODAC complex prepared as described above) was also evaluated using agarose gel electrophoresis (see FIG. 29B). In these experiments, plasmid in OGP solution was mixed with a sufficient amount of DNase I to generate small DNA fragments after a 10 min incubation at 37° C. (lane 2). Lane 1 shows undigested plasmid as a control. Using identical, conditions, the complexes (plasmid complexed with the monocationic lipid DODAC) was not protected against the enzymatic activity of DNase I (lane 4). DNA extracted from the complex in the absence of DNase I (lane 3) shows intact DNA. This provides further evidence that the nucleic acids in the lipid-nucleic acid complexes is in an uncondensed state and is susceptible to degradation.

EXAMPLE 19

This example illustrates the preparation of lipid-nucleic acid particles of β-gal, DODAC and ESM.

Figure 31A:
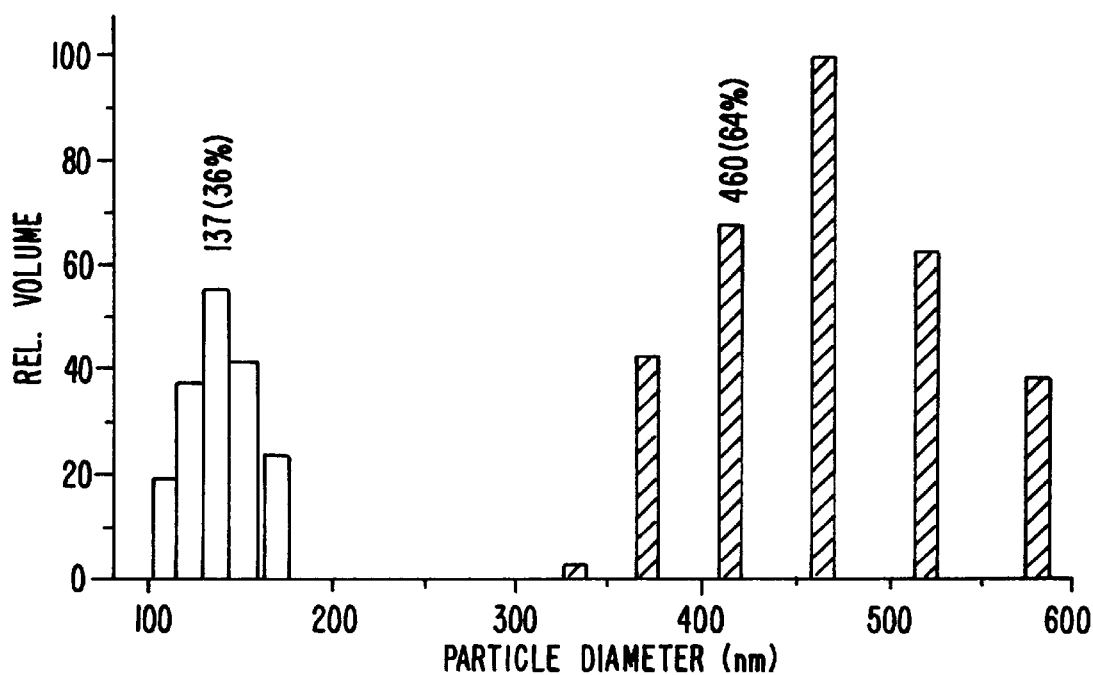
FIGS. 31A and B are bar graphs which illustrates the QELS results of a typical lipid-nucleic acid complex mixture prepared from $\beta$-gal plasmid/DODAC/ESM.
Figure 31B:
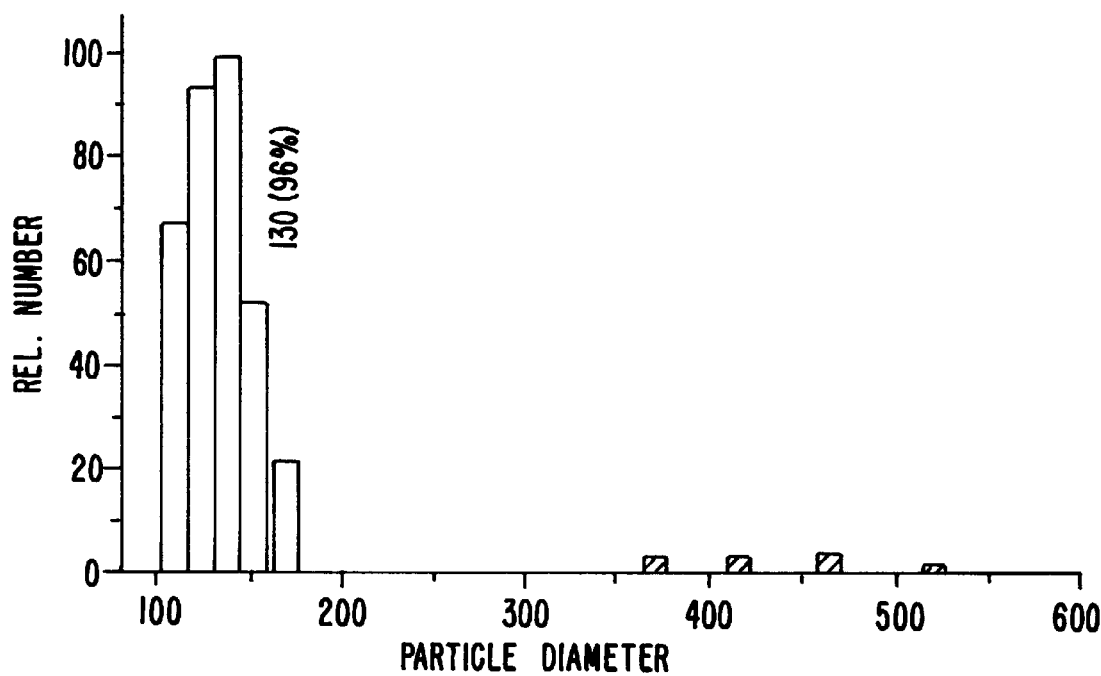

Cationic lipid DODAC, non-cationic lipid ESM, and nucleic acid β-gal plasmid were formulated using a detergent dialysis method according to the "strategy of reverse order" (see FIG. 30) as follows:

Individual solutions of DNA (10 µg in 200 µL of 200 mM aqueous OGP), DODAC (160 nmoles in 400 µL OGP) and ESM (160 nmoles in 400 µL OGP) were prepared. The ESM and DODAC solutions were each sonicated at low power at 10–20 pulses. The DNA solution was then added to the ESM solution and the mixture was allowed to incubate for 0.5 hr at room temperature. The DODAC solution was added slowly to the DNA/ESM mixture while vortexing the mixture at low speed. The resultant mixture (1 mL) was placed in a SPECTRA/POR, mwco: 12–14,000 dialysis tube (Fisher Scientific) and dialyzed against six changes of 2 L of distilled sterile water over 36 hours. Size distribution of the complexes formed was determined using quasielastic light scattering (QELS) technique (Nicomp 370 particle sizer operating at a wavelength of 632.8 nm). FIG. 31 shows that two populations of particles were observed, one group sized from 50 to 150 nm and the second sized 500 to 1000 nm. The relative numbers of each depended on the type of non-cationic lipid(s) used, the amount and concentration of the two lipid components, and the DNA/lipid ratio. About 20–40% of the relative volume of the mixture were the smaller sized complexes which accounted for over 90% of the total particle number.

EXAMPLE 20

This example illustrates the state of condensation of the DNA in the lipid-nucleic acid particle.

Figure 32:
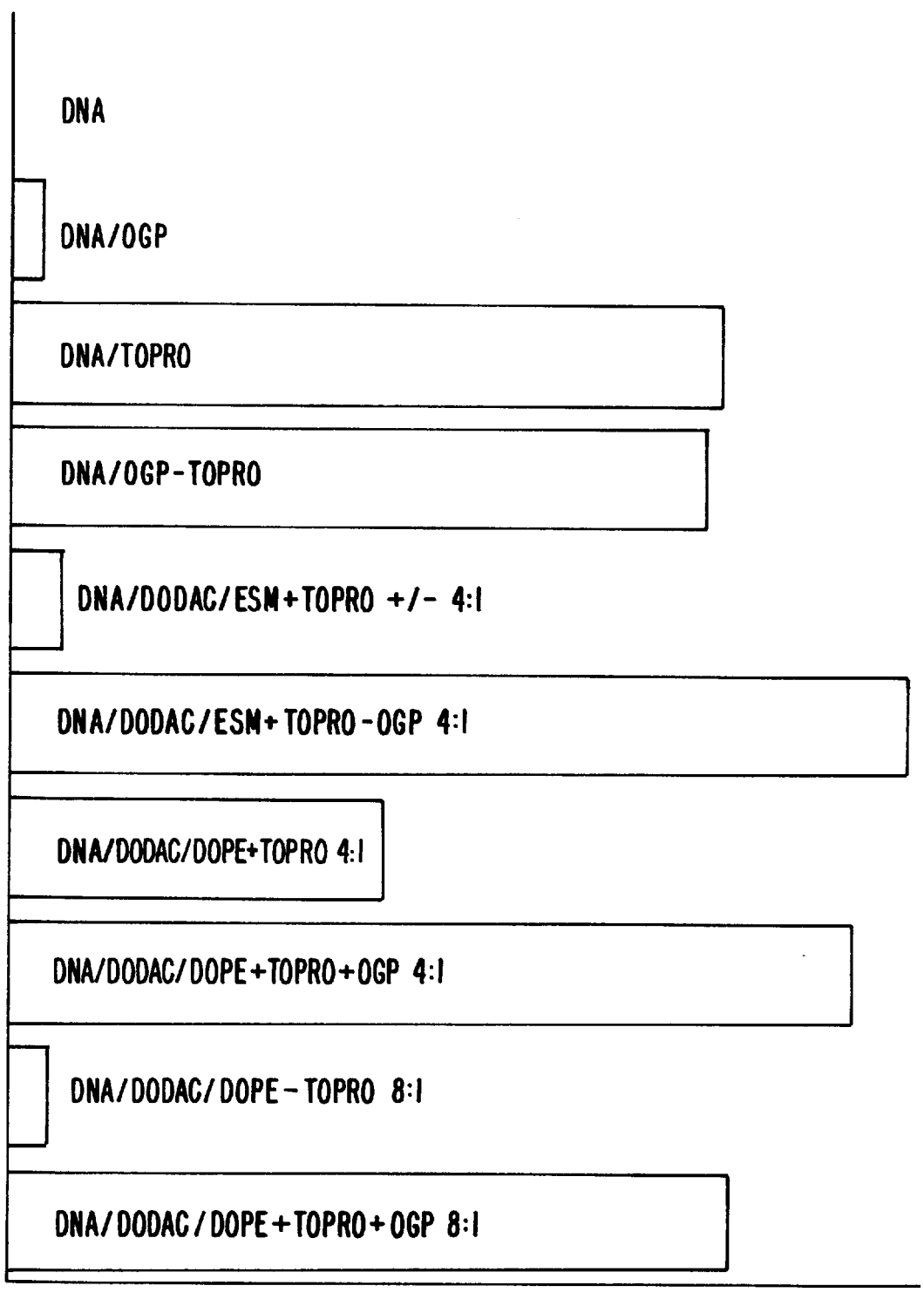
FIG. 32 is a bar graph which illustrates the fluorescence spectroscopic evaluation of DNA condensation in the lipid-nucleic acid complexes using TO-PRO-1 dye intercalation. The results show that $\beta$-gal plasmid in DODAC/ESM is condensed and protected against dye intercalation by the lipid, and that OGP can uncondense the particle.

The fluorochrome (TO-PRO-1) was used to evaluate the state of condensation of the DNA in the lipid-nucleic acid particle. A 200 µL aliquot of the lipid-nucleic acid particle (containing 2 µg plasmid DNA prepared with the protocol given in Example 19) was diluted to 1 mL with 100 mM OGP. TO-PRO-1 was added to make a final concentration of 1 µM. To measure fluorescence, spectrofluorometric measurements were performed using a Luminescence Spectrometer 50B (Perkin Elmer Ltd., Buckinghamshire, England) with an excitation wavelength of 509 nm and an emission wavelength of 533 nm. The results are presented in FIG. 32 in which the values are expressed as arbitrary fluorescence units. As FIG. 32 illustrates, plasmid DNA in lipid-nucleic acid complexes containing DODAC/ESM is condensed or protected by the lipid component. Moreover, the detergent (OGP) can dissolve the complex to uncondense the DNA (see FIG. 32).

DNA in lipid-nucleic acid particles containing DODAC/DOPE is partially accessible to TO-PRO-1 at a lipid/DNA charge ratio (+/−) of 4:1, however, at 8:1 DNA is completely protected by the lipid component. This result suggests that the nucleic acid (DNA) is partially condensed at the lower charge ratio and fully condensed at the higher ratio (FIG. 32).

EXAMPLE 21

This example demonstrates the stability of lipid-nucleic acid particles in phosphate-buffered saline and in serum containing media.

A lipid-nucleic acid particle formulation was prepared according to the procedure described in Example 19. Portions of the formulation (using either ESM or DOPE as the neutral lipid) were combined with PBS (140 mM NaCl, 10 mM $Na_2HPO_4$) or serum-containing medium and incubated for two hours at 37° C. The resulting complexes were isolated and examined for any changes in QELS size results or transfection efficiency. No difference was found for any of the formulations, indicating that the complexes were not disrupted by either sodium or serum components. One portion which was incubated with PBS for 10 days still showed very good transfection efficiency.

EXAMPLE 22

This example illustrates the protection of DNA against DNase I which is afforded by the lipid-nucleic acid particles.

Figure 33:
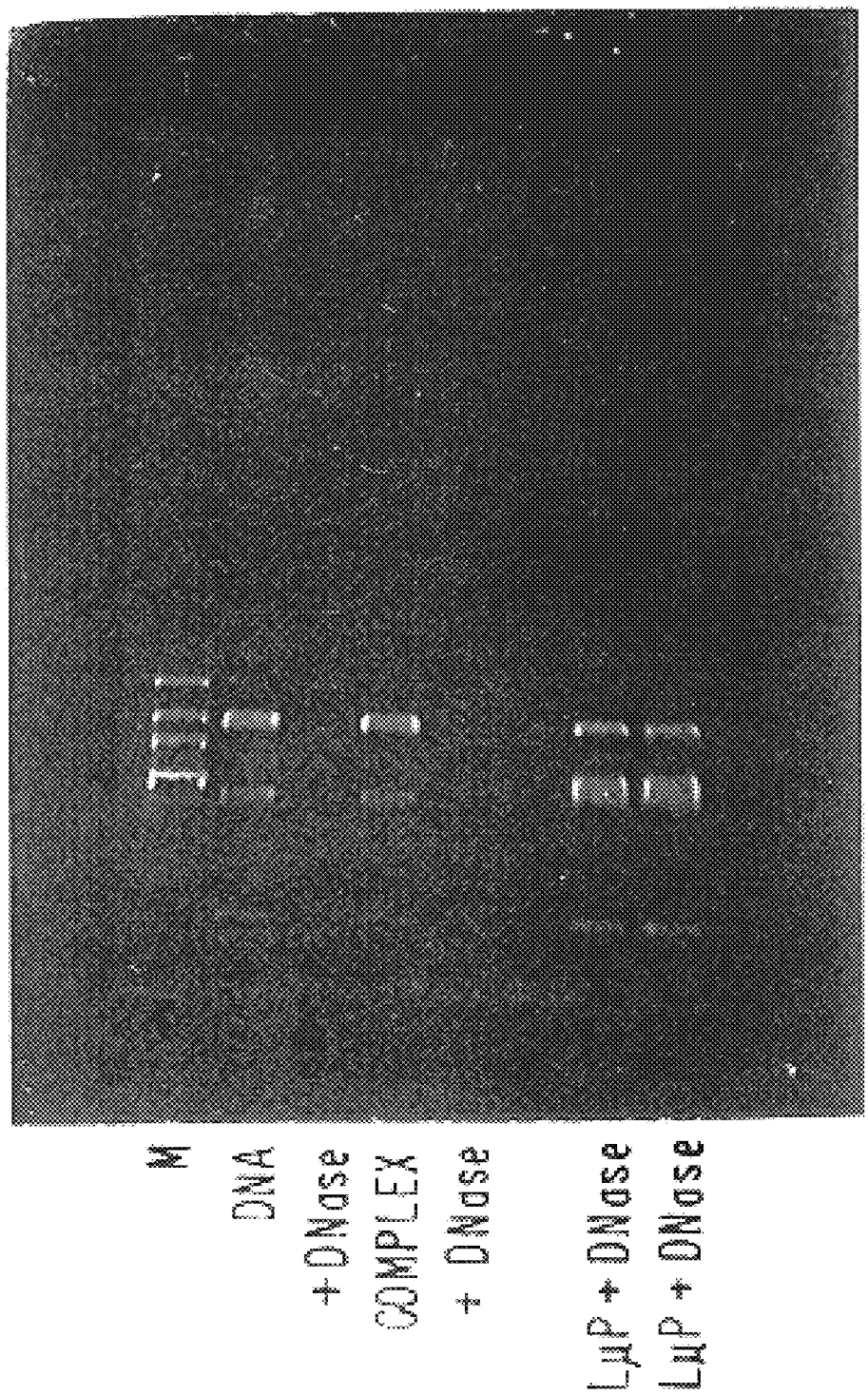
FIG. 33 shows the results of electrophoresis of DNA extracted from lipid-nucleic acid complexes following digestion with DNase I. DNA within the complex is protected from DNase I degradation whereas uncomplexed DNA is not protected.

A lipid-nucleic acid particle formulation of 10 µg DNA, 160 nmoles DODAC and 160 nmoles ESM in 1 mL total volume was prepared according to the method described in Example 19. The susceptibility of the DNA in this formulation to degradation by DNase I was evaluated by mixing the formulation with DNase I in the presence of OGP (1:1 charge ratio). The level of DNase I was equivalent to that which degrades uncomplexed DNA within 10 minutes at 37° C. The reactions were stopped after 10 min by the addition of 25 mM EDTA. DNA was extracted using the Bligh and Dyer extraction procedure in the presence of 150 mM NaCl. Under these conditions the cationic lipid/DNA complex dissociates and the resulting DNA can be efficiently recovered from the aqueous fraction. This DNA was precipitated with ¹⁄₁₀th volume of 3M sodium acetate (pH 5.2) and 2.5 volumes of 95% ethanol and recovered by centrifugation at 14,000 g for 30 min at 4° C. The DNA pellet was resuspended in sterile distilled water and subjected to electrophoresis on a 0.8% agarose gel (Gibco, BRL). The results are shown in FIG. 33. As FIG. 33 indicates, complexes containing ESM provide protection of DNA from DNase I degradation.

EXAMPLE 23

This example illustrates the in vitro transfection of CHO or B16 cell lines using lipid-nucleic acid particles prepared by the method of Example 19.

Figure 34:
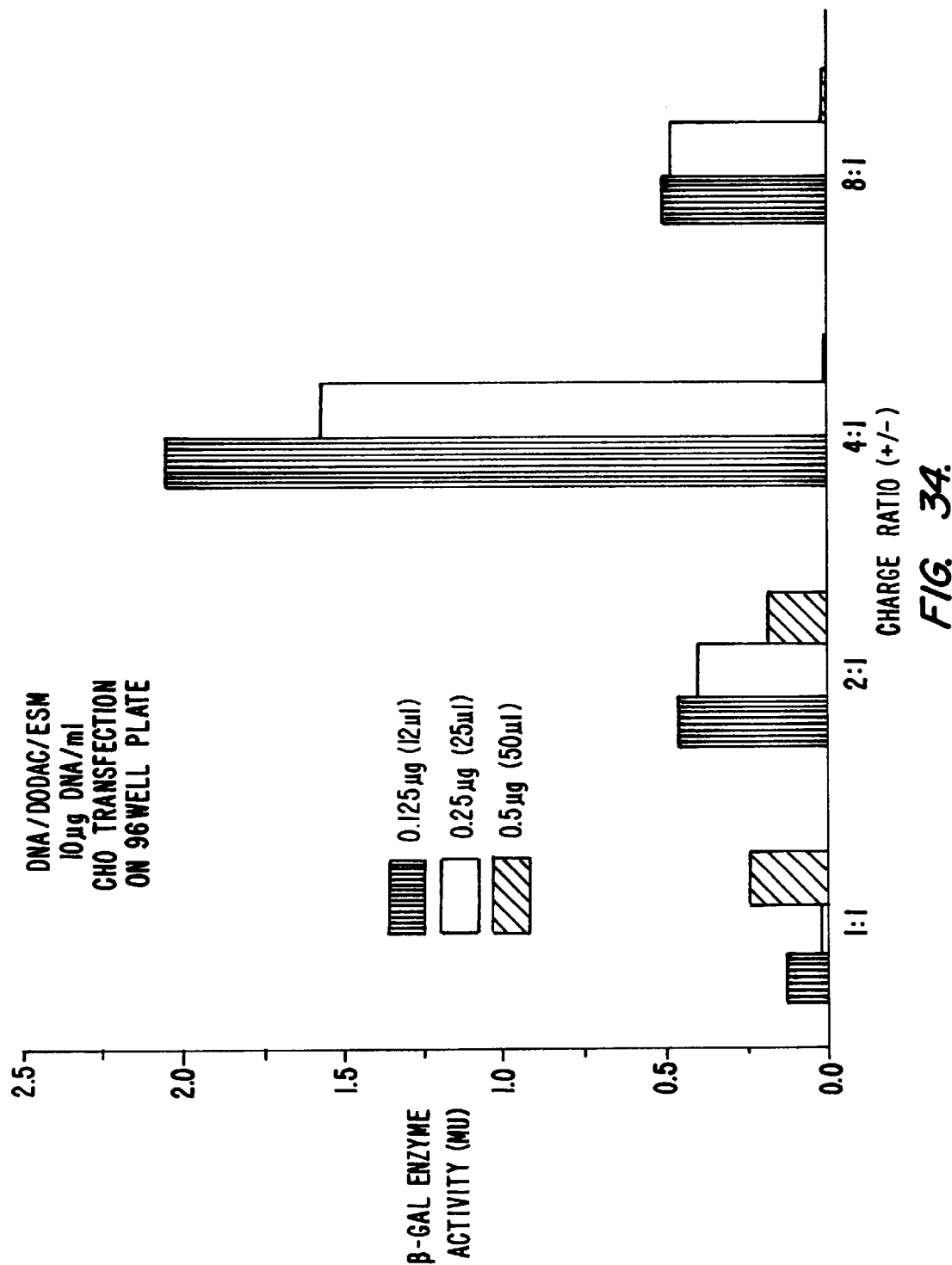
FIG. 34 provides the results of CHO cell lipofection using $\beta$-gal plasmid/DODAC/ESM as assayed by $\beta$-gal enzyme activity.

In vitro transfection was performed using a 96-well cell culture plate (Costar, Cambridge, Mass., USA) containing 50% confluent growth of either Chinese Hamster Ovary (CHO) or murine melanoma (B16) cell lines. Appropriate amounts (about 6–50 µL) of the lipid-nucleic acid particle formulation (10 µg DNA/mL) were premixed with medium containing 10% serum to a final volume of 150 µL. The medium surrounding the cells was removed using a needle syringe and replaced with the lipid-nucleic acid particles in 10% serum-containing medium. The cells and complex were incubated for a further 48 hours at 37° C. The transfection efficiency was evaluated using β-gal stain or an enzyme activity assay. Results are presented in FIG. 34.

The transfection study showed excellent transfection efficiency with ESM-containing complexes and with DOPE-containing complexes (not shown). A cationic lipid to DNA charge ratio of 3:1 to 4:1 gave the best in vitro transfection results.

EXAMPLE 24

This example illustrates the properties of nucleic acid-lipid particles prepared as described below in the presence of 100 mM (A) or 20 mM (B) n-octyl β-D-glucopyranoside (OGP).

The protocol involves the preparation of solutions of pCMVβ DNA in OGP and lipid-detergent mixed micelles. DODAC and the neutral lipid were dissolved in the same concentration of OGP used to dilute the DNA solution. To ensure that the lipids were completely dissolved, the mixtures were heated to 50° C. for 5 min and vortexed vigorously. Individual solutions were prepared with or without neutral lipid. When there was no neutral lipid involved, the DNA was added to the DODAC solution followed by gentle vortexing and then incubated at room temperature for 30 min. When the neutral lipid was present, the detergent solution containing DNA was mixed with the detergent solution containing the neutral lipid. This mixture was incubated for 30 min at room, temperature and then added to detergent solution containing the cationic lipid DODAC. To remove detergent mixtures were transferred to dialysis bags and dialyzed against six changes of sterile water over 72 hrs. The volume of each sample was less than 1 mL.

nucleic acid-lipid particle formation was evaluated by measuring changes in 90° light scattering intensity at 600 nm (slit width of 2.5 nm). This wavelength was used because light scattering from detergent micelles alone was negligible, therefore, the formation of nucleic acid-lipid particles could be monitored. This technique was also used to assess the ability of OGP to solubilize preformed liposomes of DODAC or SM. Multilamellar liposomes were prepared at a final lipid concentration of 1.0 mM by hydrating powdered lipid in distilled water at 60° C. The lipid suspensions were sonicated for 5 min (100 watts, 90% duty cycle, at 20 kHz) using a probe sonicator (Sonilier Cell Disrupter 350, Branson Sonic Power Co., Danbury, Conn.) to produce homogeneous suspension. For the lipid dissolution measurement, an aliquot of the lipid suspension was diluted with distilled water to a final lipid concentration of 0.2–1.0 mM. This lipid suspension was titrated with 200 mM OGP and mixed well by pipetting. Light scattering intensity was measured at room temperature using a Luminescence Spectrometer 50B (Perkin Elmer).

Figure 35A:
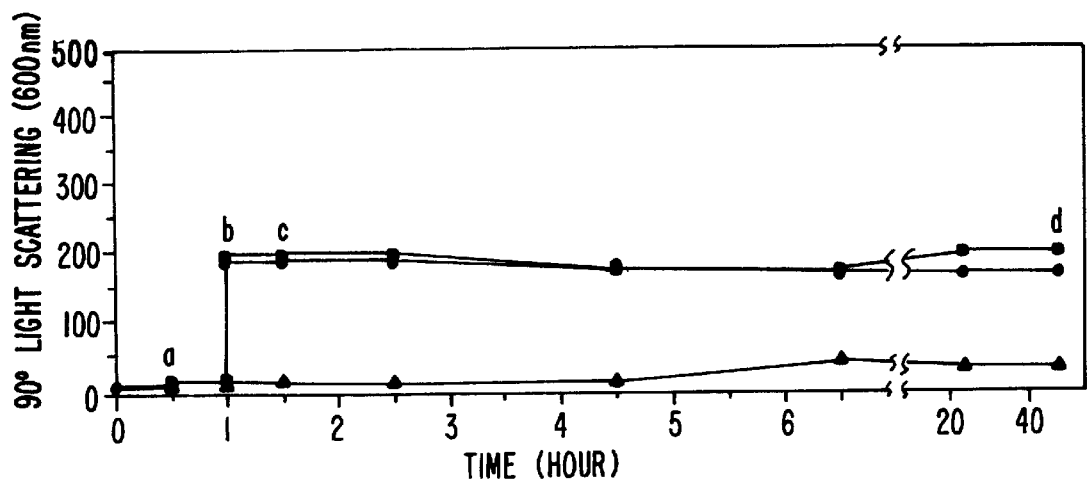
FIGS. 35A and B show changes in sample turbidity measured by 90° light scattering at 600 nm during the preparation of nucleic acid-lipid particles in the presence of 100 mM (A) or 20 mM (B) n-octyl $\beta$-D-glucopyranoside (OGP).
Figure 35B:
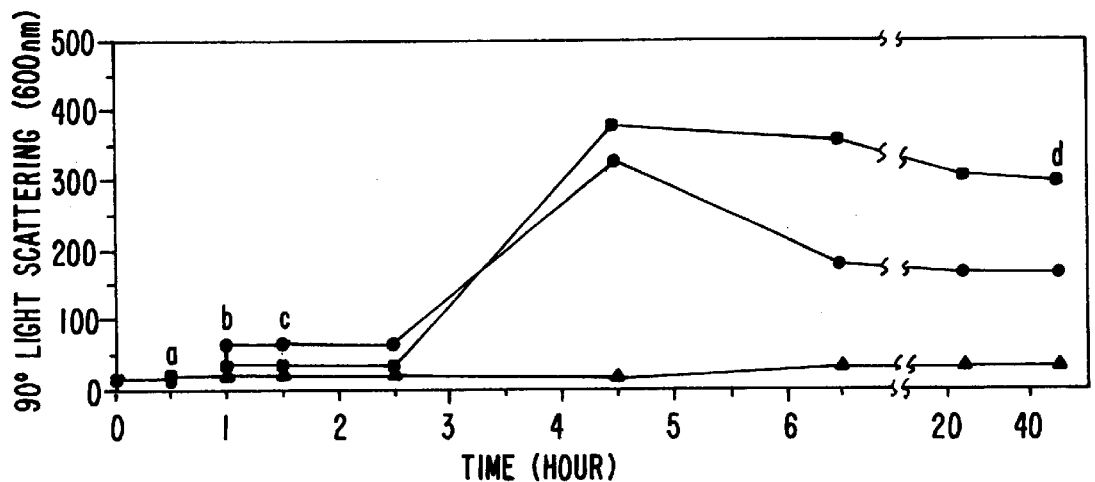
Figure 36:
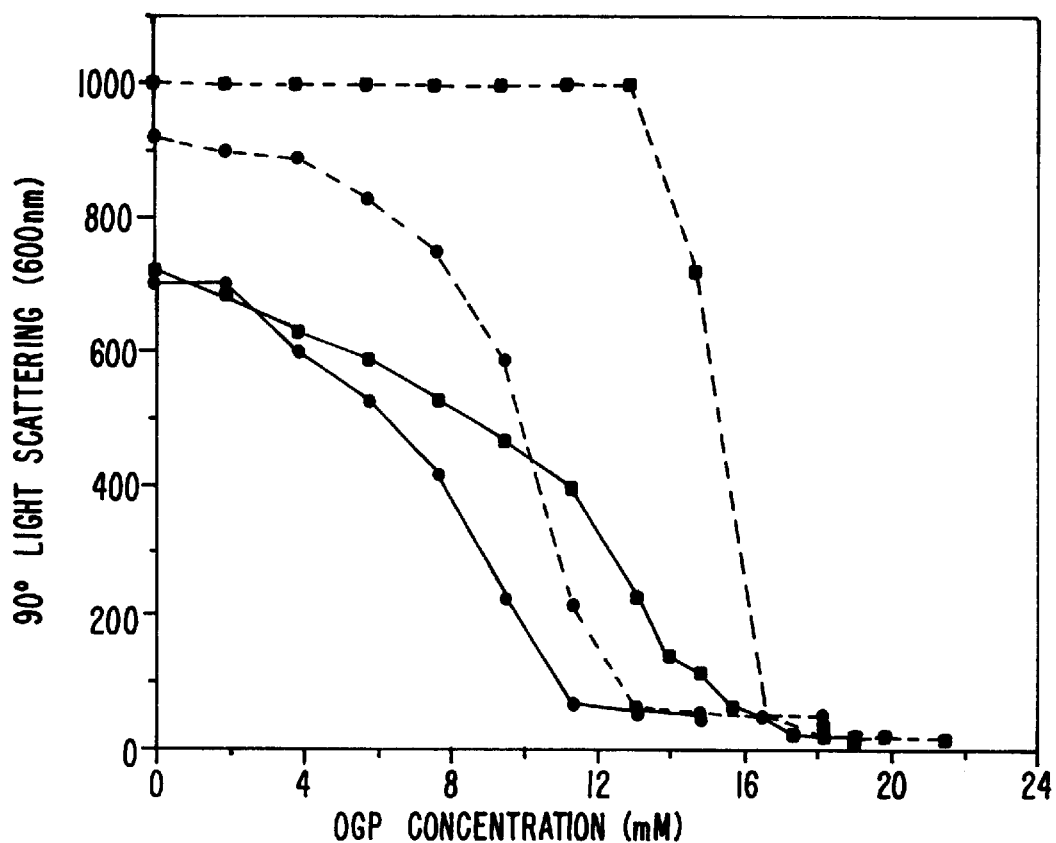
FIG. 36 shows solubilization of preformed DODAC (●) and SM (■) vesicles in OGP as measured by 90° light scattering. The concentrations of lipids used were 200 $\mu$M (solid lines) and 800 $\mu$M (broken lines).

In 100 mM OGP there were no significant changes in solution turbidity observed when DNA was added to DODAC/OGP mixed micelle solution in the presence and absence of SM. After 3 hrs of dialysis the solutions became turbid and light scattering increased, a reflection of increased particle size and/or aggregation. After 4.5 hrs., a decrease in light scattering was observed for systems prepared in the absence of SM, a result of the formation of larger visible aggregates. When the samples were prepared in 20 mM OGP (FIG. 35B), a concentration close to the critical micelle concentration of OGP in the absence of added lipids, light scattering increased at the time when DNA was added to DODAC/OGP micelles. This increase in turbidity is indicative of spontaneous particle formation spheroidal mixed micelles. It is therefore unlikely that lipid vesicles form under conditions where the detergent concentration is equal or greater than 20 mM. nucleic acid-lipid particle formation in the presence of 20 mM OGP is likely not due to DNA-mediated aggregation of cationic liposomes. We believe that nucleic acid-lipid particle formation is the result of the hydrophobic lipid-DNA complex adopting a structure that minimizes lipid acyl chain contact with water.

The physical characteristics of the nucleic acid-lipid particles, formed either spontaneously or following detergent removal, are summarized in Table 3 and FIG. 37. The parameters evaluated include (i) particle size as estimated by QELS and electron microscopy, (ii) the observed degree of aggregation/ flocculation, and (iii) an assessment of TO-PRO-1 binding, an intercalating agent that fluoresces when bound to DNA.

Since it is believed that nucleic acid-lipid particle formation is dependent on cationic lipid binding to DNA, particle characteristics were assessed under conditions where the cationic lipid to anionic phosphate charge ratio was varied from 1:1 to 8:1. Under conditions where particle formation occurred following detergent removal (i.e. lipid and DNA mixtures prepared in 100 Mm OGP) the resulting particles were large (>2000 nm) and aggregated (Table 3). This tendency to aggregate was dependent on the charge ratio.

After nucleic acid-lipid particle formation, the DNA assumed a structure that was not accessible to TO-PRO-1 intercalation, suggesting that the DNA was condensed. It should be noted that a condensation index of ≈1.0 is equivalent to that obtained when DNA is condensed by the addition of polylysine (Reimer et al., 1995).

When low detergent concentrations (20 mM OGP) were used to promote spontaneous nucleic acid-lipid particle formation there was no significant change in particle size or aggregation state as a function of detergent removal, except at charge ratios of 1:1 and 1.5:1 (Table 32), where significant increases in particle size were observed.

Figure 37A:
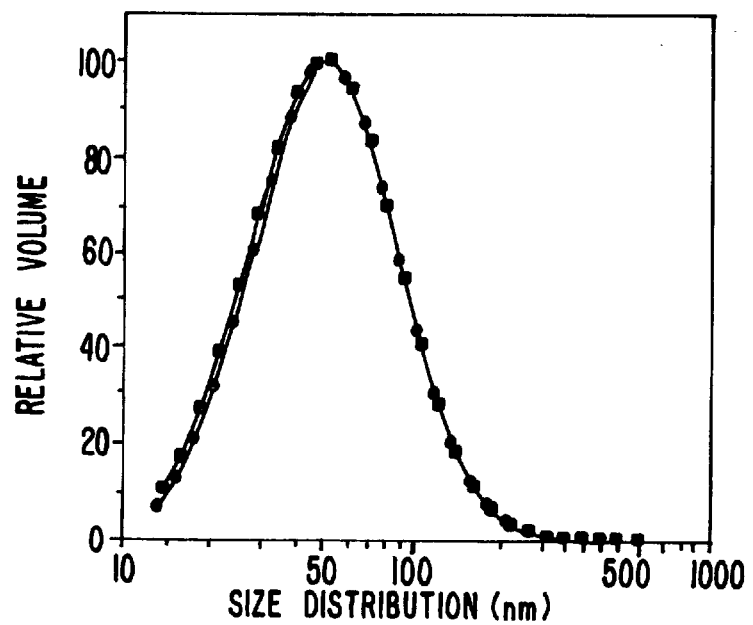
FIGS. 37A, 37B and 37C show volume-weighing particle size distribution determined by QELS operating in solid particle analysis mode for a nucleic acid-lipid particle formulation composed of pCMV$\beta$/DODAC/SM (charge ratio of 2:1, DODAC/SM mole ratio of 1:1) and prepared using 20 mM OGP before (●) and after (■) dialysis (A). The same nucleic acid-lipid particle formulation after dialysis was also examined by electron microscopy (B, negative stain and C, freeze-fracture). Bar=100 nm.
Figure 37B:
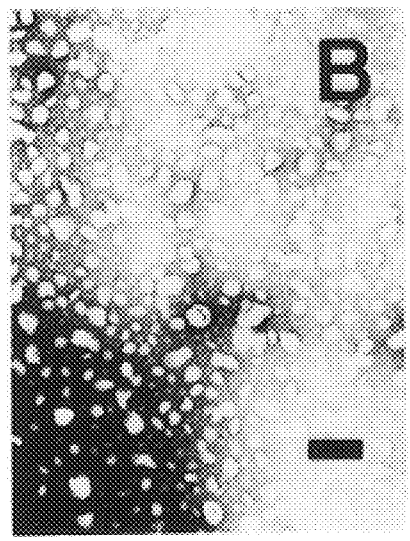
Figure 37C:
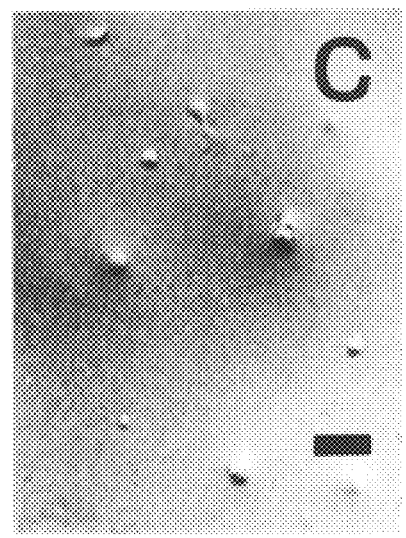

As shown in FIG. 37A, QELS data indicated that for samples prepared using the 2:1 charge ratio, the particles were homogeneous and fit a Gaussian analysis with a mean diameter of 59±38 nm.

This result is comparable with observations made using negative stain electron microscopy (FIG. 37B). nucleic acid-lipid particles were evaluated by electron microscopy (EM) using two methods. First, the samples were prepared for negative stain EM by placing a drop of a concentrated nucleic acid-lipid particle formulation (3 mM lipid) onto a formvar coated nickel grid. After 1 min the sample was carefully drawn away using filter paper and stained with a 2.5% ammonium molybdate solution. The stained samples were immediately examined and photographed using a Carl Zeiss EM10CR electron microscope operated at 80 Kv. Second, nucleic acid-lipid particles were prepared for freeze-fracture EM, where a sample of concentrated nucleic acid-lipid particle formulation (15 mM lipid) was mixed with glycerol (25% v/v), frozen in a freon slush, and subjected to freeze-fracture employing a Balzers BAF 400D apparatus. Micrographs were obtained using a JEOL Model JEM-1200EX electron microscope.

Data obtained from freeze-fracture electron microscopic analysis of the particles (FIG. 37C) indicated that, regardless of sample concentration (up to 15 mM total lipid), there were only a few regions on the freeze-fracture replica that exhibited fracture surfaces typical of membrane bilayer structures. Instead, numerous bumps were detected on the replica. This is consistent with the suggestion that particles rather than liposomes were formed using the procedures described here.

DNA was accessible to TO-PRO-1 following spontaneous particle formation and condensation indices of less than 0.05 were typically measured prior to detergent removal. This result was unexpected and suggests that particle formation is not a indicator of whether DNA is condensed. After detergent removal, TO-PRO-1 intercalation was not observed and the resulting DNA condensation indices were high (≈1.0) (Table 3).

TABLE 3

Characteristics of lipid-DNA particles formed with pCMVβ/DODAC/SM prepared using 20 mM and 100 mM OGP before and after dialysis.

| (cation/ anion$_a$) | mean diameter ± SD (nm)$^b$ | | aggregation state$^c$ | condensation index$^d$ |
|---|---|---|---|---|
| | before dialysis | after dialysis | | |
| 100 mM OGP | | | | |
| 1:1 | ND* | >2000 | ++ | 0.759 |
| 2:1 | ND | >2000 | + | 0.927 |
| 4:1 | ND | >2000 | + | 0.974 |
| 8:1 | ND | >2000 | ++ | 0.991 |
| 20 mM OGP | | | | |
| 1:1 | 71.2 ± 37.0 | 192 ± 110 | − | 0.875 |
| 1.5:1 | 63.1 ± 33.8 | 119 ± 76 | −− | 0.985 |
| 2:1 | 60.8 ± 33.3 | 58.6 ± 37.8 | −− | 0.991 |
| 4:1 | 56.7 ± 32.0 | 55.9 ± 32.6 | −− | 0.994 |
| 8:1 | 64.6 ± 33.4 | 66.4 ± 35.4 | ++ | 0.989 |

$^a$The charge ratio of cationic lipids to DNA phosphate groups.
$^b$Mean diameter was measured using QELS techniques as described in the Methods. The instrument used to evaluate particle size is accurate only under conditions where the mean particle size is less than 1.0 μm. The aggregation state of the formulations after dialysis was evaluated qualitatively through visual inspection of the samples and scored as follows: ++ large aggregates that settle out of solution within 5 min after sample mixing; + small to medium aggregates present but the solution retains a uniform "milky" appearance; − no obvious aggregates unless viewed by microscopy-, −− no aggregates and homogeneous as assessed by QELS.
$^d$DNA condensation index, a reflection of TO-PRO-1 binding to DNA in the presence and absence of lipid binding, was determined as described in Methods.
$^e$NID: not detectable because particles were not formed.

DNA Stability Assay

To evaluate the protective effect of lipids on DNA, 100 μl of the formulations containing I μg pCMVβ DNA were incubated with 0.67 unit of DNase I at 37° C. for 20 min in the presence of buffer (0.05 Ni Tris-HCI pH 8.0, 0.01 M MgSO$_4$, 0.1 mM dithiothreitol) or 20 mM OGP. The enzymatic reactions were stopped by the addition of 5 μl of 0.5M EDTA and 3 μl of 5M NaCl. DNA was extracted using a modified Bligh and Dyer extraction procedure (Reimer et al., 1995). Under these conditions, lipid and DNA dissociated and the resulting DNA was efficiently recovered in the aqueous phase. DNA was precipitated with one-tenth volume of sodium acetate (pH 5.2) and 2.5 volumes of 95% ethanol at −20° C. for 30 min and recovered by centrifugation at 12,000×g for 30 min at 4° C. in a microcentrifuge (Eppendorf). The DNA pellet was resuspended in 10 μl sterile distilled water and subjected to electrophoresis on a 0.8% agarose gel in TBE buffer (89 mM Tris-Borate, 2 mM EDTA, pH 8.0).

Figure 38A:
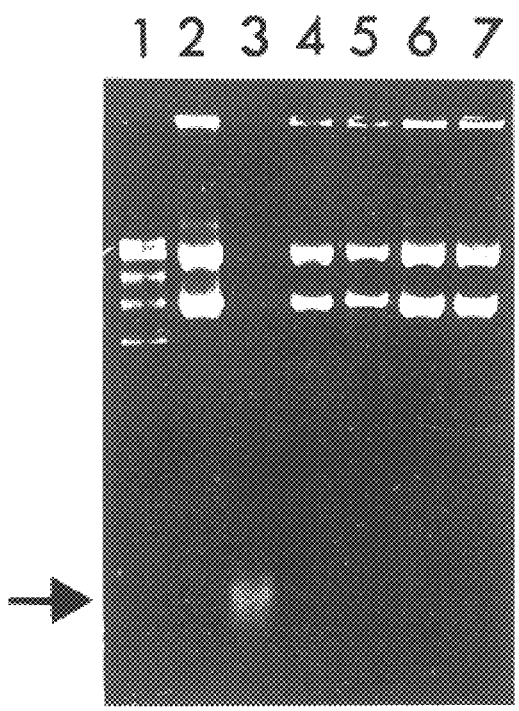
Figure 38B:
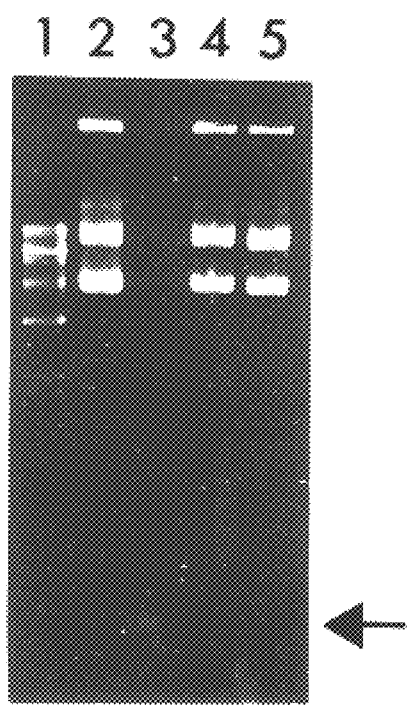

To further define the characteristics of the nucleic acid-lipid particles produced as a consequence of DNA-cationic lipid complex formation, we evaluated whether the DNA in the nucleic acid-lipid particles was protected against the endonuclease activity of DNase I. This is an important characteristic since we are developing these systems for in vitro and in vivo DNA transfer. The results presented in FIG. 38A show that after detergent removal, DNA within the particle remained intact in the presence of DNase I (lanes 5 and 7). Interestingly, DNA within particles that had formed spontaneously in the presence of 20 mM OGP remained intact in the presence of DNase I even in the absence of detergent removal (FIG. 38B, lane 5).

EXAMPLE 25

This example illustrates that the nucleic acid-lipid particles prepared as described in Example 24 are useful as plasmid delivery systems in vitro.

CHO cells (American Type Tissue Culture, Rockville, Md.) were plated at $2\times10^4$ cells per well in a 96 well culture plate (Costar, Cambridge, Mass.) in (αMEM supplemented with 5% Fetal Bovine Serum (FBS). The cells were grown for 24 hrs in a 37° C. 5% $CO_2$ incubator and were 40–50% confluent at the time of transfection. Media was removed from cells prior to addition of 100 μl of diluted nucleic acid-lipid particle formulations prepared from 25 μl nucleic acid-lipid particles formulation containing 0.3–1.2 μg DNA and 75 μl of (αMEM supplemented with 10% FBS. Cells were incubated at 37° C. for 4 hrs, prior to the addition of 100 μl of αMEM (10% FBS) containing 100 μg/mL gentamicin sulphate. The cells were further incubated at 37° C. for two days and then assayed for β-galactosidase activity. Media was removed from each well and 30 μl of a cell lysis buffer (0.1% Triton X-100, 250 mM $Na_2HPO_4$, pH 8.0) was added. Subsequently, 50 μl of bovine serum albumin (0.5% in phosphate buffer, pH 8.0) was added to each well followed by the addition of 150 μl of chlorophenol red galactopyranoside (CPRG, 1 mg/mL in 60 mM $Na_2HPO_4$, 1 mM $MgSO_4$, 10 mM KCl, 50 mM β-mercaptoethanol). Absorbance at 590 nm was read on a Titertek Multiscan Type 310C microtiter plate reader (Flow Laboratories, Mississauga, ONT) at various times and the resulting optical densities were converted to mU β-galactosidase using a standard curve obtained for each plate. All assays were evaluated in at least 3 wells per plate and the values are reported as means±standard deviations.

Figure 39A:
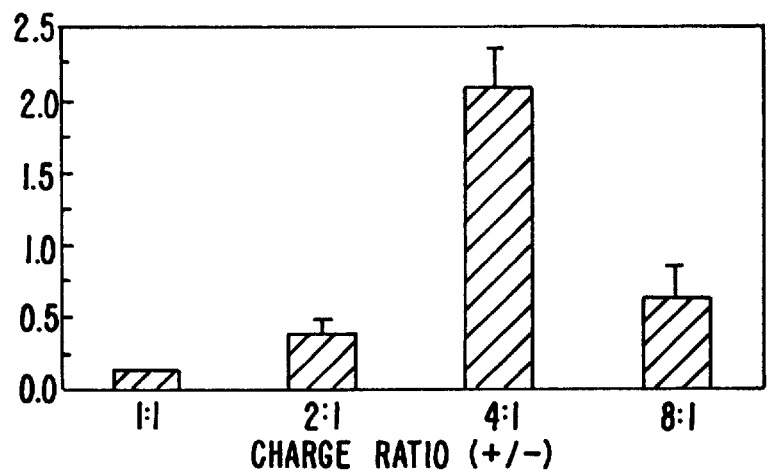
FIGS. 39A, 39B and 39C show in vitro Chinese Hamster Ovary (CHO) cell lipofection using nucleic acid-lipid particle formulations composed of pCMVβ /SM/DODAC (SM/DODAC mole ratio of 1:1 and charge ratio of 1:1 to 8:1) prepared using 100 mM OGP followed by dialysis. (A) Influence of charge ratio on β-galactosidase lipofection. (B) Particle induced toxicity as measured by reduced β-galactosidase activity per well for formulations prepared using a charge ratio of 4:1. (C) β-galactosidase lipofection achieved with nucleic acid-lipid particles prepared using SM (solid bar) or DOPE (hatched bar) as the neutral lipid (charge ratio of 4:1 and DODAC to neutral lipid mole ratio of 1:1).

Chinese Hamster Ovary (CHO) cell transfection studies using nucleic acid-lipid particles prepared using 100 mM OGP are presented in FIG. 39 and are evaluated by enzyme production (β-galactosidase activity) as the end product of gene transfer. Only those systems that were >2000 nm were effective at transfecting cells. The transfection efficiency for these systems increased as the cationic lipid to DNA nucleotide phosphate (charge) ratio increased from 1:1 to 4:1 (FIG. 39A). Unlike results with preformed liposome-DNA aggregates (see, e.g., Jarnagin et al., 1992); however,. transfection was not affected by the presence of serum.

Figure 39B:
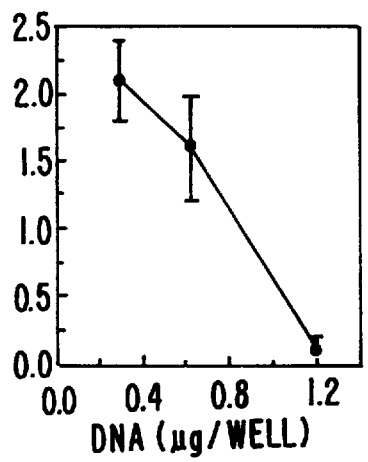

Particle-induced cell toxicity data are shown in FIG. 39B as a reduction in enzyme activity/well with increasing amounts of nucleic acid-lipid particle formulation.

Figure 39C:
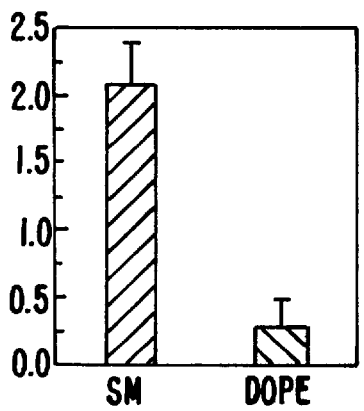
Figure 40:
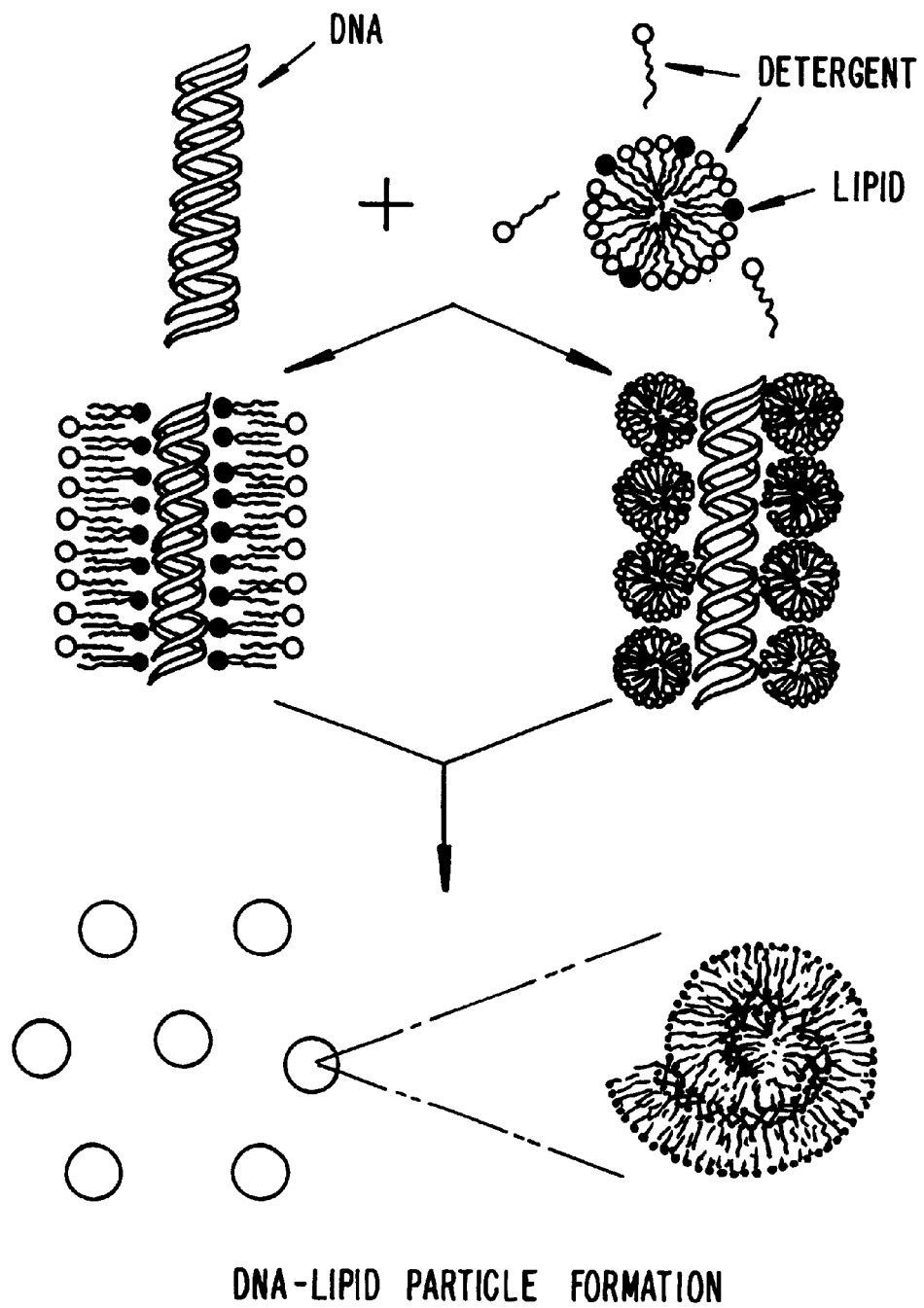
FIG. 40 is a model describing the intermediates that may be involved in the generation of a novel lipid-DNA particle.

A significant difference between preformed liposome-DNA aggregates and the nucleic acid-lipid particles concerns the use of DOPE as a helper lipid required for optimal transfection (Felgner & Ringold, 1989; Smith et al., 1993; Farhood et al., 1995). As shown in FIG. 39C, large particles prepared using the detergent dialysis procedure with DODAC and SM were more effective in transfecting CHO cells in vitro than particles prepared using DODAC and DOPE.

EXAMPLE 26

Figure 41A:
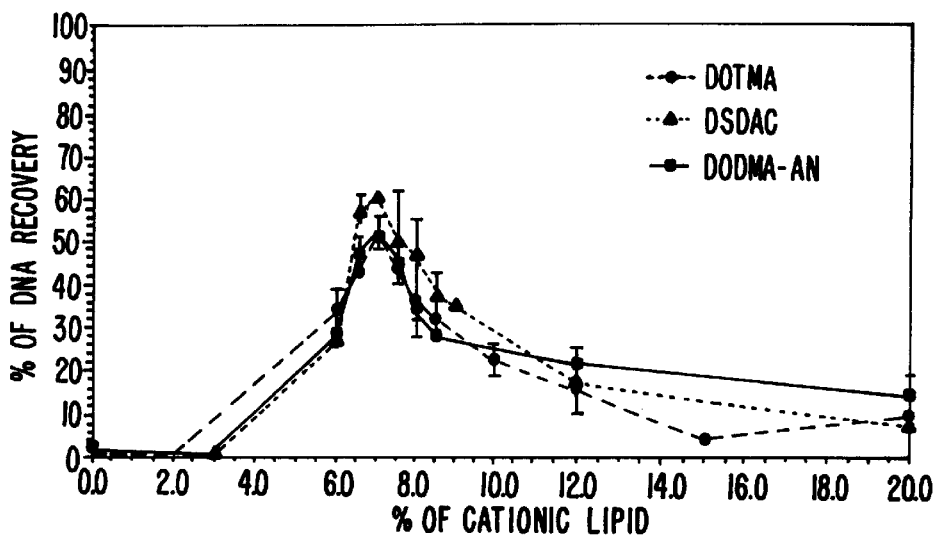
FIGS. 41A, 41B and 41C illustrate the encapsulation of plasmid DNA in a lipid vesicles by the detergent dialysis method using different cationic lipids.
Figure 41B:
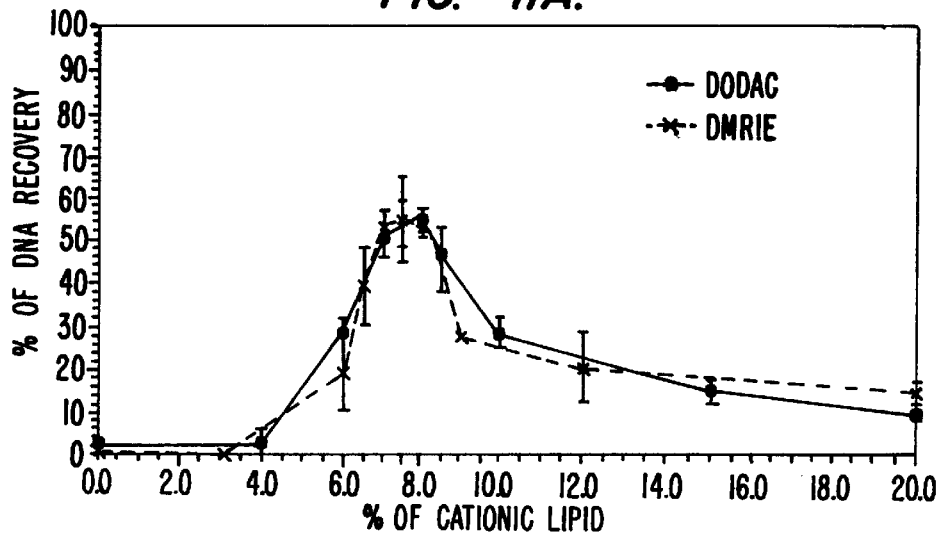
Figure 41C:
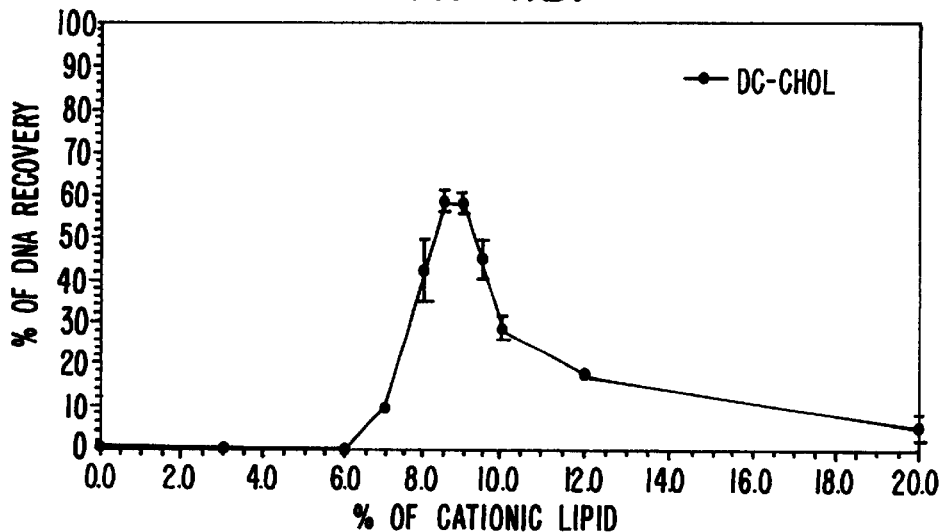

This example illustrates the encapsulation of plasmid DNA in a lipid vesicles by the detergent dialysis method using different cationic lipids. The dialysis method is as described previously for DODAC (EXAMPLE 1). The amount of plasmid entrapped with different mol % of the various cationic lipids was determined by DEAE Sepharose chromatography (described in EXAMPLE 2). The entrapment efficiency was similar for all cationic lipids tested with approximately 50 to 60% of plasmid DNA. The cationic lipid concentration required in the formulation for optimal plasmid encapsulation was 6.5% for DOTMA, DSDAC and DODMA-AN in FIG. 41(a); 8% DODAC and DMRIE in 41(b); DCchol in 41(c).

EXAMPLE 27

Figure 42A:
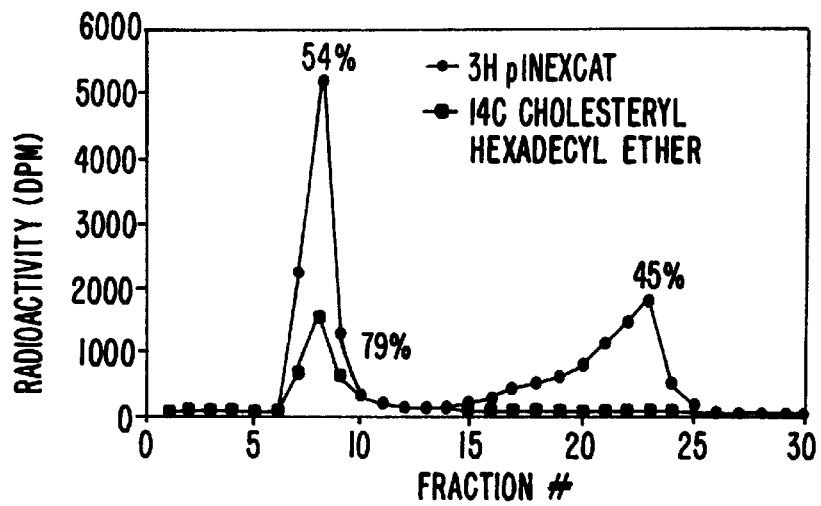
FIGS. 42A, 42B and 42C demonstrate the stability of plasmid containing vesicles prepared with different cationic lipids.
Figure 42B:
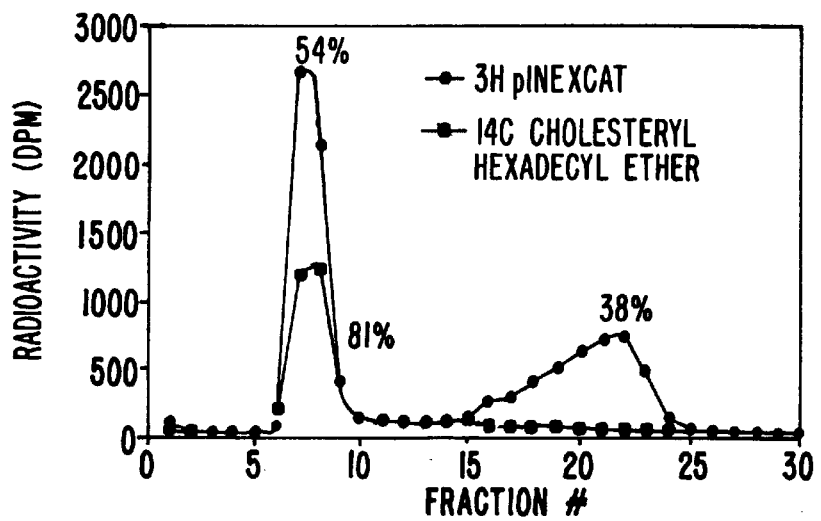
Figure 42C:
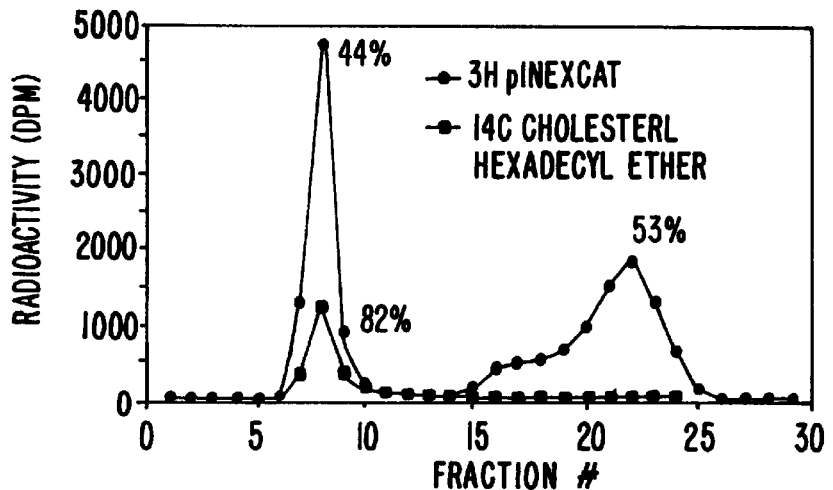

This example demonstrates the stability of plasmid containing vesicles prepared with different cationic lipids. The serum stability and protection of the plasmid form serum nucleases was determined by the method described in EXAMPLE 3. Stability and protection was similar for all preparations obtained with the different cationic lipids. As examples the elution. profile for preparations containing DODAC FIG. 42(a); DOTMA, FIG. 42(b), and DSDAC, FIG. 42(c) are given after incubation in mouse serum for 30 min at 37° C.

EXAMPLE 28

Figure 43:
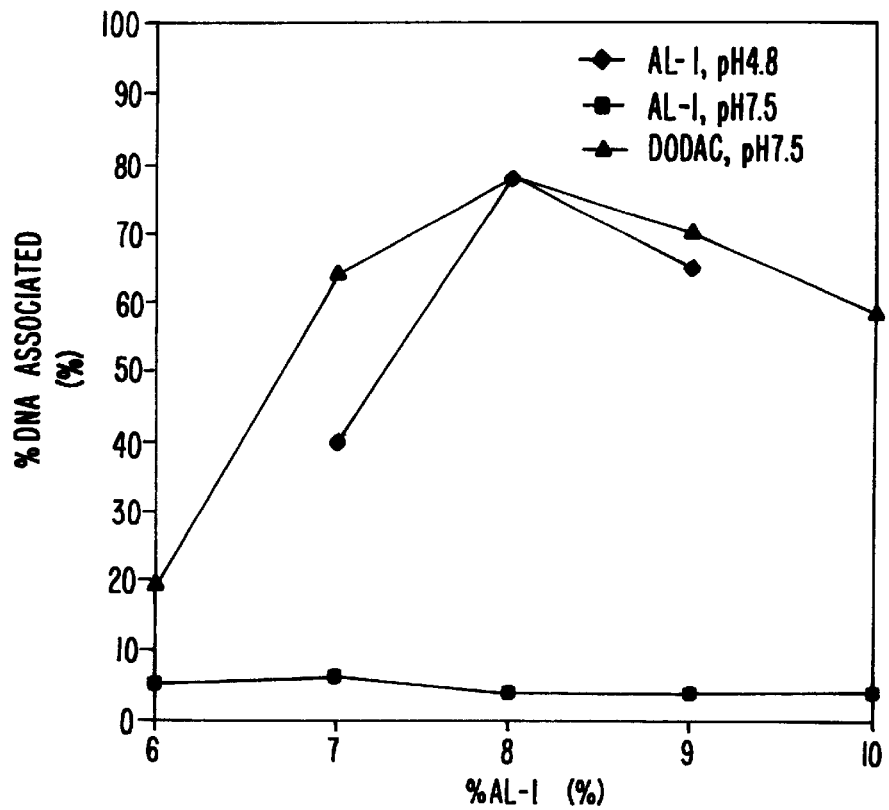
FIG. 43 demonstrates the encapsulation of plasmid DNA with the ionizable lipid AL-1 (pK=6.6) by the dialysis method

This example demonstrates the encapsulation of plasmid DNA with the ionizable lipid AL-1 ($pK_a$=6.6) by the dialysis method (as described in EXAMPLE 1). AL-1 is positively charged at acidic pH and neutral at pH>7. Different concentrations of AL-1 were used in the lipid formulations at pH 4.8 and 7.5 respectively. The amount of encapsulated DNA was determined using the PicoGreen assay. Non-encapsulated DNA was removed first by anion exchange chromatography and the entrapped DNA determined with PicoGreen after solubilization of the lipid vesicles in detergent. Encapsulation of plasmid DNA using DODAC is shown as comparison. At pH 4.8 maximal encapsulation of approximately 75% of plasmid DNA was achieved with 8% AL-1 similar to the DODAC formulation at pH 7.5. However, no DNA entrapment was obtained with AL-1 at pH 7.5. FIG. 43. This clearly demonstrates the requirement of positively charged lipids for DNA entrapment.

EXAMPLE 29

Figure 44:
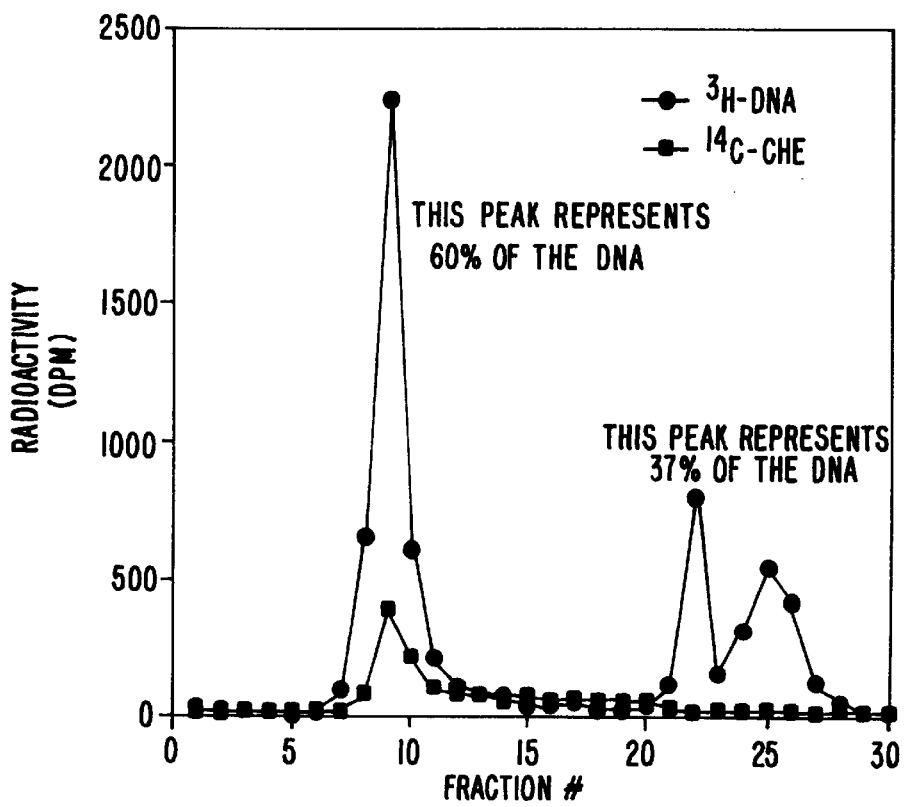
FIGS. 44 and 45 show the stability of the plasmid containing vesicles formed with AL-1 at pH 4.8 and the protection of the entrapped DNA from degradation by serum nucleases at pH 7.5.
Figure 45:
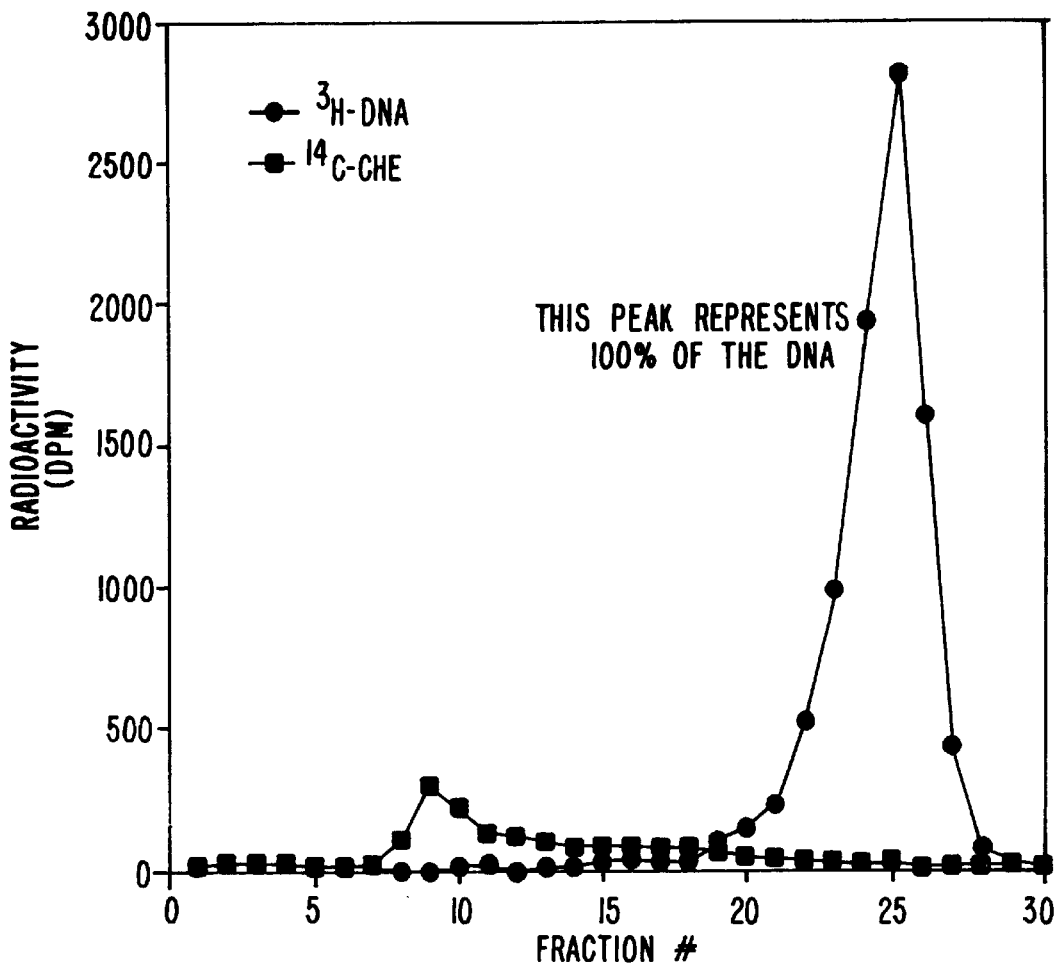

This example shows the stability of the plasmid containing vesicles formed with AL-1 at pH 4.8 and the protection of the entrapped DNA from degradation by serum nucleases at pH 7.5. $^3$H-DNA and $^{14}$C-CHE (cholesteryl hexadecyl ether) were used to follow the DNA and lipid respectively. The vesicles formed with AL-1 at Ph 4.8 were incubated in mouse serum for 1.5 hr at 37° C. at pH 7.5. The non-encapsulated DNA was not removed in the preparations used for serum incubation. After incubation in serum the vesicles were separated on a Sepharose CL6B column. Lipid and DNA were detected by radioactivity in the different fractions. FIG. 44. Approximately 60% of the DNA was protected from serum nucleases. When vesicles formed with AL-1 at pH 7.5 were incubated in serum virtually all the DNA was degraded and eluted as fragments separated from lipids. FIG. 45.

EXAMPLE 30

Figure 46:
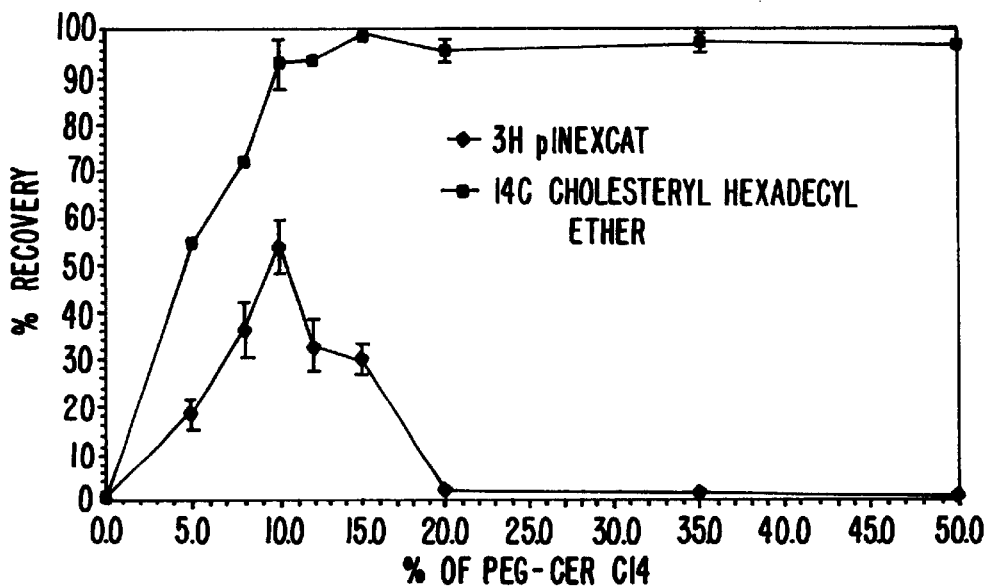
FIG. 46 demonstrates the effect of the PEG-ceramide concentration on the encapsulation efficiency by the dialysis method with 7.5% DODAC and DOPE.

Example 30 demonstrates the effect of the PEG-ceramide concentration on the encapsulation efficiency by the dialysis method with 7.5% DODAC and DOPE. The non entrapped DNA in the various formulations with different PEG-C14 concentrations was separated by DEAE Sepharose CL6B chromatography. DNA and lipid recovered are shown as a function of % PEG-C14. Best entrapment was obtained with 10 mol % PEG-C14. FIG. 46. However, a more recent experiment showed optimum entrapment in the range of 10 to 15 mol % (data not shown).

VII. Conclusion

As discussed above, the present invention comprises novel lipid-nucleic acid complexes and methods of making them. In a number of embodiments, hydrophobic DNA intermediates can be isolated and the DNA exists in a non-condensed form as measured by dye binding and DNase I sensitivity. These complexes can be used in the preparation of other lipid-nucleic acid particles.

In further embodiments, the invention provides methods for preparing serum-stable nucleic acid-lipid particles which are useful for the transfection of cells, both in vitro and in vivo.

The methods described for the preparation and uses of the various nucleic acid particles can be used with essentially any nucleic acid which can exist in a lipophilic state when complexed with an appropriate cationic lipid. Examples of some constructs include those encoding adenosine deaminase, the low density lipoprotein receptor for familial hypercholesterolemia, the CFTR gene for cystic fibrosis, galactocerebrosidase for Gaucher's disease, and dystrophin or utrophin into muscle cells for Duchenne's muscular dystrophy.

All publications, patents and patent applications mentioned in this specification are herein incorporated by reference into the specification for all purposes to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A method of introducing a nucleic acid into a cell, said method comprising contacting said cell with a nucleic acid-lipid particle comprising a cationic lipid, a conjugated lipid that inhibits aggregation of particles, and a nucleic acid, wherein said nucleic acid in said nucleic acid-lipid particle is resistant in aqueous solution to degradation with a nuclease.

2. The method of claim 1, wherein said particle is substantially non-toxic.

3. The method of claim 1, wherein said particle has a median diameter of less than about 150 nm.

4. The method of claim 1, wherein said cationic lipid is a member selected from the group consisting of N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxy)propylamine (DODMA), and a mixture of two or more of the above.

5. The method of claim 1, wherein said particle further comprises a non-cationic lipid.

6. The method of claim 5, wherein said non-cationic lipid is selected from the group consisting of DOPE, POPC and EPC.

7. The method of claimed 1, wherein said conjugated lipid is a PEG-lipid.

8. The method of claim 7, wherein said PEG-lipid comprises from 1% to about 15% of the total lipid present in said particle.

9. The method of claim 7, wherein said PEG-lipid is PEG-ceramide.

10. The method of claim 9, wherein the ceramide of said PEG-ceramide comprises a fatty acid group having 8 carbon atoms.

11. The method of claim 9, wherein the ceramide of said PEG-ceramide comprises a fatty acid group having 14 carbon atoms.

12. The method of claim 9, wherein the ceramide of said PEG-ceramide comprises a fatty acid group having 20 carbon atoms.

13. The method of claim 7, wherein said PEG-lipid is PEG-phosphatidylethanolamine.

14. The method of claim 1, wherein the nucleic acid:lipid ratio within said particle is at least 5 mg nucleic acid per mmol lipid.

15. The method of claim 1, wherein the nucleic acid:lipid ratio within said particle is at least 20 mg nucleic acid per mmol lipid.

16. The method of claim 1, wherein the nucleic acid:lipid ratio within said particle is at least 40 mg nucleic acid per mmol lipid.

17. The method of claim 1, wherein said nucleic acid is DNA.

18. The method of claim 1, wherein said nucleic acid is a plasmid.

19. The method of claim 1, wherein said nucleic acid is an antisense oligonucleotide.

20. The method of claim 1, wherein said nucleic acid is a ribozyme.

21. The method of claim 1, wherein said cationic lipid comprises 50% or less of the lipid present in said particle.

22. The method of claim 1, wherein said cationic lipid comprises from an amount greater than 0% to about 20% of the lipid present in said nucleic acid-lipid particle.

23. The method of claim 1, wherein the nucleic acid component of said particle is substantially not degraded after exposure of said particle to a nuclease at 37° C. for 20 minutes.

24. The method of claim 1, wherein the nucleic acid component of said particle is substantially not degraded after incubation of said particle in serum at 37° C. for 30 minutes.

25. The method of claim 1, wherein more than 10% of a plurality of such particles are present in plasma one hour after intravenous administration.

26. The method of claim 1, wherein said cell is present inside of a mammal, and wherein said transformation of said cell by said particle at a site distal to the site of administration is detectable for at least four days after intravenous injection.

27. The method of claim 1, wherein said cell is present inside of a mammal, and wherein said nucleic acid-lipid particle is administered parenterally to said mammal.

28. The method of claim 27, wherein said particle is administered to said mammal by intravenous injection.

29. The method of claim 27, wherein said particle is administered to said mammal by intraperitoneal delivery.

* * * * *